United States Patent
Nishimura

(10) Patent No.: US 11,007,276 B2
(45) Date of Patent: May 18, 2021

(54) INTRACELLULAR SUBSTANCE TRANSPORT SYSTEM AND USE THEREOF

(71) Applicant: NATIONAL UNIVERSITY CORPORATION HOKKAIDO UNIVERSITY, Sapporo (JP)

(72) Inventor: Shin-Ichiro Nishimura, Sapporo (JP)

(73) Assignee: National University Corporation Hokkaido University, Sapporo (JP)

( * ) Notice: Subject to any disclaimer, the term of this patent is extended or adjusted under 35 U.S.C. 154(b) by 117 days.

(21) Appl. No.: 16/073,677

(22) PCT Filed: Jan. 27, 2017

(86) PCT No.: PCT/JP2017/003880
§ 371 (c)(1),
(2) Date: Jun. 26, 2019

(87) PCT Pub. No.: WO2017/131242
PCT Pub. Date: Aug. 3, 2017

(65) Prior Publication Data
US 2020/0138973 A1 May 7, 2020

(30) Foreign Application Priority Data
Jan. 29, 2016 (JP) .............................. JP2016-015760

(51) Int. Cl.
| | |
|---|---|
| A61K 47/69 | (2017.01) |
| A61K 9/14 | (2006.01) |
| A61K 31/44 | (2006.01) |
| A61K 47/24 | (2006.01) |
| A61K 47/34 | (2017.01) |
| B82Y 5/00 | (2011.01) |

(52) U.S. Cl.
CPC ............ *A61K 47/6925* (2017.08); *A61K 9/14* (2013.01); *A61K 31/44* (2013.01); *A61K 47/24* (2013.01); *A61K 47/34* (2013.01); *A61K 47/6923* (2017.08); *B82Y 5/00* (2013.01)

(58) Field of Classification Search
CPC ............ A61K 47/6925; A61K 47/6923; A61K 47/24; A61K 47/23; A61K 9/14; C12N 9/99; A61P 35/00; A61P 43/00; B82Y 5/00
See application file for complete search history.

(56) References Cited

U.S. PATENT DOCUMENTS

2011/0262500 A1* 10/2011 Franco Puntes ......... B82Y 5/00
424/400

FOREIGN PATENT DOCUMENTS

| | | | |
|---|---|---|---|
| JP | 2007-254452 A | 10/2007 | |
| JP | 2009-534309 A | 9/2009 | |
| JP | 2010-515012 A | 5/2010 | |
| JP | 2011-528275 A | 11/2011 | |
| JP | 2014-214139 A | 11/2014 | |
| JP | 2015-520194 A | 7/2015 | |
| JP | 2015-520197 A | 7/2015 | |
| WO | 00/42012 A1 | 7/2000 | |
| WO | WO 2008/073187 A2 | 6/2008 | |
| WO | 2008/105773 A2 | 9/2008 | |
| WO | 2010/009335 A1 | 1/2010 | |
| WO | 2013/185032 A1 | 12/2013 | |
| WO | 2013/188979 A1 | 12/2013 | |
| WO | 2014/197937 A1 | 12/2014 | |

OTHER PUBLICATIONS

Tan, et al., title: Rapid Endolysosomal Escape and Controlled Intracellular Trafficking of Cell Surface Mimetic Quantum-Dots-Anchored Peptides and Glycopeptides; ACS Chem. Biol. 2015, 10, 2073-2086 (Year: 2015).*
International Preliminary Report on Patentability, dated Jul. 31, 2018, for International Application No. PCT/JP2017/003880, 10 pages. (w/ English Translation).
International Search Report and Written Opinion, dated Apr. 18, 2017, for International Application No. PCT/JP2017/003880, 15 pages. (w/ English Translation).
Nishimura et al., "Glycomics for Drug Discovery: Metabolic Perturbation in Androgen-Independent Prostate Cancer Cells Induced by Unnatural Hexosamine Mimics," *Angew. Chem. Int. Ed.* 51:3386-3390, 2012.

(Continued)

*Primary Examiner* — Yanzhi Zhang
(74) *Attorney, Agent, or Firm* — Seed IP Law Group LLP

(57) ABSTRACT

The present invention pertains to a complex including nanoparticles and, carried on the surface of the nanoparticles, a lysosomal enzyme inhibitor or kinase inhibitor shown by general formula (A) and a phospholipid mimetic substance shown by general formula (B).

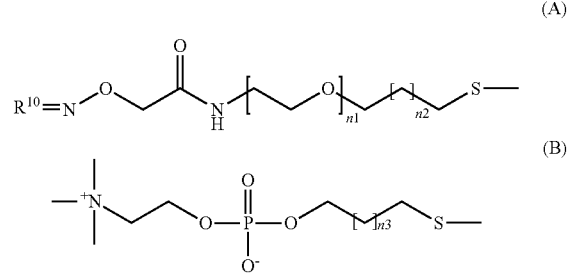

In general formula (A), n1 is an integer of 2-30, n2 is an integer of 2-30, the -S- terminal is a nanoparticle-carrying site, and R10 is a suicide substrate site or a kinase inhibition site. In general formula (B), n3 is an integer in the range of 2-30, and the -S- terminal is a nanoparticle-carrying site. The present invention provides a versatile system capable of efficiently delivering a drug to endolysosomes and allowing the drug to function at a low concentration on lysosomal enzymes, and an anticancer agent in which this system is used.

23 Claims, 20 Drawing Sheets

(56) References Cited

OTHER PUBLICATIONS

Ohyanagi et al., "Importance of Sialic Acid Residues Illuminated by Live Animal Imaging Using Phosphorylcholine Self-Assembled Monolayer-Coated Quantum Dots," *J. Am. Chem. Soc.* 133:12507-12517, 2011.

Tan et al., "Rapid Endolysosomal Escape and Controlled Intracellular Trafficking of Cell Surface Mimetic Quantum-Dots-Anchored Peptides and Glycopeptides," *ACS Chem. Biol.* 10:2073-2086, 2015.

Hinou et al., "Characterization of *Vibrio cholerae* Neuraminidase by a Novel Mechanism-Based Fluorescent Labeling Reagent," *Biochemistry* 44:11669-11675, 2005.

Hu et al., "Sorafenib (Nexavar): A Multikinase Inhibitor for Advanced Renal Cell Carcinoma and Unresectable Hepatocellular Carcinoma," *Modern Drug Synthesis*, Chapter 6: Sorafenib (Nexavar, pp. 73-85, 2010.

Ichikawa et al., "A Mechanism-Based Affinity-Labeling Agent for Possible Use in Isolating N-Acetylglucosaminidase," *Bioorganic & Medicinal Chemistry Letters* 11:1769-1773, 2001.

ChemIDplus, "Leupeptin," RN: 55123-66-5, retrieved on Mar. 3, 2021 from https://chem.nlm.nih.gov/chemidplus/rn/55123-66-5, 2 pages.

R&D Systems, "Pepstatin A," CAS No: 26305-03-3, retrieved on Mar. 3, 2021 from https://www.rndsystems.com/products/pepstatin-a 1990, 4 pages.

\* cited by examiner

EXTINCTION OF PEAK FOR FREE AO/PC CONFIRMED
THAT REACTION HAD PROCEEDED TO COMPLETION.

EXTINCTION OF PEAK FOR FREE AO/PC CONFIRMED
THAT REACTION HAD PROCEEDED TO COMPLETION.

INTRACELLULAR SUBSTANCE TRANSPORT SYSTEM AND USE THEREOF

TECHNICAL FIELD

The present invention relates to an intracellular substance transport system and use thereof.

CROSS-REFERENCE TO RELATED APPLICATION

The present application cites priority to Japanese Patent Application No. 2016-15760 filed Jan. 29, 2016, the contents of which are expressly incorporated herein in their entirely by reference.

BACKGROUND ART

Many target proteins for drugs expected to have therapeutic effects are distributed in the cytoplasm or in specific organelles within the cell, including the nucleus. Due to this, the expected therapeutic effect is not obtained when the drug cannot be delivered to the intracellular space where the drug is supposed to act.

Various drug delivery systems have been devised as a consequence, and in particular a variety of targetable systems are known that use, for example, polymer nanoparticles, micellar nanoparticles, and magnetic nanoparticles and that use, for example, EPR effects (refer, for example, to PTL 1 to PTL 4).

PTL 1: JP-A-2009-534309
PTL 2: JP-A-2011-528275
PTL 3: JP-A-2015-520194
PTL 4: JP-A-2015-520197
NPL 1: Shin-Ichiro Nishimura et al., Angew. Chem. Int. Ed. 2012, 51, 3386-3390
NPL 2: A. T. Ohyanagi, et. al., J. Am. Chem. Soc. 2011, 133, 12507-12517
NPL 3: B. R. S. Tan, et. al., ACS Chem. Biol. 2015, 10, 2073-2086
PTLs 1 to 4 and NPLs 1 to 3 are expressly incorporated herein by reference in their entirety.

SUMMARY OF INVENTION

Technical Problem

However, the therapeutically effective component must be taken up into the cell in order to obtain a therapeutic effect (NPL 1), and a versatile system that supports the function of a drug at low concentrations by efficiently transporting the drug, regardless of its high or low molecular weight, to a target intracellular space or a specific organelle, e.g., an endolysosome, is still unknown. The discovery of new methodologies and the development of new technologies are the biggest issues for this field.

The problem to be solved by the present invention is therefore to provide a versatile system that can support the function of a drug at low concentrations on lysosomal enzymes by efficiently transporting the drug to the endolysosome. An object of the present invention is to provide such a system.

A further object of the present invention is to provide a system that, using the aforementioned system for efficiently transporting a drug to the endolysosome, can deliver a substance (for example, an inhibitor) that is active against an enzyme within a cell membrane, for example, a kinase.

Another object of the present invention is to provide an anticancer agent that uses this system.

Solution to Problem

Focusing on the fact that many high-activity cells that reside in a stage during differentiation and growth typical of cancer engage in the uptake into the cell of, e.g., macromolecular substances and nanoparticles, by "endocytosis" and do so at a rate that is much higher than in normal cells, a method has been broadly established with the present invention by which small molecule drugs are effectively and selectively delivered into cells.

NPL 2 describes a conjugate of a glycan having, e.g., a sialic acid residue, in combination with a phospholipid on the surface of a metal nanoparticle. This report describes the administration of this conjugate to the mouse tail vein, whereupon the conjugate initially spreads throughout the body and thereafter localizes in specific organs. However, this report does not investigate the uptake of this conjugate into cells in a high state of activity, e.g., cancer cells.

The present invention is as follows.

[1]

A conjugate containing a nanoparticle, and a lysosomal enzyme inhibitor or kinase inhibitor represented by general formula (A) below and a phospholipid mimetic substance represented by general formula (B) below that are carried on the surface of the nanoparticle:

[C1]

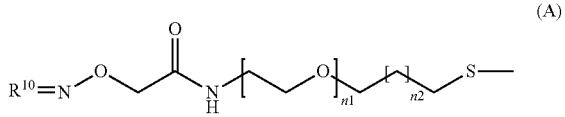

(in general formula (A), n1 is an integer from 2 to 30, n2 is an integer from 2 to 30, the -S- terminal is a nanoparticle-anchor moiety, and $R^{10}$ is a suicide substrate moiety or kinase inhibition moiety),

[C2]

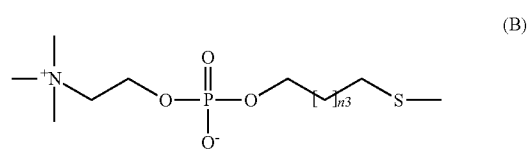

(in general formula (B), n3 is an integer in the range from 2 to 30 and the -S- terminal is the nanoparticle-anchor moiety).

[2]

The conjugate according to [1], wherein a substance represented by general formula (A') below is further carried on the nanoparticle surface:

[C3]

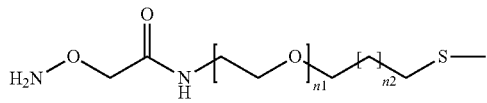
(A')

(in general formula (A'), n1 is an integer from 2 to 30, n2 is an integer from 2 to 30, and the -S- terminal is the nanoparticle-anchor moiety).

[3]
The conjugate according to [1] or [2], wherein, in general formulas (A), (B), and (A'), the sum of n1 and n2 is equal to or greater than n3.

[4]
The conjugate according to any one of [1] to [3], wherein the suicide substrate moiety contains a group that is reactive with an active center of a lysosomal enzyme (referred to as a reactive group herein below).

[5]
The conjugate according to [4], wherein the suicide substrate moiety has at least one sugar residue selected from the group consisting of an N-acetyl-D-glucosamine residue, an N-acetyl-D-gugalactosamine residue, a galactose residue, a glucose residue, a fucose residue, a mannose residue, and a sialic acid residue, and at least one reactive group selected from the group consisting of a difluoromethylaryl group and a trifluoromethylaryl group.

[6]
The conjugate according to [4], wherein the suicide substrate moiety contains the following functional group:

[C4]

(E)

(in the formula, R is at least one sugar residue selected from the group consisting of an N-acetyl-D-glucosamine residue, an N-acetyl-D-gugalactosamine residue, a galactose residue, a glucose residue, a fucose residue, a mannose residue, and a sialic acid residue, and LK is a linker).

[7]
The conjugate according to any one of [4] to [6], wherein the suicide substrate moiety contains any of functional groups represented by the following formulas.

[C5]

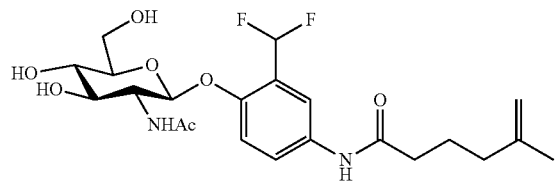
(7')

-continued

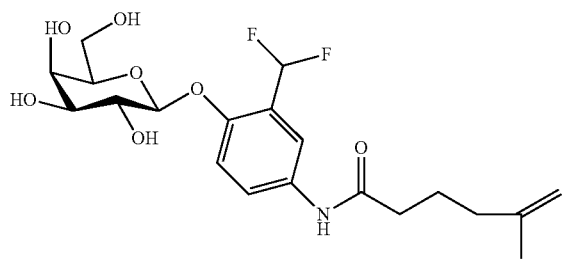
(15')

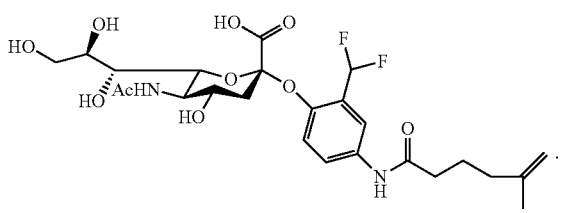
(20')

[8]
The conjugate according to any one of [1] to [3], wherein the kinase inhibition moiety contains a group having reactivity with a kinase (referred to as a cell membrane kinase-reactive group herein below).

[9]
The conjugate according to [8], wherein the kinase inhibition moiety contains any functional group represented by the following formula:

[C6]

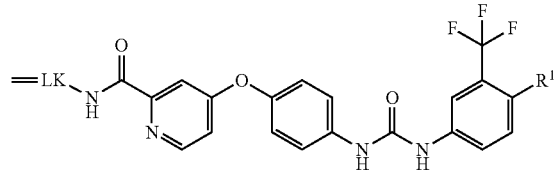

(in the formula, LK represents a linker and $R^1$ is an electron-withdrawing group).

[10]
The conjugate according to [8] or [9], wherein the kinase inhibition moiety contains a functional group represented by the following formula.

[C7]

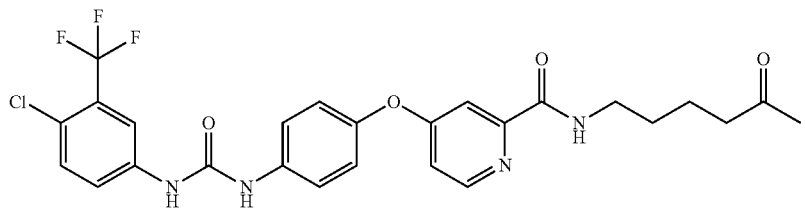

[11]
The conjugate according to any one of [1] to [10], wherein the molar ratio between the lysosomal enzyme inhibitor represented by general formula (A) and the phospholipid mimetic substance represented by general formula (B) is in the range from 1:100 to 10:1.

[12]
The conjugate according to any one of [2] to [11], wherein the molar ratio between the lysosomal enzyme inhibitor represented by general formula (A) and the substance represented by general formula (A') is in the range from 1:100 to 100:0.

[13]
The conjugate according to any one of [1] to [12], wherein the nanoparticle is a metal nanoparticle or a semiconductor nanoparticle.

[14]
The conjugate according to [13], wherein the metal nanoparticle is at least one particle selected from the group consisting of a gold nanoparticle, a platinum nanoparticle, a silver nanoparticle, and a magnetic iron nanoparticle.

[15]
The conjugate according to [13], wherein the semiconductor nanoparticle is a quantum dot.

[16]
The conjugate according to any one of [1] to [15], wherein the nanoparticle has a particle diameter in the range from 0.1 to 100 nm.

[17]
An anticancer agent containing, as an active ingredient, the conjugate according to any one of [1] to [16].

[18]
The anticancer agent according to [17], wherein the anticancer agent is an anticancer agent against breast cancer, prostate cancer, hepatocellular carcinoma, pancreatic cancer, colon cancer, ovarian cancer, renal cancer, lung cancer, or brain tumor.

[19]
A method for producing the conjugate according to any one of [1] to [16], the method comprising:
a step (1) of mixing a colloidal nanoparticle with an inhibitor crosslinking precursor X represented by general formula (C) below, and a phospholipid mimetic substance precursor represented by general formula (D) below to obtain a surface-modified nanoparticle carrying the inhibitor crosslinking precursor X and the phospholipid mimetic substance on the surface of the nanoparticle; and
a step (2) of obtaining the conjugate according to any one of [1] to [16] by mixing the obtained surface-modified nanoparticle with a lysosomal enzyme inhibitor precursor Y or a kinase inhibitor precursor Z and bringing about the ligation thereof with the inhibitor crosslinking precursor X to form a lysosomal enzyme inhibitor or kinase inhibitor represented by general formula (A) below, wherein the lysosomal enzyme inhibitor precursor Y contains a suicide substrate moiety that contains a group reactive with an active center of a lysosomal enzyme (referred to as a reactive group herein below) and the kinase inhibitor precursor Z contains a kinase inhibition moiety that contains a group reactive with a kinase:

[C8]

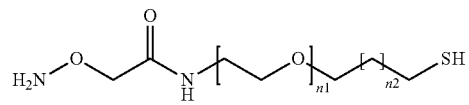

(C)

(in general formula (C), n1 is an integer from 2 to 30 and n2 is an integer from 2 to 30),

[C9]

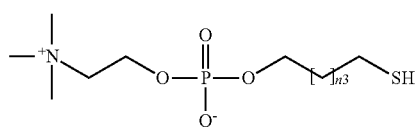

(D)

(in general formula (D), n3 is an integer in the range from 2 to 30),

[C10]

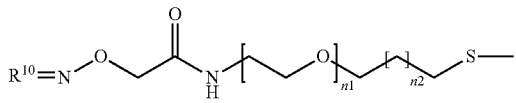

(A)

(in general formula (A), n1 is an integer from 2 to 30, n2 is an integer from 2 to 30, the -S- terminal is a nanoparticle-anchor moiety, and $R^{10}$ is the suicide substrate moiety or kinase inhibition moiety).

[20]
The production method according to [19], wherein the lysosomal enzyme inhibitor precursor Y is any compound represented by the following formulas.

[C11]

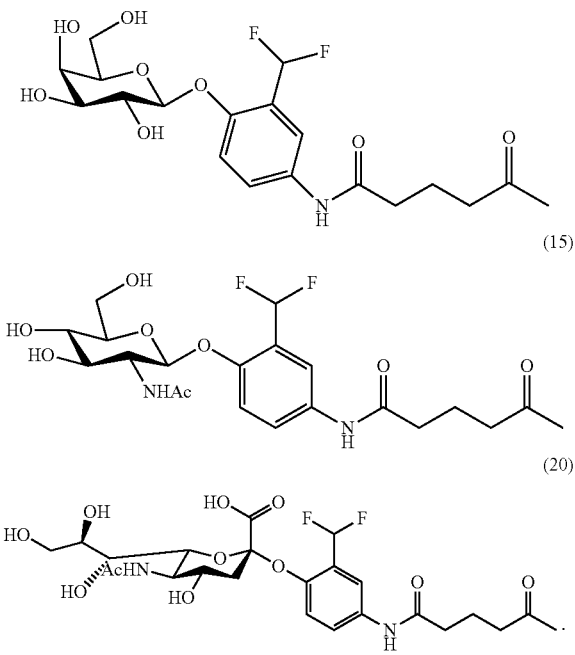

(7)

(15)

(20)

[21]
The production method according to [19], wherein the kinase inhibitor precursor Z is a compound represented by the following formula.

[C12]

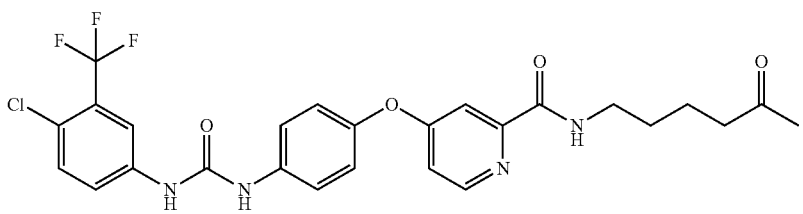

32

Advantageous Effects of Invention

The present invention enables the specific deactivation of an intracellular lysosomal enzyme or an intracellular kinase, and as a result can provide an antitumor agent that exhibits an antitumor effect at a concentration orders of magnitude lower than with conventional antitumor agents and enables the creation of very highly effective antitumor drug candidates.

DESCRIPTION OF EMBODIMENTS

<The Conjugate>

Figure 1:
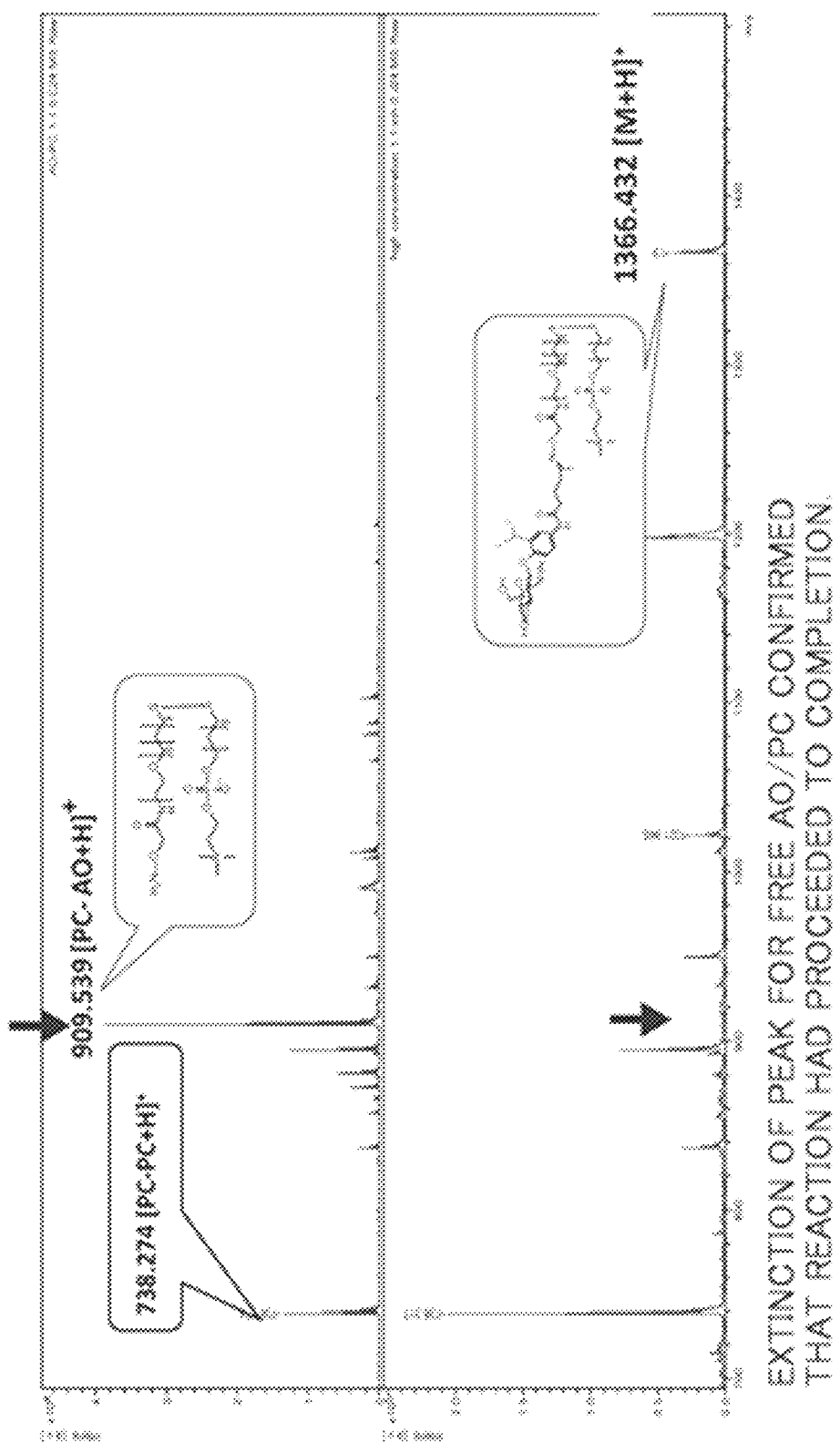
FIG. 1 confirms by MALDI-TOFMS the display of a compound in Example 1 on the nanoparticle surface.

The present invention relates to a conjugate that contains a nanoparticle, and a lysosomal enzyme inhibitor or kinase inhibitor represented by general formula (A) below and a phospholipid mimetic substance represented by general formula (B) below that are carried on the surface of the nanoparticle.

[C13]

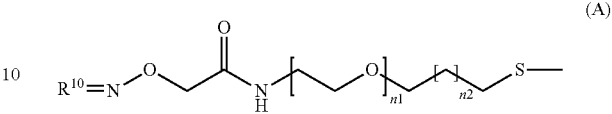

(A)

(In general formula (A), n1 is an integer from 2 to 30, n2 is an integer from 2 to 30, the -S- terminal is the nanoparticle-anchor moiety, and $R^{10}$ is a suicide substrate moiety or kinase inhibition moiety.)

[C14]

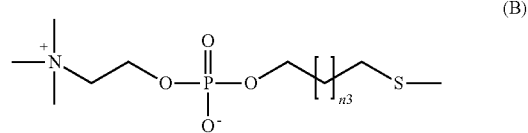

(B)

(In general formula (B), n3 is an integer in the range from 2 to 30 and the -S- terminal is the nanoparticle-anchor moiety.)

The lysosomal enzyme inhibitor contains a suicide substrate moiety that contains a group (the reactive group) that exhibits reactivity with an active center in a lysosomal enzyme. The suicide substrate moiety contains a sugar residue that can function as a substrate for the lysosomal enzyme and a group reactive with the lysosomal enzyme for the purpose of enzyme deactivation.

The sugar residue can be selected as appropriate in correspondence to the substrate specificity of the lysosomal enzyme for which deactivation is sought, and can be exemplified by at least one residue selected from the group consisting of an N-acetyl-D-glucosamine residue, an N-acetyl-D-gugalactosamine residue, a galactose residue, a glucose residue, a fucose residue, a mannose residue, and a sialic acid residue.

Considering the substrate specificities of lysosomal enzymes, the sugar residue is preferably an N-acetyl-D-glucosamine residue and/or a galactose residue.

A plurality of sugar residues may be used on one conjugate particle, in which case a single species or a plurality of species of sugar residues may be present on one conjugate particle. In addition, for different copresent conjugate particles for which a single species or a plurality of species of sugar residues are present on one conjugate particle, the same or different single species or plurality of species of sugar resides may also be present.

The reactive group should be a reactive group that exhibits reactivity with an enzymatic reaction center, and reactive groups that exhibit reactivity with an enzymatic reaction center can be exemplified by at least one reactive group selected from the group consisting of a difluoromethylaryl group and a trifluoromethylaryl group. The reactivity with an enzymatic reaction center may be reversible or irreversible.

Reference is made to Biochemistry, 2005, 44, 11669-11675 with regard to difluoromethylaryl groups being reactive groups that exhibit reactivity with enzymatic reaction centers. A suicide substrate in which the reactive group is a difluoromethylaryl group can be exemplified by groups represented by general formula (E) below.

[C15]

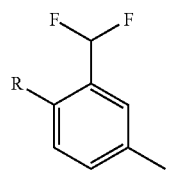

(E)

In the formula, R is a sugar residue and F is the fluorine atom.

General formula (E) can be general formula (E'), which additionally has a linker LK.

[C16]

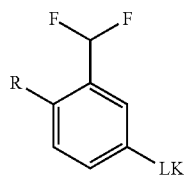

(E')

In the formula, R is a sugar residue and F is the fluorine atom. The linker LK is a group that can crosslink between a chain moiety and the sugar residue-bearing aryl group, but is not otherwise particularly limited. It can be, for example, the alkylene group-containing linker described below. In this formula, the left terminus is the bonding site with the aryl group, and the right terminus is the bonding site with the chain moiety, wherein the nitrogen atom (=N) at the terminus of the chain moiety is also displayed. The alkylene group in the linker LK can have, for example, 1 to 10 carbon atoms, and other connecting groups may also be used for, respectively, the amide group at the left terminus that is the bonding site with the aryl group and/or the imino group at the right terminus that is the bonding site with the chain moiety.

[C17]

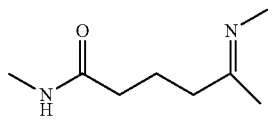

Reference is made to Bioorg. Med. Chem. Lett. 2001, 11, 1769-1773 with regard to trifluoromethylaryl groups being reactive groups that exhibit reactivity with enzymatic reaction centers.

The suicide substrate moiety can be, for example, a moiety containing any of functional groups represented by the following formulas.

[C18]

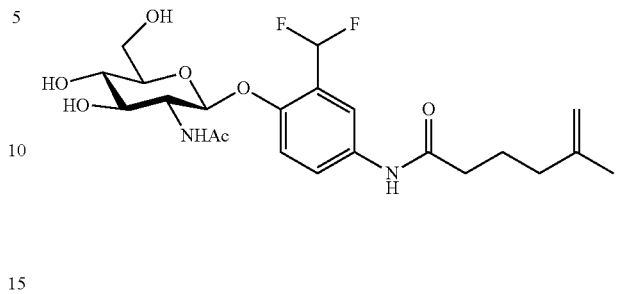

(7')

(15')

(20')

The kinase inhibition moiety contains a group that exhibits reactivity with a kinase and preferably contains a group that exhibits reactivity with a cell membrane kinase. Such a kinase inhibition moiety can be, for example, a moiety represented by the following formula.

[C19]

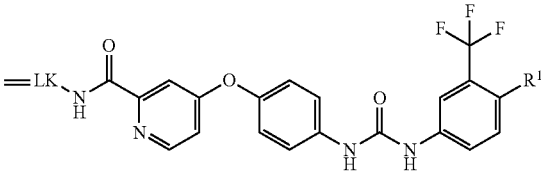

In the formula, LK represents a linker and $R^1$ is an electron-withdrawing group. The electron-withdrawing group can be exemplified by the halogen atoms (fluorine, chlorine, bromine, and iodine), nitro group, cyano group, tosyl group, acyl group, and so forth.

This kinase inhibition moiety includes sorafenib, as below.

[C20]

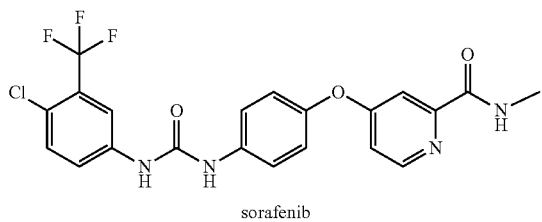

sorafenib

The following moiety is a specific example of a sorafenib-containing moiety.

[C21]

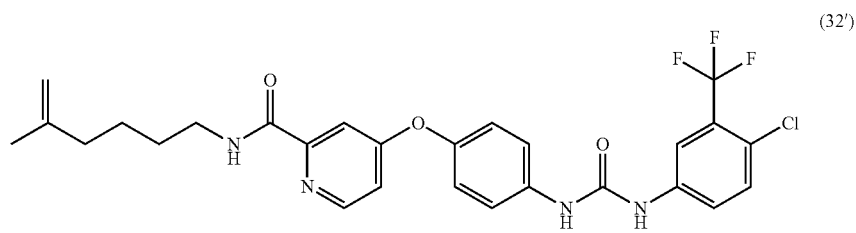

(32')

The kinases are a family of enzymes that catalyze the phosphorylation of specific residues on proteins. The kinases are generally divided into three groups: kinases that preferentially phosphorylate the serine and/or threonine residue; kinases that preferentially phosphorylate the tyrosine residue; and kinases that phosphorylate both tyrosine and serine/threonine residue. The kinases transduce an extracellular signal, including receptor activation by cytokine, to the nucleus and are essential for signal transduction pathways for causing various biological events. For example, gefitinib, erlotinib, cetuximab, and panitumumab are inhibitors of tyrosine kinase activation. Sorafenib is known as a drug that inhibits tyrosine kinase and Raf kinase (a type of serine/threonine kinase that is deeply involved in cell growth signaling).

The conjugate of the present invention is a substance that has, anchored on the surface of a nanoparticle, a suicide substrate moiety in a lysosomal enzyme inhibitor represented by general formula (A) or a kinase inhibition moiety in a kinase inhibitor represented by general formula (A), thereby presenting the suicide substrate moiety or kinase inhibition moiety on the nanoparticle surface. Here, "presentation" of the suicide substrate moiety or kinase inhibition moiety means the suicide substrate moiety or kinase inhibition moiety is anchored on the nanoparticle surface.

Through selection of the n1 and n2 in the formula for the lysosomal enzyme inhibitor or kinase inhibitor represented by general formula (A), the distance between the nanoparticle and the lysosomal enzyme inhibitor or kinase inhibitor can be maintained in a desired range and as a result the lysosomal enzyme deactivation action or kinase inhibition action can be adjusted. n1 is an integer in the range from 2 to 30, preferably 5 to 16, and more preferably 4 to 15. n2 is an integer in the range from 2 to 30, preferably 5 to 20, and more preferably 7 to 15.

The phospholipid mimetic substance represented by general formula (B) modifies the surface of the nanoparticle and confers the function of supporting the endocytosis-mediated uptake of the conjugate of the present invention into the cell. From this standpoint, n3 is an integer from 2 to 30, preferably 5 to 20, and more preferably 7 to 15.

The anchored amount, per one nanoparticle, of the lysosomal enzyme inhibitor or kinase inhibitor represented by general formula (A) and the phospholipid mimetic substance represented by general formula (B) is preferably equal to or more than 80% of the metal element (reaction sites) on the nanoparticle surface. This can be determined as appropriate based on considerations of the suppression of aggregation of the conjugate of the present invention with itself and the function of supporting endocytosis-mediated uptake into the cell. The anchored amount is more preferably an amount that can cover all of the reaction sites of the nanoparticle surface.

The ratio between the lysosomal enzyme inhibitor or kinase inhibitor represented by general formula (A) and the phospholipid mimetic substance represented by general formula (B) can be selected as appropriate based on a consideration of the balance between the lysosomal enzyme deactivation function or kinase inhibition function within the cell and the function of supporting endocytosis-mediated uptake into the cell. For example, the molar ratio here can be in the range from 1:100 to 10:1 and is preferably in the range from 1:10 to 1:1.

In addition to the lysosomal enzyme inhibitor or kinase inhibitor represented by general formula (A) and the phospholipid mimetic substance represented by general formula (B), the conjugate of the present invention may additionally carry a substance represented by general formula (A') below on the nanoparticle surface. The substance represented by general formula (A') originates from the precursor X used for crosslinking with the enzyme inhibitor represented by general formula (A), infra.

[C22]

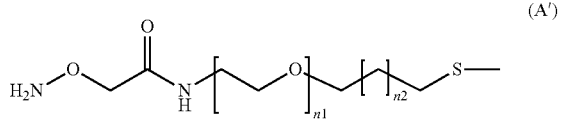

(A')

In general formula (A'), n1 is an integer from 2 to 30, n2 is an integer from 2 to 30, and the -S- terminal is the nanoparticle-anchor moiety.

As desired, a physiologically active substance, e.g., a glycan or antibody, can by additionally anchored at general formula (A').

The molar ratio between the lysosomal enzyme inhibitor or kinase inhibitor represented by general formula (A) and the substance represented by general formula (A') can be in the range from 1:100 to 100:0 or in the range from 10:100 to 100:10.

The nanoparticle can be a metal nanoparticle or a semiconductor nanoparticle. There are no particular limitations on the material of the metal nanoparticle, and it can be gold, platinum, silver, or magnetic iron. The metal nanoparticle can be a gold nanoparticle, platinum nanoparticle, silver nanoparticle, or magnetic iron nanoparticle. In particular, gold nanoparticles, platinum nanoparticles, and silver nanoparticles are preferred as the metal nanoparticles from the standpoint of safety for the organism.

There are no particular limitations on the material of the semiconductor nanoparticle. The semiconductor nanoparticle may be a quantum dot. A quantum dot, which is a fluorescent nanoparticle, is a small particle of approximately a dozen nanometers in which several hundred to several thousand semiconductor atoms are collected. The wavelength (color) of the emitted fluorescence varies as a function of the particle size. Commercial quantum dot products can be used, and, when a quantum dot is used for the nanoparticle in the conjugate of the present invention, a fluorescent conjugate can then be obtained and movement within an organism can also be monitored.

The particle diameter of the nanoparticle can be in the range from 0.1 to 100 nm and is preferably in the range from 1 to 50 nm, more preferably in the range from 5 to 20 nm, and still more preferably in the range from 5 to 15 nm.

The conjugate of the present invention can be schematically represented, for example, by general formula (10) below. The substituted phenyl group in the formula on the terminal side from the linker LK is an example of a lysosomal enzyme inhibitor, while a kinase inhibition moiety group is present on the terminal side from LK in the case of a kinase inhibitor (see below). In the actual conjugate, the nanoparticle NP carries at least one lysosomal enzyme inhibitor or kinase inhibitor represented by general formula (A) and at least one phospholipid mimetic substance represented by general formula (B).

In the branch corresponding to the lysosomal enzyme inhibitor represented by general formula (A), R in the formula is a sugar residue, F is the fluorine atom, and NP is a nanoparticle. LK is a linker between the sugar residue-bearing aryl group and the chain moiety that connects to the nanoparticle NP. There are no particular limitations on the linker LK as long as it is a group that can bridge between the chain moiety and the sugar residue-bearing aryl group. An example is the alkylene group-containing linker represented by the formula given below. In this formula, the left terminus is the bonding site with the aryl group and the right terminus is the bonding site with the chain moiety, wherein the nitrogen atom (=N) at the terminus of the chain moiety is also displayed. The alkylene group in the linker LK can have, for example, 1 to 10 carbon atoms, and other connecting groups may also be used for, respectively, the amide group at the left terminus that is the bonding site with the aryl group and/or the imino group at the right terminus that is the bonding site with the chain moiety.

[C24]

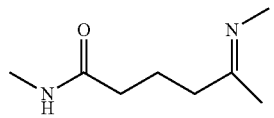

The conjugate that can be schematically represented by general formula (10) above can be schematically illustrated by general formula (20) below, in which a specific identity is provided for LK. R, F, and NP are the same as in general formula (10). In the actual conjugate that is schematically represented by general formula (20), the nanoparticle NP carries at least one lysosomal enzyme inhibitor represented by general formula (A) and at least one phospholipid mimetic substance represented by general formula (B).

[C23]

(10)

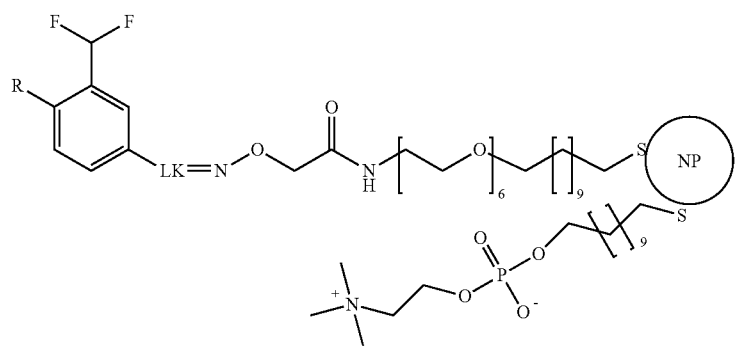

[C25]

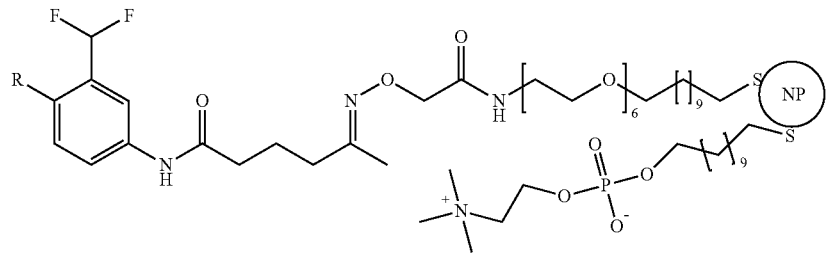

(20)

The conjugate bearing the kinase inhibitor represented by general formula (A) can be schematically illustrated by general formula (30) below.

[C26]

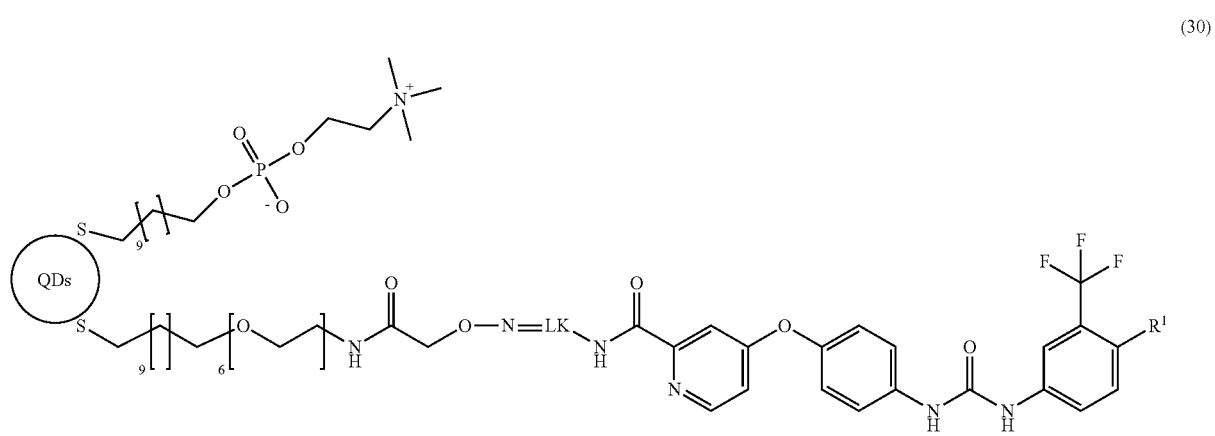

(30)

In the branch corresponding to the kinase inhibitor represented by general formula (A), $R^1$ is an electron-withdrawing group; the electron-withdrawing group can be exemplified by the halogen atoms (for example, fluorine, chlorine, bromine, and iodine), nitro group, cyano group, tosyl group, acyl group, and so forth; F is the fluorine atom, and QD is a colloidal quantum dot, which is one type of nanoparticle. LK is a linker between the amide group side and the chain moiety that links to the QD. There are no particular limitations on the linker LK as long as this group can bridge between the amide group side and the chain moiety. An alkylene group-containing linker is an example.

The conjugate that can be schematically represented by general formula (30) above can be schematically indicated by following formula (40) below wherein LK and $R^1$ have been given specific identities. F and QD are the same as in general formula (30). In the actual conjugate represented by formula (40), the nanoparticle QD carries at least one kinase inhibitor represented by general formula (A) and at least one phospholipid mimetic substance represented by general formula (B).

[C27]

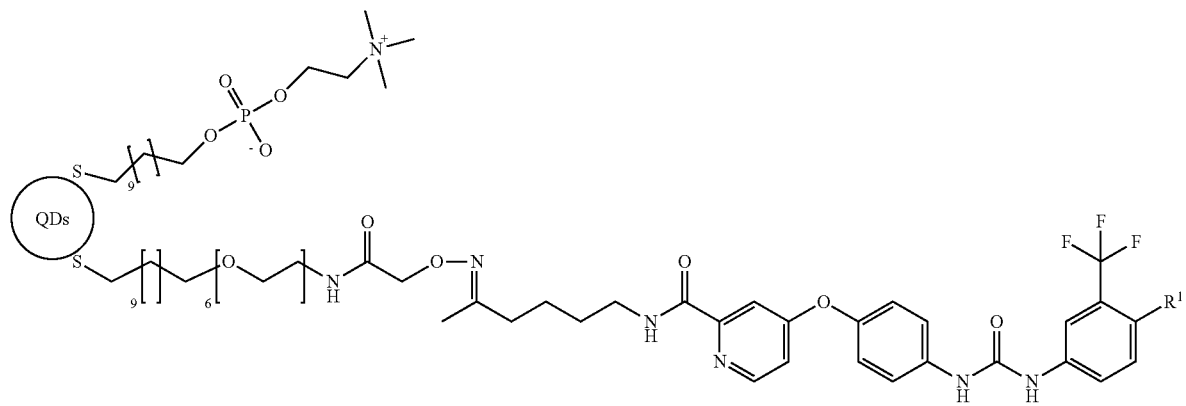

(40)

<Method for Producing the Conjugate>

The present invention includes a method for producing the above-described conjugate of the present invention. This method includes a step (1) of mixing a colloidal nanoparticle with an inhibitor crosslinking precursor X represented by general formula (C) below, and a phospholipid mimetic substance precursor represented by general formula (D) below to obtain a surface-modified nanoparticle carrying the inhibitor crosslinking precursor X and the phospholipid mimetic substance on the surface of the nanoparticle; and a step (2) of obtaining the conjugate of the present invention by mixing the obtained surface-modified nanoparticle with a lysosomal enzyme inhibitor Y or a kinase inhibitor precursor Z and bringing about the ligation thereof with the inhibitor crosslinking precursor X to form a lysosomal enzyme inhibitor or kinase inhibitor represented by general formula (A) below.

[C28]

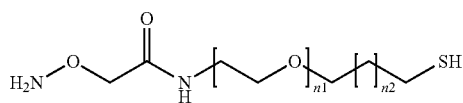

(C)

In general formula (C), n1 is an integer from 2 to 30 and n2 is an integer from 2 to 30.

[C29]

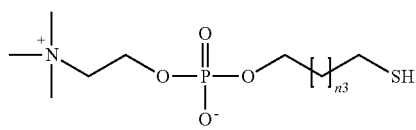

(D)

In general formula (D), n3 is an integer in the range from 2 to 30.

[C30]

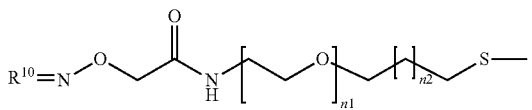

(A)

In general formula (A), n1 is an integer from 2 to 30, n2 is an integer from 2 to 30, the -S- terminal is the nanoparticle-anchor moiety, and $R^{10}$ is a suicide substrate moiety or a kinase inhibition moiety.

Step (1)

The step (1) is a step of mixing a colloidal nanoparticle with an inhibitor crosslinking precursor X represented by general formula (C) and a phospholipid mimetic substance precursor represented by general formula (D) to obtain a surface-modified nanoparticle carrying the inhibitor crosslinking precursor X and the phospholipid mimetic substance on the surface of the nanoparticle.

General formula (C) is the same as the lysosomal enzyme inhibitor or kinase inhibitor represented by general formula (A), with the exception that general formula (C) lacks the suicide substrate moiety or kinase inhibition moiety and has the SH group at the terminal. n1 in general formula (C) is an integer in the range from 2 to 30, preferably 5 to 20, and more preferably 7 to 15. n2 is an integer in the range from 2 to 30, preferably 5 to 20, and more preferably 7 to 15. General formula (D) is the same as the phospholipid mimetic substance represented by general formula (B), with the exception that the terminal in general formula (D) is the SH group. n3 in general formula (D) is an integer in the range from 2 to 30, preferably 5 to 20, and more preferably 7 to 15. The inhibitor crosslinking precursor X represented by general formula (C) and the phospholipid mimetic substance precursor represented by general formula (D) are both available as commercial products and may also be prepared by the method described in a reference document (T. Ohyanagi et al., J. Am. Chem. Soc. 2011, 133, 12507-12517).

The mixing ratio among the inhibitor crosslinking precursor X represented by general formula (C), the phospholipid mimetic substance precursor represented by general formula (D), and the nanoparticle can be determined as appropriate based on a consideration of the desired amounts of the inhibitor crosslinking precursor X represented by general formula (C) and the phospholipid mimetic substance precursor represented by general formula (D) to be anchored on the nanoparticle.

Step (1) in Example 1 is illustrated for reference below. In the scheme indicated below, n1 in the inhibitor crosslinking precursor X represented by general formula (C) is 6 and n2 is 9, while n3 in the phospholipid mimetic substance precursor represented by general formula (D) is 9. In the scheme given below, which is the reaction scheme of Example 1, the molar ratio AO/PC between the aminooxy linker (AO) and the phosphorylcholine linker (PC) is 1/2. AO/PC is 1/2 in Example 2, 1/4 in Example 3, and 1/16 in Example 5. The AO/PC molar ratio can be a ratio that follows from the teaching above that the ratio between the lysosomal enzyme inhibitor or kinase inhibitor represented by general formula (A) and the phospholipid mimetic substance represented by general formula (B) can be in the range, for example, of 1:100 to 10:1 as the molar ratio and is preferably in the range from 1:10 to 1:1 as the molar ratio.

pholipid mimetic substance are carried on the nanoparticle surface. This is carried out in the scheme indicated above at room temperature (for example, 15° C. to 25° C.) using a mixed solvent of hexane and water for the solvent. The solvent used can be determined as appropriate in conformity with the type of colloidal nanoparticle and the type of inhibitor crosslinking precursor X and phospholipid mimetic substance precursor. The reaction time and the concentration in the solvent of the colloidal nanoparticle, the inhibitor crosslinking precursor X, and the phospholipid mimetic substance precursor can also be determined as appropriate in conformity with the desired surface-modified nanoparticles. General methods for tethering on colloidal nanoparticles are known, and, for example, this can be carried out with reference to the methods described in the following Reference Documents A and B.

Reference Documents

A: T. Ohyanagi, et. al., *J. Am. Chem. Soc.* 2011, 133, 12507-12517 (NPL2)

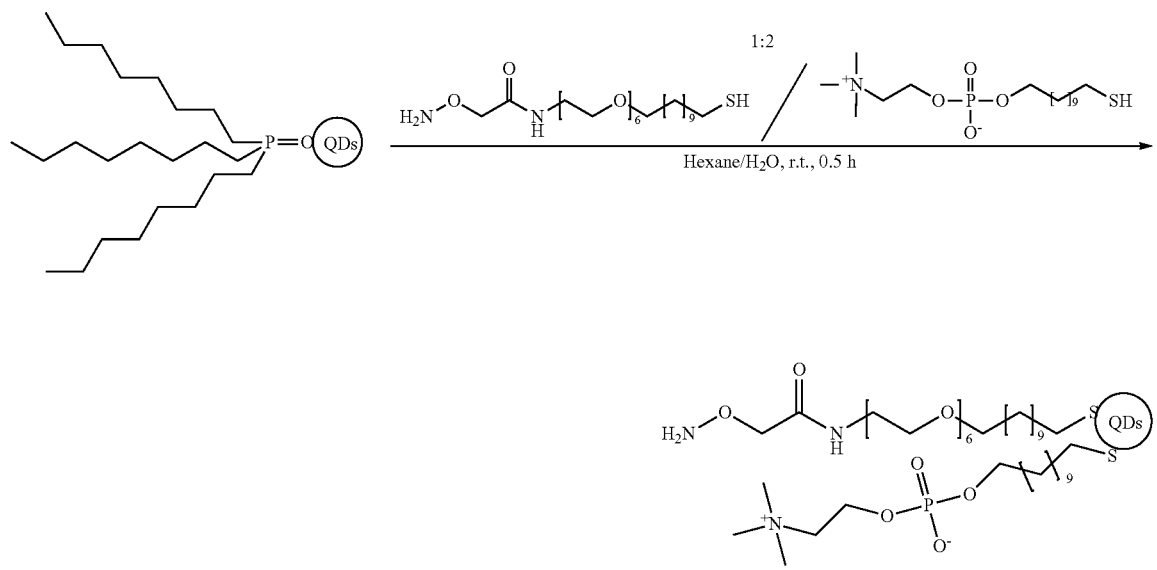

[C31]

The nanoparticle is the same as that described for the conjugate. Colloidal quantum dots (QDs where QD=quantum dot) were used as the starting material for the metal nanoparticle in this scheme. Colloidal quantum dots have protective groups on the surface of a light-emitting semiconductor nanoparticle having a diameter range of, for example, 1 to 20 nm. In the scheme under consideration, the colloidal quantum dot has the trialkylphosphine oxide group on the surface. Colloidal metal nanoparticles may also be used as the starting material when the nanoparticle is a metal nanoparticle. Colloidal quantum dots and colloidal metal nanoparticles are available as commercial products.

The inhibitor crosslinking precursor X represented by general formula (C) and the phospholipid mimetic substance precursor represented by general formula (D) both have the thiol (SH) group as the functional group that will bind to the nanoparticle surface of the colloidal nanoparticle.

The colloidal nanoparticles, inhibitor crosslinking precursor X, and phospholipid mimetic substance precursor are, for example, dispersed in a solvent and two types of phos- B: R. S. Tan, et. al., *ACS Chem. Biol.* 2015, 10, 2073-2086 (NPL3)

Step (2)

Step (2) is a step of obtaining the conjugate of the present invention by mixing the surface-modified nanoparticle obtained in step (1) with a lysosomal enzyme inhibitor precursor Y or a kinase inhibitor precursor Z and bringing about the ligation thereof with the inhibitor crosslinking precursor X to form a lysosomal enzyme inhibitor or kinase inhibitor represented by general formula (A).

Step (2) in Example 1 is illustrated for reference below. The compound 7 synthesized in Example 1 is used as the lysosomal enzyme inhibitor precursor Y.

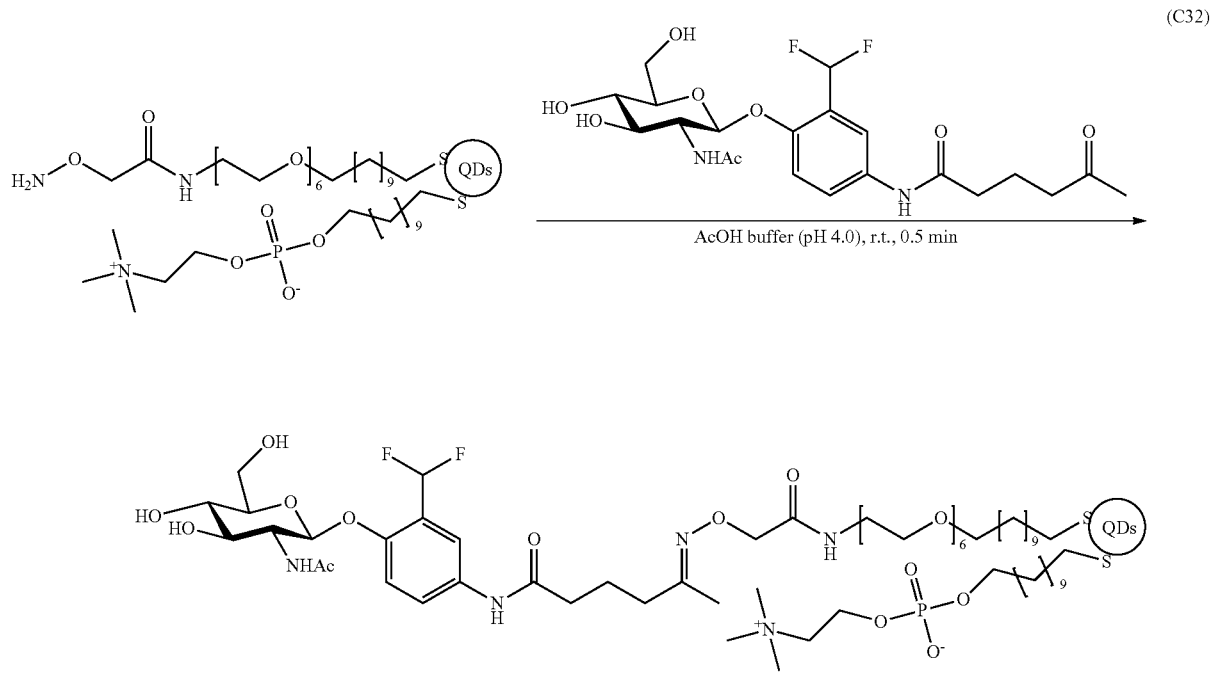

The conjugate of the present invention is obtained by mixing the lysosomal enzyme inhibitor precursor Y with the surface-modified nanoparticle obtained in step (1) and bringing about the ligation thereof with the inhibitor crosslinking precursor X to form the lysosomal enzyme inhibitor represented by general formula (A). The lysosomal enzyme inhibitor precursor Y contains a suicide substrate moiety that contains a group (the reactive group) that exhibits reactivity with an active center of a lysosomal enzyme. Refer to the previous description of this conjugate for the details on the suicide substrate moiety.

Compounds represented by formulas (7), (15), and (20) below are examples of the lysosomal enzyme inhibitor precursor Y. However, this should not be construed as a limitation to these compounds. Compound (7) is used as the lysosomal enzyme inhibitor precursor Y in the scheme given above, and its reaction with the oxyamino group originating with the lysosomal enzyme inhibitor precursor X represented by general formula (C) on the surface of the surface-modified nanoparticle forms the lysosomal enzyme inhibitor represented by general formula (A).

[C33]

(7)

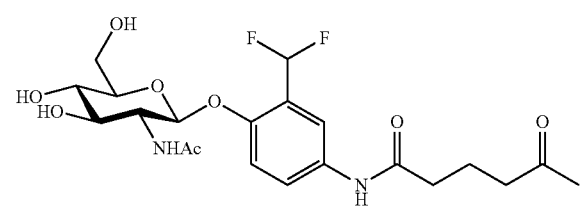

-continued (15)

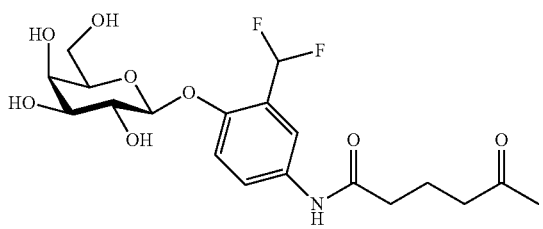

(20)

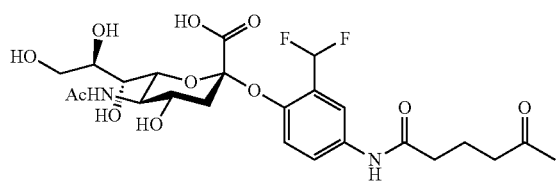

The compounds represented by formulas (7), (15), and (20) and the lysosomal enzyme inhibitor precursors Y corresponding thereto can be prepared, with reference to schemes 1, 3, and 5 in Examples 1 to 3, from known sugar compounds and known starting compounds. The method for condensing the sugar compound with the aryl compound and the method for bonding the side chain to the aryl compound can be carried out with reference to the methods described in T. Ohyanagi et al., J. Am. Chem. Soc. 2011, 133, 12507-12517 (NPL 2). The reaction products can be separated and purified by known methods.

The example of step (2) indicated in B in Example 5 is given below. The compound 32 synthesized in A of Example 5 is used for the kinase inhibitor precursor Z.

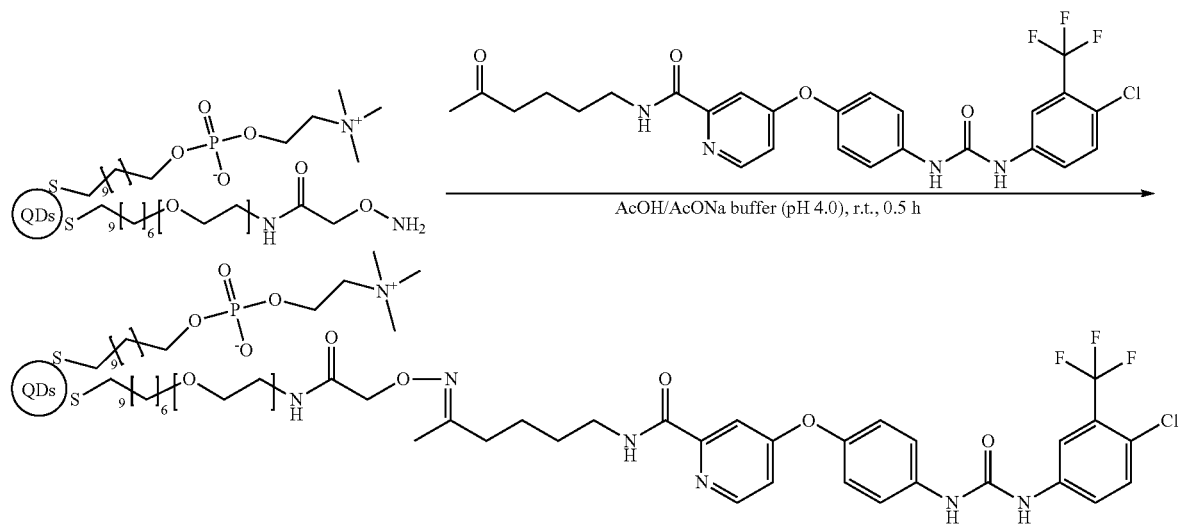

The conjugate of the present invention is obtained by mixing the surface-modified nanoparticle obtained in step (1) with the kinase inhibitor precursor Z and ligating it with the inhibitor crosslinking precursor X to form the kinase inhibitor represented by general formula (A). The kinase inhibitor precursor Z includes the kinase inhibition moiety. Refer to the previous description of this conjugate for the details on the kinase inhibition moiety.

The compound represented by formula (32) below is an example of the kinase inhibitor precursor Z. However, this should not be construed as a limitation thereto. The compound (32) is used as the kinase inhibitor precursor Z in the preceding scheme, and it reacts with the oxyamino group originating with the inhibitor crosslinking precursor X represented by general formula (C) on the surface of the surface-modified nanoparticle to form the kinase inhibitor represented by general formula (A).

[C35]

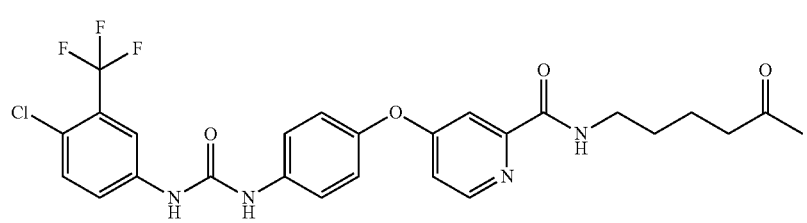

32 conjugate of the lysosomal enzyme inhibitor represented by general formula (A), the reaction conditions, and so forth.

[C36]

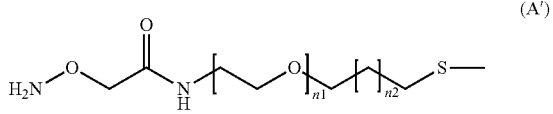

(A')

<The Anticancer Agent>

The present invention encompasses an anticancer agent that contains the above-described conjugate as an active ingredient. The anticancer agent of the present invention is a pharmaceutical composition, containing the above-described conjugate as an active ingredient, for the prevention The compound represented by formula (32) and the corresponding kinase inhibitor precursor Z can be prepared from known starting compounds with reference to the synthesis scheme in Example 5A. The reaction product can be separated and purified by known methods.

The conjugate is formed with the substance that has not reacted with the lysosomal enzyme inhibitor precursor Y or kinase inhibitor precursor Z carried as such on the nanoparticle surface as the substance with general formula (A'). Items such as the amount of use of the lysosomal enzyme inhibitor precursor Y in step (2) are selected as appropriate considering, for example, the type of the lysosomal enzyme inhibitor precursor Y, the desired amount of anchoring on the and/or treatment of cancer (cancer, malignant tumor), and can optionally also contain a pharmaceutically acceptable carrier. This cancer should be a cancer caused by cancer cells for which the efficiency of uptake of the conjugate of the present invention is orders of magnitude higher than in normal cells, but is not otherwise limited. It can be exemplified by breast cancer, prostate cancer, hepatocellular carcinoma, pancreatic cancer, colon cancer, ovarian cancer, renal cancer, lung cancer, and brain tumors. The cancer is preferably breast cancer, hepatocellular carcinoma, pancreatic cancer, or a brain tumor.

Numerous lysosomal enzymes are present in the lysosome, which is an organelle within the cell, and they are responsible for the degradation of substrates within the cell, such as complex carbohydrates and lipids. The lysosomal enzymes include numerous glycan-degrading enzymes. Cells in a high state of activity, such as cancer cells (tumor cells), have an uptake efficiency for the conjugate of the present invention that is orders of magnitude higher than in normal cells, and as a result the conjugate bearing a lysosomal enzyme inhibitor is selectively taken into the high-activity cell and a lysosomal enzyme (for example, a glycan-degrading enzyme) is deactivated. Because the inhibition of lysosomal enzyme activity leads to cell death, a drug having the conjugate of the present invention as an active ingredient is effective as an anticancer agent.

Various enzymes are present within the cell membrane and on the membrane, and kinases, which are a typical example of such enzymes, participate in the phosphorylation of various substances. Cells in a high state of activity, such as cancer cells (tumor cells), have an uptake efficiency for the conjugate of the present invention that is orders of magnitude higher than in normal cells, and as a result the conjugate bearing a kinase inhibitor is selectively taken into the high-activity cell and a kinase deactivation occurs. Because the inhibition of kinase activity leads to cell death, a drug having the conjugate of the present invention as an active ingredient is effective as an anticancer agent.

The anticancer agent of the present invention can be formulated with the conjugate as an active ingredient using methods known to the person having ordinary skill in the art. For example, it can be used via a non-oral route in the form of an injectable agent of a sterile solution or suspension with water or another pharmaceutically acceptable liquid. For example, formulation can be contemplated by combination as appropriate with a pharmacologically acceptable carrier or medium and specifically with sterile water or physiological saline, plant oils, emulsifying agents, suspension agents, surfactants, stabilizers, flavorants, excipients, vehicles, preservatives, binders, etc., and mixing in a unit dosage form as required for generally accepted pharmaceutical practice. The amount of the active ingredients in the formulation is defined for providing an appropriate dose within the designated range.

An aseptic composition for injection can be formulated according to general formulation practice using a vehicle such as distilled water for injection. An aqueous solution for injection can be exemplified by physiological saline or an isotonic solution containing glucose or another adjuvant, for example, D-sorbitol, D-mannose, D-mannitol, sodium chloride, and so forth; and a suitable dissolution adjuvant, e.g., an alcohol and specifically ethanol, a polyalcohol, e.g., propylene glycol and polyethylene glycol, and a nonionic surfactant, e.g., Polysorbate 80 (trade mark) and HCO-60, may also be used in combination therewith.

Sesame oil and soy oil are examples of oils, and benzyl benzoate and benzyl alcohol may be used in combination therewith as a dissolution adjuvant. The following may also be blended: a buffer, e.g., a phosphate salt buffer or sodium acetate buffer; a soothing agent, e.g., procaine hydrochloride; a stabilizer, e.g., benzyl alcohol and phenol; and an antioxidant. The prepared injection solution is generally filled into an appropriate ampule. Liposomes may also be used in order to encapsulate this drug for delivery to the cell.

Administration may be by an oral or non-oral route with non-oral administration being preferred, and specific examples here are injection, nasal administration, inhalation, and transdermal administration. Administration by injection can be exemplified by systemic or local administration by, for example, intravenous injection, intramuscular injection, intraperitoneal injection, subcutaneous injection, and so forth.

The dose and method of administration for the conjugate of the present invention can be selected as appropriate based on the age, body weight, and sex of the patient, the nature and severity of the symptoms to be treated, and so forth. The dose of the pharmaceutical composition containing the present antibody can be selected, for example, from the range from 0.0001 mg to 1,000 mg per 1 kg of body weight per one time. Or, the dose can be selected from the range from 0.01 to 100,000 mg/body per patient, but is not necessarily limited to these numerical values. The dose and method of administration varies with, e.g., the age, body weight, sex, and symptoms of the patient, and can be selected as appropriate by the person having ordinary skill in the art.

EXAMPLES

The present invention is described in additional detail in the following based on examples. However, the examples serve only to exemplify the present invention, and the present invention should not be construed as being limited to or by the examples.

Example 1: N-Acetylglucosaminase Inhibitor-Bearing Nanoparticles (1) Synthesis of Compound 7

[C37]

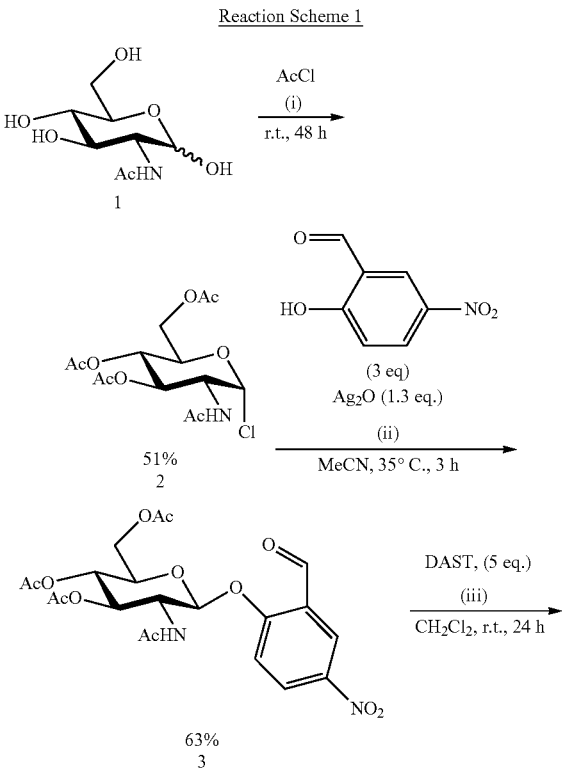

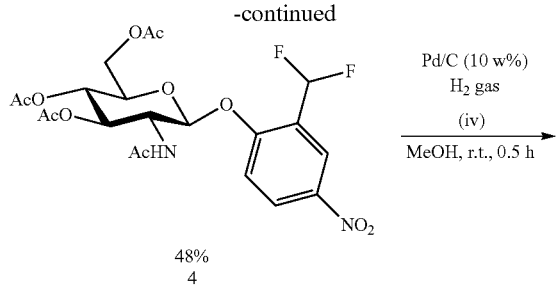

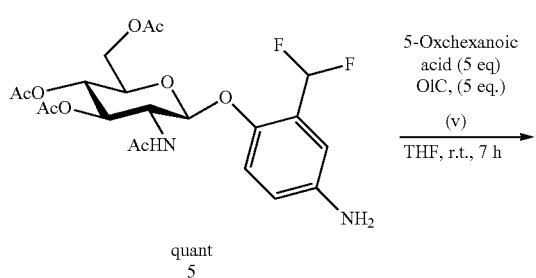

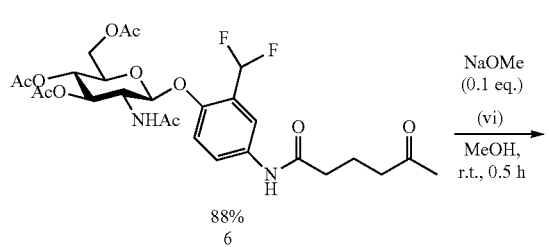

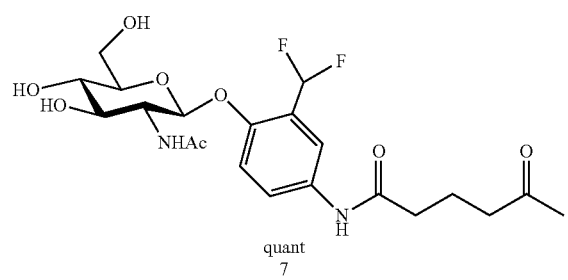

Synthesis route to compound 7: (i) AcCl (20 eq.), r.t., 48 h, 68%, (ii) 5-nitrosalicylaldehyde (3 eq.), Ag$_2$O (1.3 eq.), MeCN, 35° C., 53%, (iii) DAST (5 eq.), CH$_2$Cl$_2$, r.t., 24 h, 48%, (iv) Pd/C (10 wt %), H$_2$ gas, r.t., 0.5 h, quant, (v) 5-oxohexanoic acid (5 eq.), DIC (5 eq.), THF, r.t., 7 h, 88%, (vi) NaOMe (0.1 eq.), MeOH, r.t., 0.5 h, quant.

Compound 7 was synthesized using N-acetyl-D-glucosamine as the starting material. Compound 3 was obtained with β-selectivity by the glycosylation reaction of 5-nitrosalicylaldehyde with the reactive sugar donor 2, and this was followed by conversion to compound 4 by conversion of the aldehyde group in 3 to the difluoromethyl group using diethylamino sulfur trifluoride (DAST). 5 was then obtained by reduction of the nitro group in compound 4; compound 6 was derived by the condensation of 5 with 5-oxohexanoic acid in the presence of N,N'-diisopropylcarbodiimide (DIC); and the target compound 7 indicated below was efficiently prepared by deacetylation.

[C38]

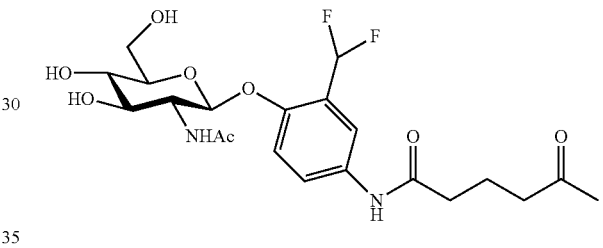

Structural information for compound 7: $^1$H NMR (500 Hz, D$_2$O) δ ppm 1.82 (m, 2H, —CH$_2$—CH$_2$—CH$_2$—), 1.97 (s, 3H, —CO—CH$_3$), 2.1 (s, 3H, NHAc), 2.32 (t, 2H, —CH$_2$—CO—CH$_3$), 2.56 (t, 2H, —NH—CO—CH$_2$—), 3.47 (t, 1H, H-4), 3.56 (m, 2H, H-3, H-5), 3.71 (m, 1H, H-6), 3.9 (m, 2H, H-2, H-6), 5.04 (d, 1H, H-1), 6.79 (t, 1H, CHF$_2$), 7.18 (d, 1H, H-arom), 7.41 (d, 1H, H-arom), 7.52 (s, 1H, H-arom); ESI-MS 497.103 [M+Na]$^+$ (2) Construction of Fluorescent Nanoparticles Displaying Compound 7

The procedure for constructing fluorescent nanoparticles (quantum dots) displaying compound 7 is given in the following reaction scheme 2.

[C39]

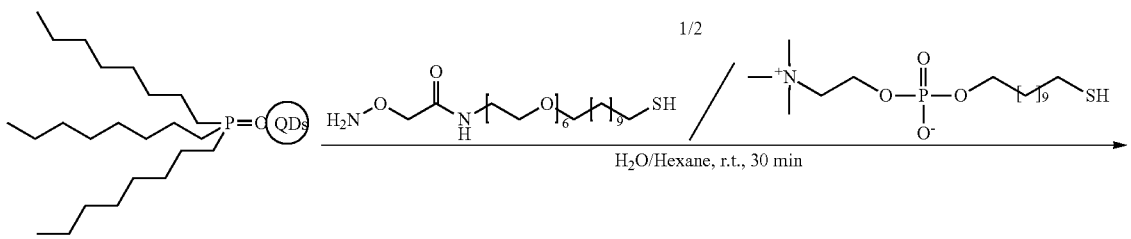

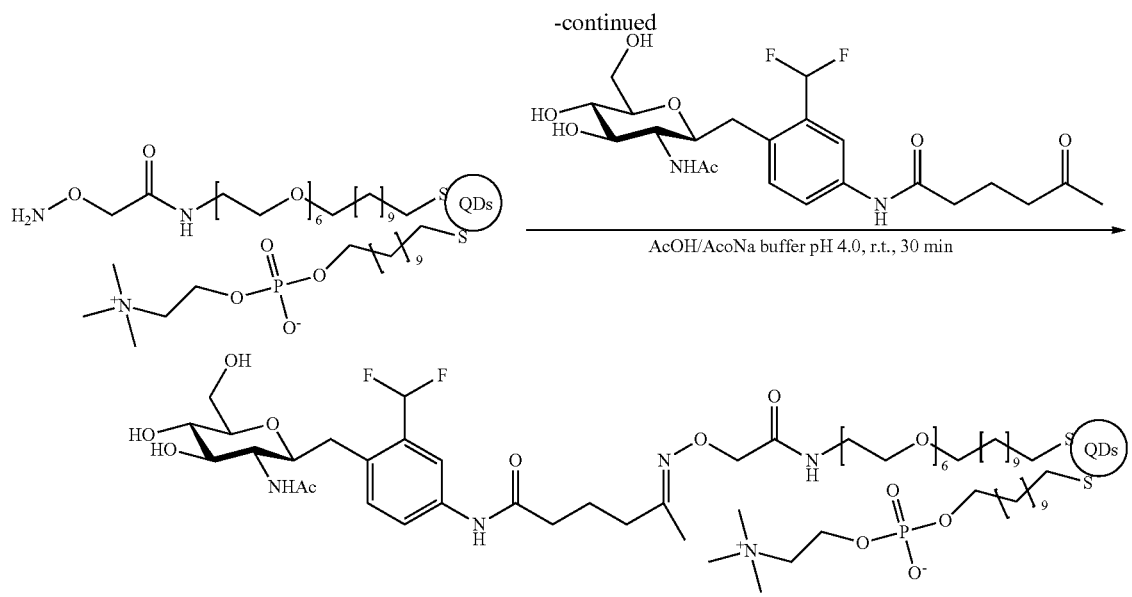

Compound 7 was displayed (anchored) on fluorescent nanoparticles (quantum dots, Invitrogen Qdot (registered trademark) 655) according to the methods described in Reference Documents 2 and 3.

Preparation of the reactive nanoparticle precursor AO/PC SAM-QDs (AO/PC=1/2): MeOH (50 μL) and i-PrOH (100 μL) were added to TOPO-QDs (1 μM, 50 μL/octane) and the nanoparticles were pelleted by centrifugation followed by removal of the solvent and redispersion by the addition of hexane (50 μL). The aminooxy linker (10 mM, 10 μL/MeOH), which had been preliminarily activated by deprotection, the phosphorylcholine linker (100 mM, 4 μL/MeOH), NaBH$_4$ (1 μL, 12 wt % in 14 N NaOH), and MilliQ (50 μL) were then added and stirring was carried out for 30 minutes to conduct ligand exchange and produce the reactive nanoparticle precursor AO/PC SAM-QDs (AO/PC=1/2). This was purified by ultrafiltration (YM 50) and submitted to reaction with compound 7.

Display of compound 7 on the nanoparticle: The AO/PC SAM-QDs (AO/PC=1/2) and compound 7 (30 mM, 10 μL/MilliQ) were dispersed in AcOH/AcONa buffer (pH 4, 100 μL); stirring was carried out for 30 minutes at room temperature; and purification by ultrafiltration (YM 50) was performed to obtain the target substance. It was confirmed by MALDI-TOFMS that compound 7, which is a suicide substrate moiety, was displayed on the nanoparticle surface (FIG. 1).

(3) Antitumor Effect (1) of the Fluorescent Nanoparticles Displaying the Lysosomal Enzyme Inhibitor (7) (Inhibitory Effect on Breast Cancer Cell Proliferation)

Intracellular imaging: Human breast cancer cells (MCF-7, P13, acquired from ATCC) were seeded at 5000 cell/200 μL/well and were incubated for 48 hours on D-MEM high glucose and 10% fetal bovine serum (FBS) under conditions of 37° C. and 5% CO$_2$. The fluorescent nanoparticles displaying compound 7 [10 nM compound 7-bearing AO/PC SAM-QDs (AO/PC=1/2)] or AO/PC SAM-QDs (AO/PC=1/2) as the comparative substance were then added and the cell growth process was monitored for 8 hours after this. Observation with a fluorescence microscope was performed after the cells had been stained by the following procedure. After removal of the medium, the cells were washed 3 times with Opti-MEM; LysoTracker R Green DND-26 (200 μL, 5 nM/Opti-MEM) was subsequently added; and lysosome staining was performed by incubation for 30 minutes under conditions of 37° C. and 5% CO$_2$. Nuclear staining was then performed by the addition of Hoechst (2 μL, 0.1 ng/L/Opti-MEM) and additional incubation for 15 minutes under conditions of 37° C. and 5% CO$_2$, followed by washing 3 times with Opti-MEM and imaging (FIG. 2).

Figure 2A:
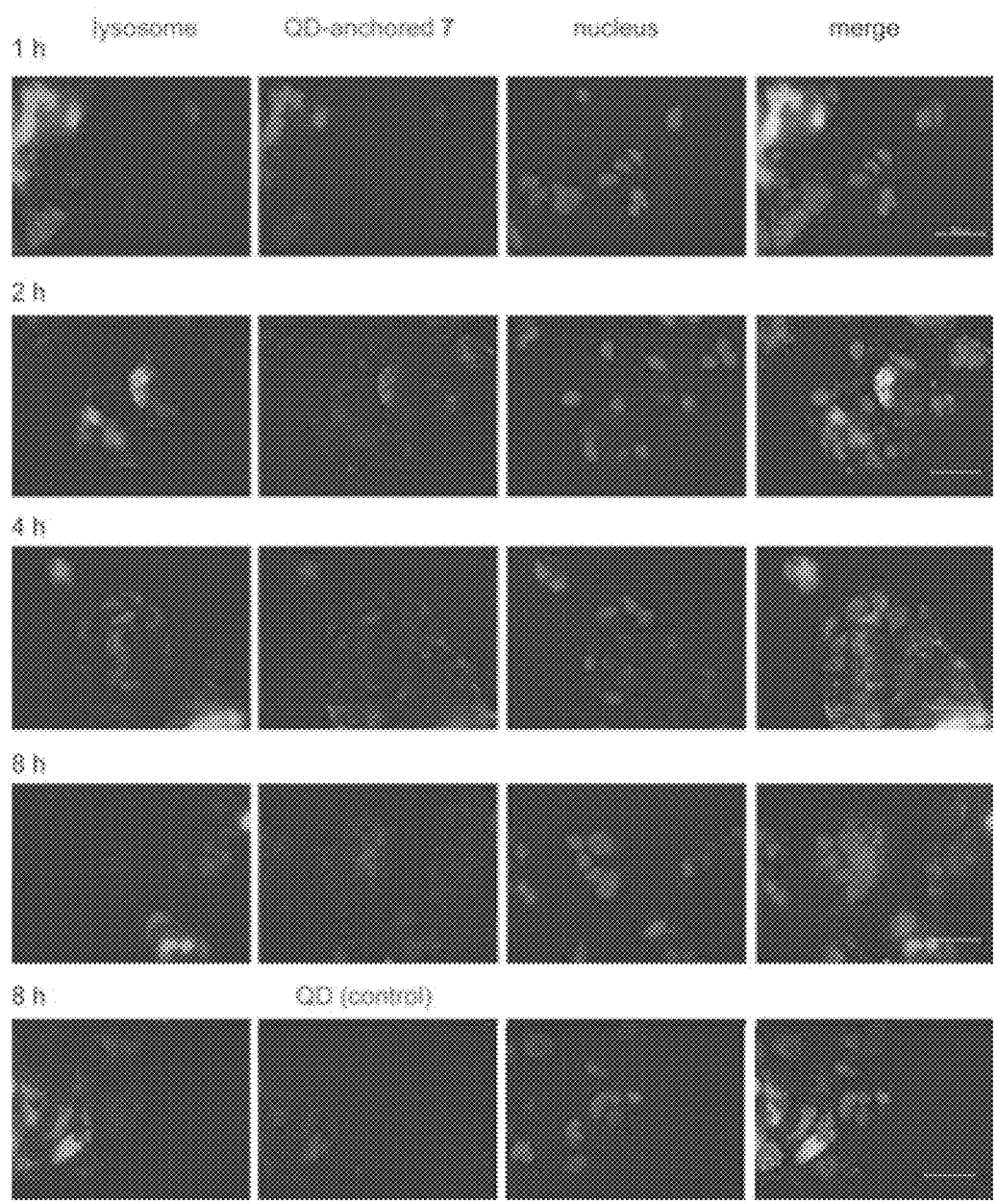
FIG. 2a shows the intracellular behavior in cancer cells of fluorescent nanoparticles that display compound 7 (10 nM). (a) Intracellular trafficking of fluorescent nanoparticles after the start (1 to 8 hours) of breast cancer cell (MCF7) culture (scale bar size=50 μm).
Figure 2B:
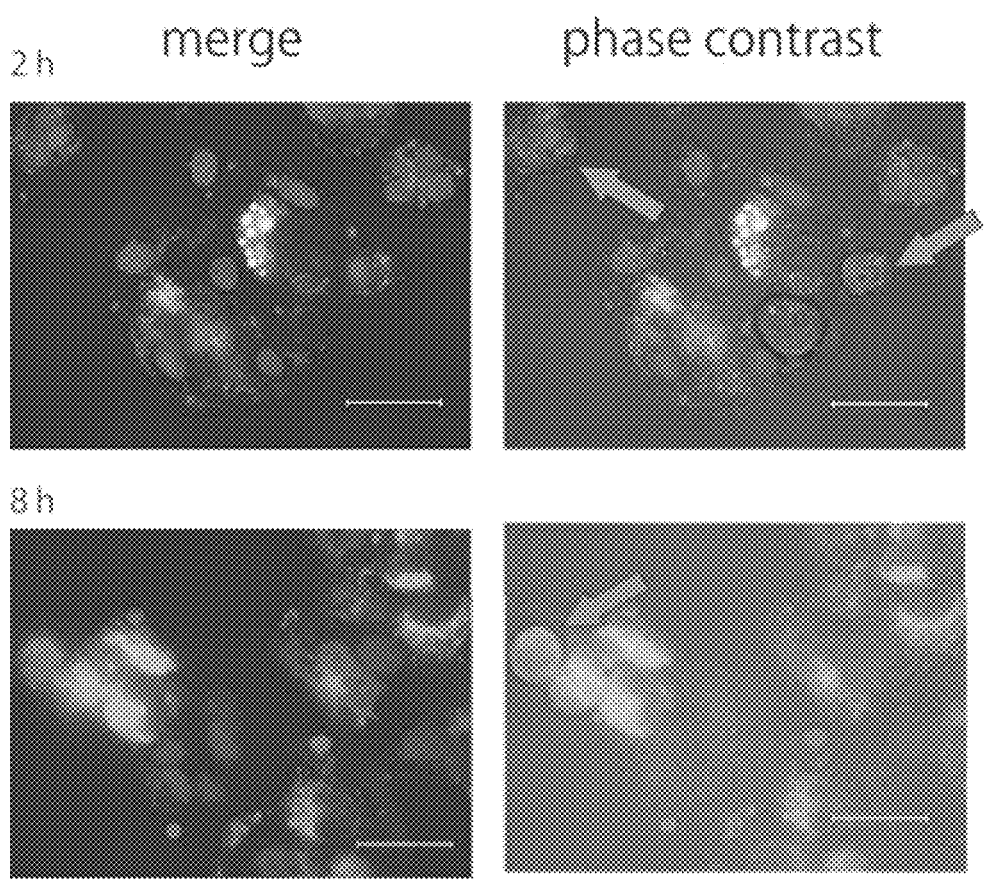
FIG. 2b shows the intracellular behavior in cancer cells of fluorescent nanoparticles that display compound 7 (10 nM). (b) Status of the intracellular distribution of QD-anchored inhibitor 7 (fluorescent nanoparticles carrying compound 7) at 2 hours (upper) and 8 hours (lower) after the start of culture (scale bar size=50 μm). Enlarged view (left) and phase contrast image (right).
Figure 4:
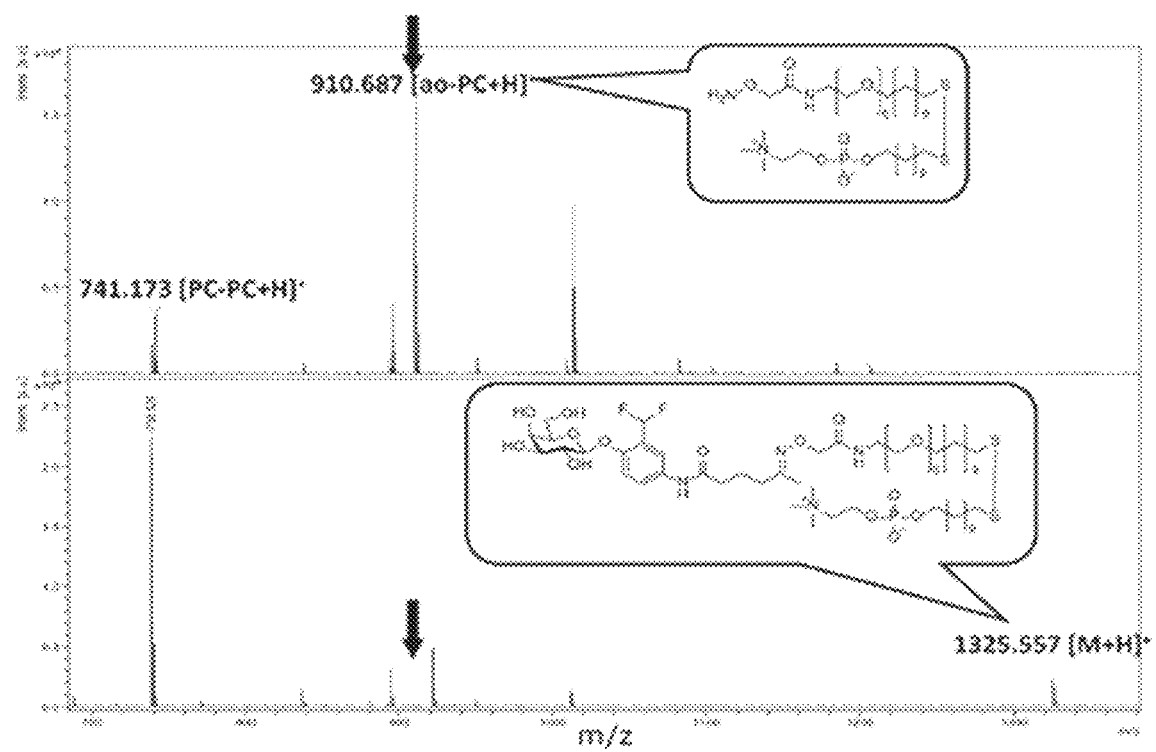
FIG. 4 confirms by MALDI-TOFMS the display of a compound in Example 2 on the nanoparticle surface.
Figure 8:
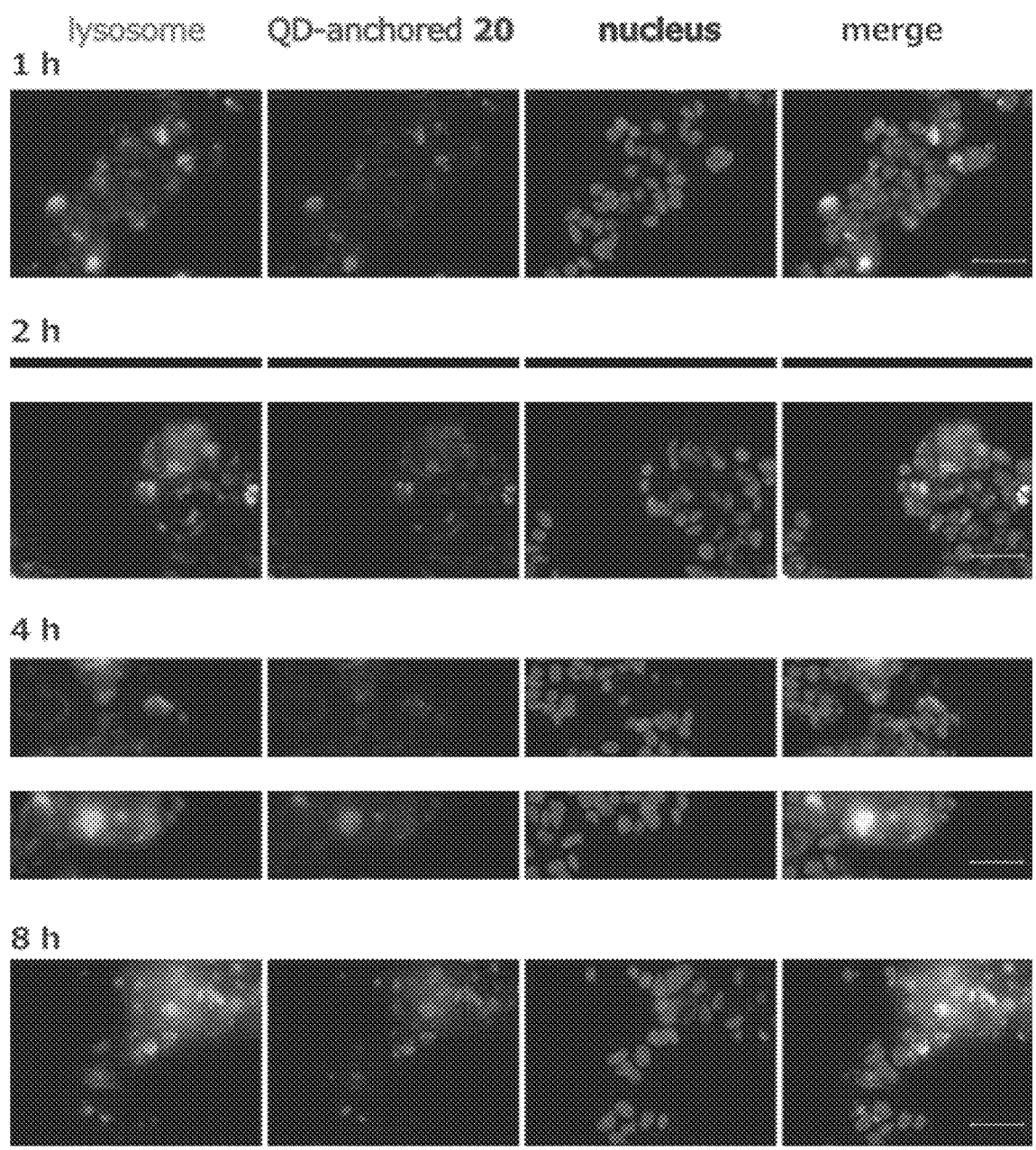
FIG. 8 shows the intracellular behavior in cancer cells of fluorescent nanoparticles that display compound 20 (10 nM): intracellular trafficking of fluorescent nanoparticles after the start (1 to 8 hours) of breast cancer cell (MCF-7) culture (scale bar size=50 μm).

It was observed that the fluorescent nanoparticles displaying compound 7 were rapidly taken into the breast cancer cells and were present in the lysosomes after 1 hour (FIG. 2a, 1 h) and that the nanoparticles had already escaped from the lysosomes after 2 hours (FIG. 2a, 2 h). At 4 to 8 hours, most of the nanoparticles are present dispersed within the cell (FIG. 2a, 4 h and 8 h). After 4 to 8 hours, the reduction in the region stained by the LysoTracker R Green DND-26 was substantial. On the other hand, with the fluorescent nanoparticles not bearing compound 7 (QD control) that were used for comparison, even after the elapse of 8 hours almost all remained trapped within the lysosomes (FIG. 2a, 8 h, lowermost). In addition, lysosomes were almost undetected in floating dead cells seen occasionally in FIG. 2b (2 and 8 hours after the start of culture).

(4) Antitumor Effect (2) of the Fluorescent Nanoparticles Displaying the Lysosomal Enzyme Inhibitor (7) (Breast Cancer Cell Killing Action)

Quantitation of dead cells by the MTA assay: MCF7 cells (5×10$^3$/100 μL/well) were incubated for 24 hours in a 37° C. and 5% CO$_2$ atmosphere, and QD-anchored inhibitor 7 (1 μM, 10±L/MilliQ), QD control (1 μM, 10 μL/MilliQ), compound 7 (1 μM, 10 μL/MilliQ), and cisplatin (1 mM, 10 μL/MilliQ) were then respectively added per 90 μL of the medium and the final concentration was adjusted to 100 nM (but 100 μM for the cisplatin). At 96 hours after the start of culture, washing was performed 3 times with the medium component and 10 μL of the cell culture medium was recovered. Cell Counting Kit-8 solution (Dojindo, Kumamoto, Japan) was added; incubation was carried out for 1.5 hours in a 37° C. and 5% CO$_2$ atmosphere; and the viable cell percentage was quantitated by measurement of the absorbance at 450 nm.

FIG. 3 gives the results for the breast cancer cell killing action of the fluorescent nanoparticles displaying compound 7 (100 nM QD-anchored 7). (a) The percentage viability for the MCF7 cells was quantitated by the MTA method after coculture for 96 hours in the presence of the fluorescent nanoparticles displaying compound 7 or in the presence of the individual test agents used for comparison. (b) Status of the breast cancer cells after coculture for 96 hours with each test agent (scale bar size=50 μm). The lysosomes are stained green and the nuclei are stained blue and the QDs exhibit a red fluorescence. (c) Behavior within the cancer cells of the compound 7-bearing fluorescent nanoparticles (10 nM): status of the intracellular distribution of the fluorescent nanoparticles as visualized by Z stack at 8 hours after the start of culture of the breast cancer cells (MCF7) (scale bar size=50 μm).

Figure 3A:
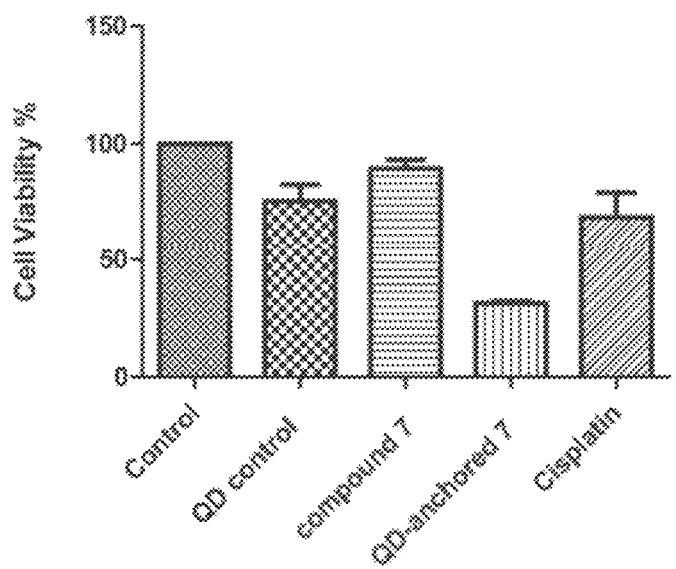
FIG. 3a shows the results for the breast cancer cell killing action of fluorescent nanoparticles that display compound 7 (100 nM QD-anchored 7). (a) The viability of MCF7 cells was quantitated by the MTA method after coculture for 96 hours with fluorescent nanoparticles displaying compound 7 or the individual test agents used for comparison.
Figure 3B:
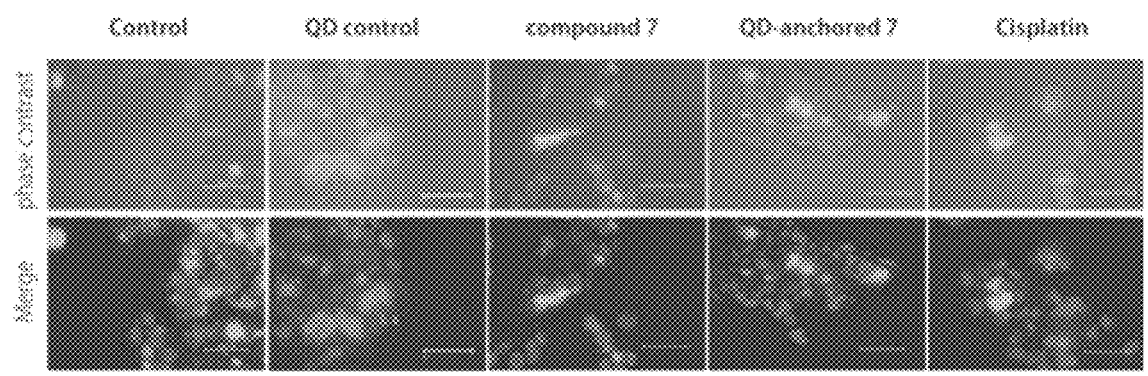
FIG. 3b shows the results for the breast cancer cell killing action of fluorescent nanoparticles that display compound 7 (100 nM QD-anchored 7). (b) Status of breast cancer cells after coculture for 96 hours with the particular test agent (scale bar size=50 μm). Lysosomes are stained green; nuclei are stained blue; and QDs display a red fluorescence.
Figure 3C:
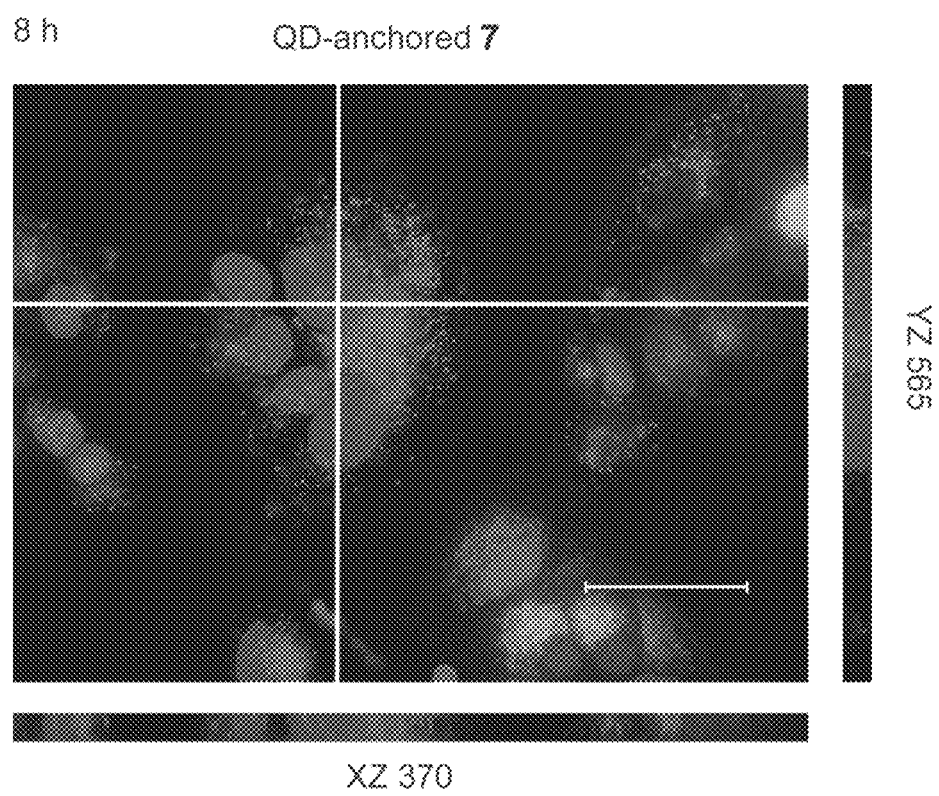
FIG. 3c shows the results for the breast cancer cell killing action of fluorescent nanoparticles that display compound 7 (100 nM QD-anchored 7). (c) Behavior of fluorescent nanoparticles that display compound 7 (10 nM) in cancer cells: the status of the intracellular distribution of the fluorescent nanoparticles as visualized by Z stack at 8 hours after the start of culture of breast cancer cells (MCF7) (scale bar size=50 μm).

The fluorescent nanoparticles displaying compound 7 (100 nM QD-anchored 7) significantly stopped the growth of MCF7 breast cancer cells and, at a viability of approximately 30% after coculture for 96 hours, exhibited a strong anticancer action far beyond that of 100 μM cisplatin (1000-times the dose of the 100 nM QD-anchored 7) (FIG. 3a). In addition, floating dead cells with altered shapes were observed only in the experimental systems seeded with 100 nM QD-anchored 7 or 100 μM cisplatin (FIG. 3b). Uptake of the fluorescent nanoparticles displaying compound 7 into the cells is shown in FIG. 3c.

(4) Antitumor Effect (3) of the Fluorescent Nanoparticles Displaying the Lysosomal Enzyme Inhibitor (7)

Imaging using GFP-expressing cells: human breast cancer cells (MCF-7, P17, acquired from ATCC) were seeded at 5000 cell/200 μL/well and were incubated for 24 hours on D-MEM high glucose and 10% fetal bovine serum (FBS) in a 37° C. and 5% $CO_2$ atmosphere. This was followed by the addition of CellLight (trade mark) Lysosomes-GFP*BacMam 2.0*(1 μL 5000 cell/μL/medium) and incubation for an additional 24 hours to induce expression of GFP on the lysosome surface. The fluorescent nanoparticles displaying compound 7 [10 nM compound 7-bearing AO/PC SAM-QDs (AO/PC=1/2)] or AO/PC SAM-QDs (AO/PC=1/2) as the comparative substance were then added and the cell growth process was monitored for 8 hours after this. Observation with a fluorescence microscope was performed after the cells had been stained by the following procedure. After removal of the medium, the cells were washed 3 times with Opti-MEM and nuclear staining was then performed by the addition of Hoechest (200 μL, 0.001 ng/μL/Opti-MEM) and incubation for 15 minutes in a 37° C. and 5% $CO_2$ atmosphere, followed by washing 3 times with Opti-MEM and imaging (FIG. 3d).

Figure 3D:
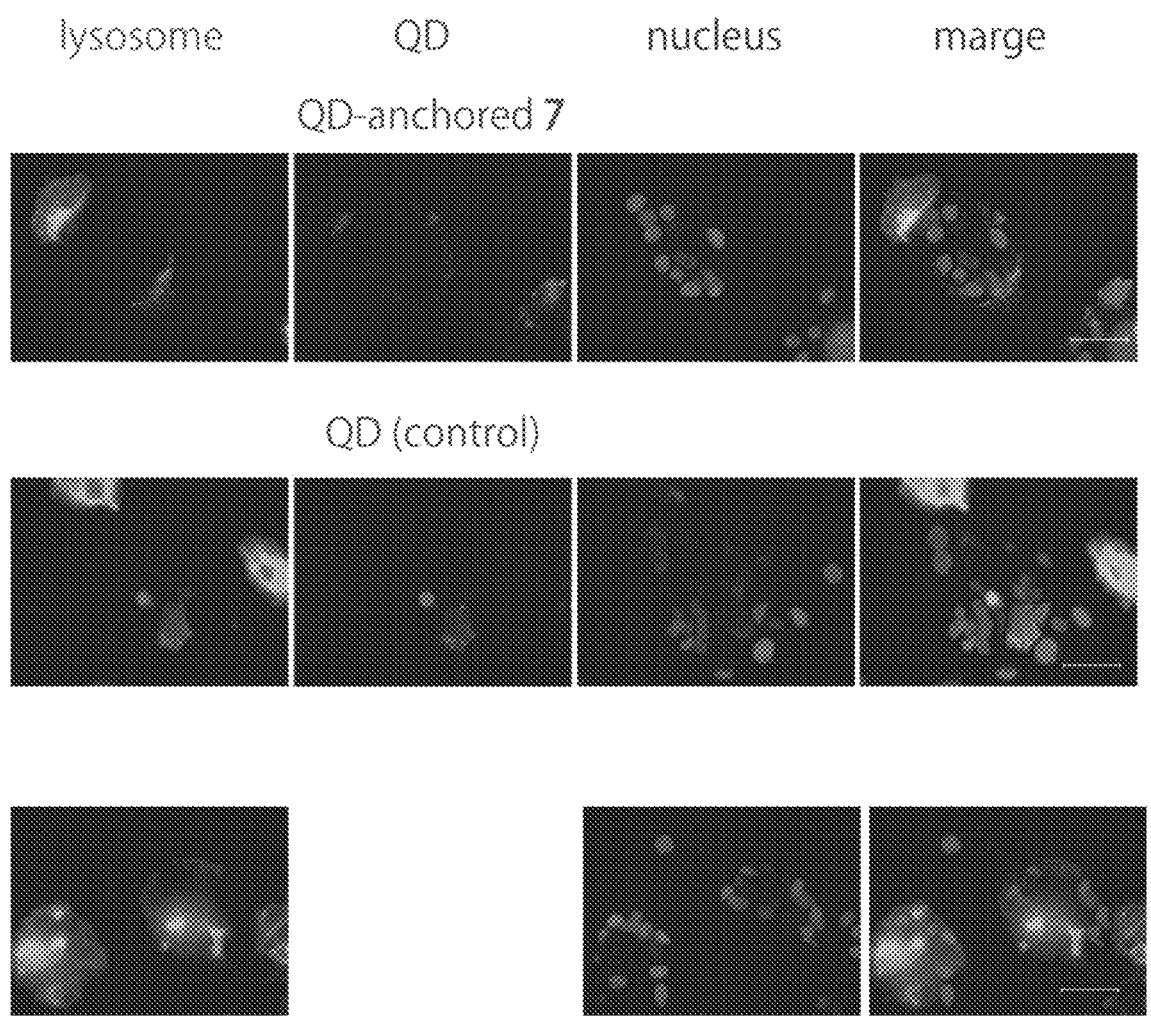
FIG. 3d shows the results for the breast cancer cell killing action of fluorescent nanoparticles that display compound 7 (100 nM QD-anchored 7). (d) Live cell imaging using a GFP-expressing cell line: intracellular behavior of the fluorescent nanoparticles at 8 hours after the start of culture of breast cancer cells (MCF-7) (scale bar size=50 μm).

Based on the results in FIG. 3d, it is inferred that the NAG suicide substrate-displaying nanoparticles escaped from the lysosomes by permeation or disruption of the lysosome membrane by the formation of a covalent bond with the NAG present in the lysosome.

Reference Documents

1. M. Ichikawa et al. *Bioorg. Med. Chem. Lett.* 2001, 11, 1769-1773
2. T. Ohyanagi et al., *J. Am. Chem. Soc.* 2011, 133, 12507-12517
3. R. S. Tan et al., *ACS Chem. Biol.* 2015, 10, 2073-2086

Example 2: Galactosidase Inhibitor-Bearing Nanoparticles (1) Synthesis of Compound 15

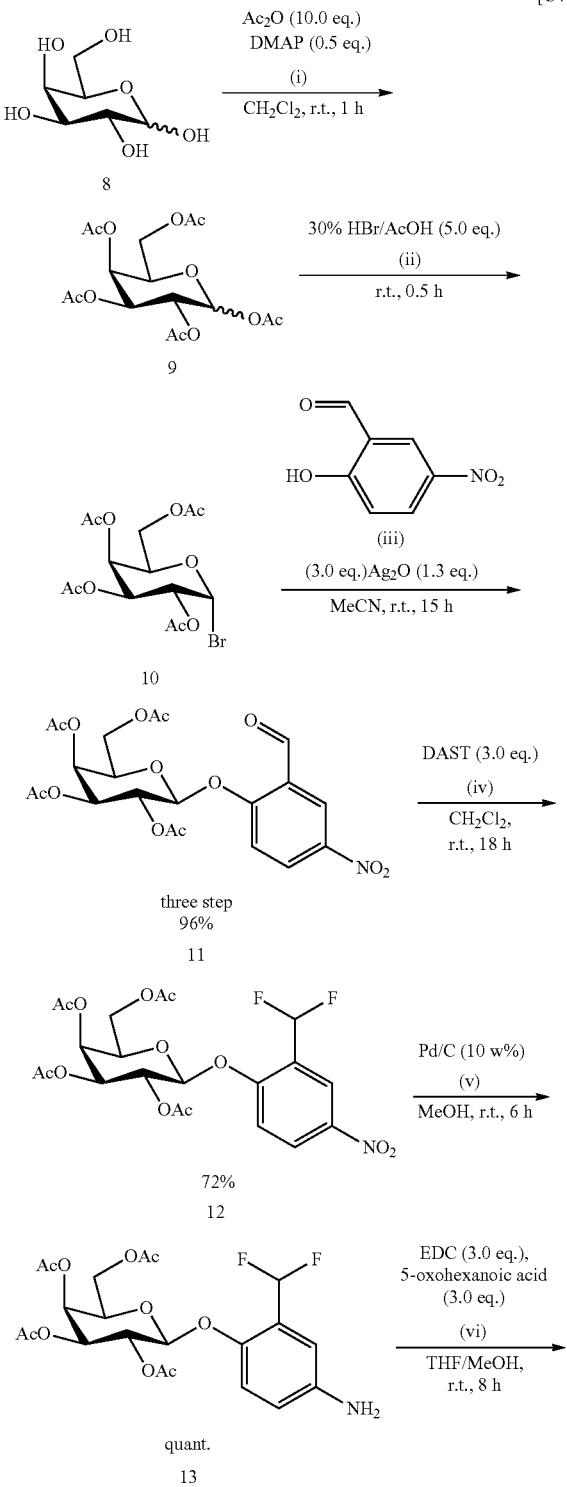

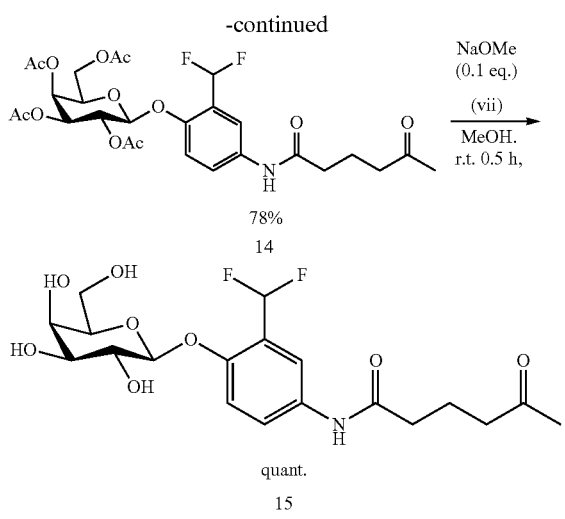

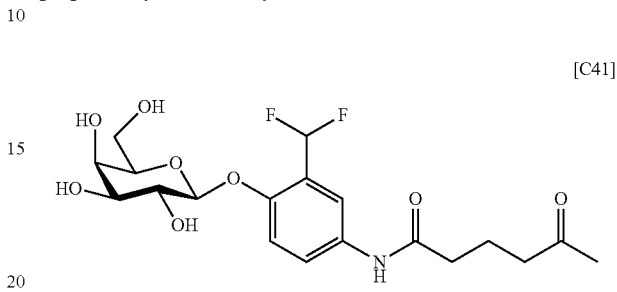

Synthesis route to compound 15: (i) Ac$_2$O (10 eq.), r.t., 48 h, (ii) 30% HBr/AcOH (5.0 eq.), r.t., 0.5 h, (iii) 5-nitrosalicylaldehyde (3 eq.), Ag$_2$O (1.3 eq.), MeCN, r.t., three step yield 96%, (iv) DAST (3 eq.), CH$_2$Cl$_2$, r.t., 18 h, 72%, (v) Pd/C (10 wt %), H$_2$ gas, r.t., 6 h, quant, (vi) 5-oxohexanoic acid (3 eq.), EDC (3 eq.), MeOH, r.t., 8 h, 78%, (vii) NaOMe (0.1 eq.), MeOH, r.t., 0.5 h, quant.

Compound 15, which is a precursor for the suicide substrate moiety, was synthesized with reference to document 1 using galactose as the starting material. Compound 11 was selectively obtained by the glycosylation reaction of 5-nitrosalicylaldehyde with the reactive sugar donor 10, and this was followed by conversion to compound 12 by conversion of the aldehyde group in 11 to the difluoromethyl group using diethylamino sulfur trifluoride (DAST). 13 was then obtained by reduction of the nitro group in compound 12; compound 14 was derived by the condensation of 13 with 5-oxohexanoic acid in the presence of 1-ethyl-3-(3-dimethylaminopropyl)carbodiimide hydrochloride (EDC); and the target compound 15 indicated below was efficiently prepared by the deacetylation reaction.

Structural information for compound 15: $^1$H NMR (500 Hz, D$_2$O) δ ppm 1.81 (m, 2H, —CH$_2$—CH$_2$—CH$_2$—), 2.09 (s, 3H, —CO—CH$_3$), 2.31 (t, 2H, —CH$_2$—CO—CH$_3$—), 2.55 (t, 2H, —NH—CO—CH$_2$—), 3.67 (m, 3H, H-3, H-5, H-6), 3.74 (m, 2H, H-2, H-6), 3.90 (d, 1H, H-4), 4.97 (d, 1H, H-1), 7.02 (t, 1H, CHF$_2$), 7.19 (d, 1H, H-arom), 7.4 (d, 1H, H-arom), 7.54 (s, 1H, H-arom); ESI-MS 456.130 [M+Na]$^+$ (2) Construction of Fluorescent Nanoparticles Displaying Compound 15

The procedure for constructing fluorescent nanoparticles (quantum dots) displaying compound 15 is given in the following reaction scheme 4.

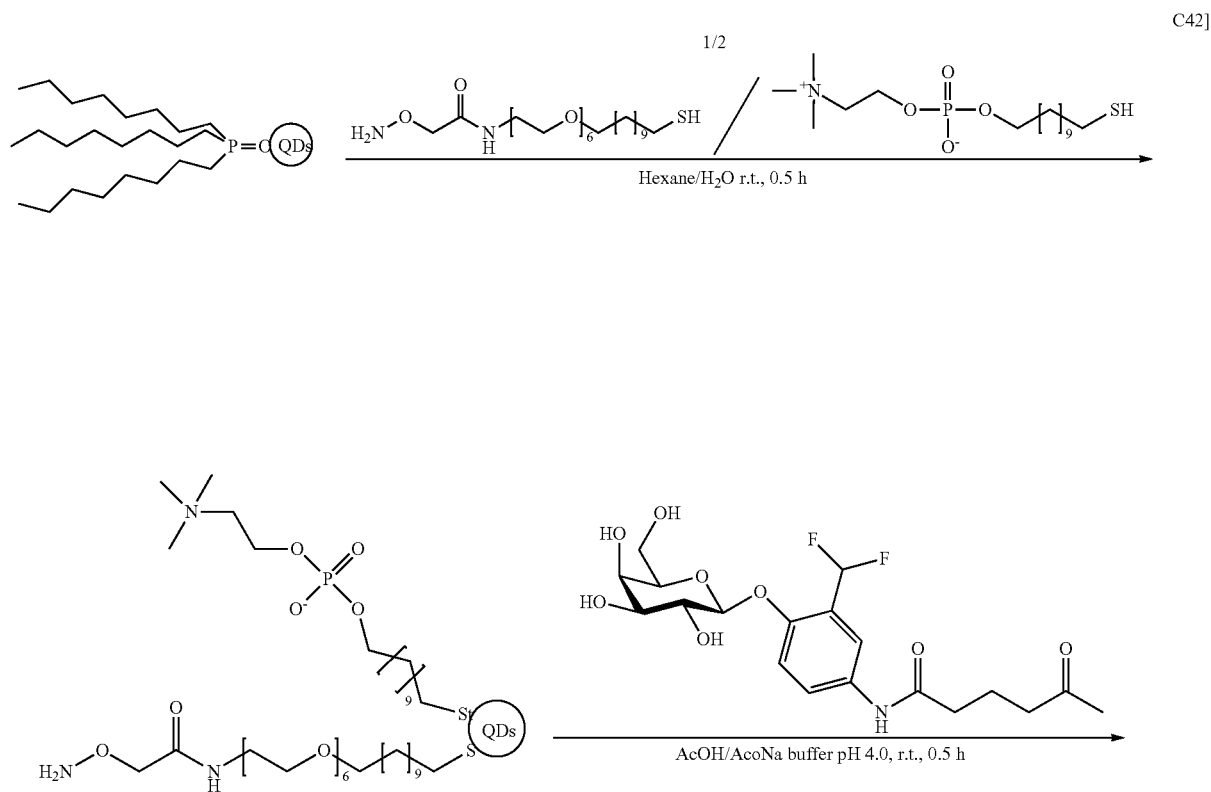

-continued

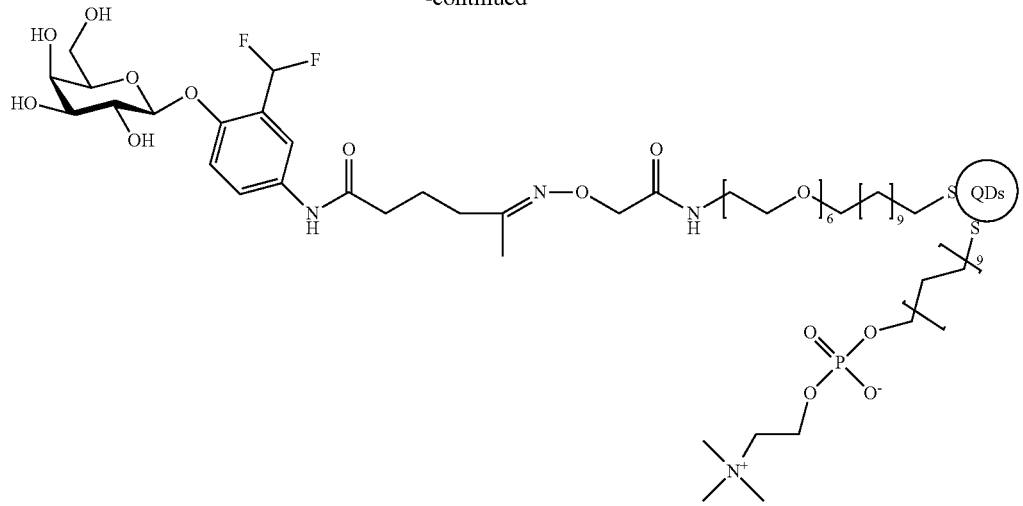

Compound 15 was displayed on fluorescent nanoparticles (quantum dots, Invitrogen Qdot (registered trademark) 655) according to the methods described in Reference Documents 2 and 3.

Preparation of the reactive nanoparticle precursor AO/PC SAM-QDs (AO/PC=1/2): MeOH (50 µL) and i-PrOH (100 µL) were added to TOPO-QDs (1 µM, 50 µL/octane) and the nanoparticles were pelleted by centrifugation followed by removal of the solvent and redispersion by the addition of hexane (50 µL). The aminooxy linker (10 mM, 10±L/MeOH), which had been preliminarily activated by deprotection, the phosphorylcholine linker (100 mM, 4 µL/MeOH), NaBH$_4$ (1 µL, 12 wt % in 14 N NaOH), and MilliQ (50 µL) were then added and stirring was carried out for 30 minutes to conduct ligand exchange and produce the reactive nanoparticle precursor AO/PC SAM-QDs (AO/PC=1/2). This was purified by ultrafiltration (YM 50) and submitted to reaction with compound 15.

Display of compound 15 on the nanoparticle: The AO/PC SAM-QDs (AO/PC=1/2) and compound 15 (30 mM, 10 µL/MilliQ) were dispersed in AcOH/AcONa buffer (pH 4, 100 µL); stirring was carried out for 30 minutes at room temperature; and purification by ultrafiltration (YM 50) was performed to obtain the target substance. It was confirmed by MALDI-TOFMS that compound 15, which is a suicide substrate moiety, was displayed on the nanoparticle surface (FIG. 4).

(3) Antitumor Effect (1) of the Fluorescent Nanoparticles Displaying Compound 15 (Inhibitory Effect on Breast Cancer Cell Proliferation)

Figure 5:
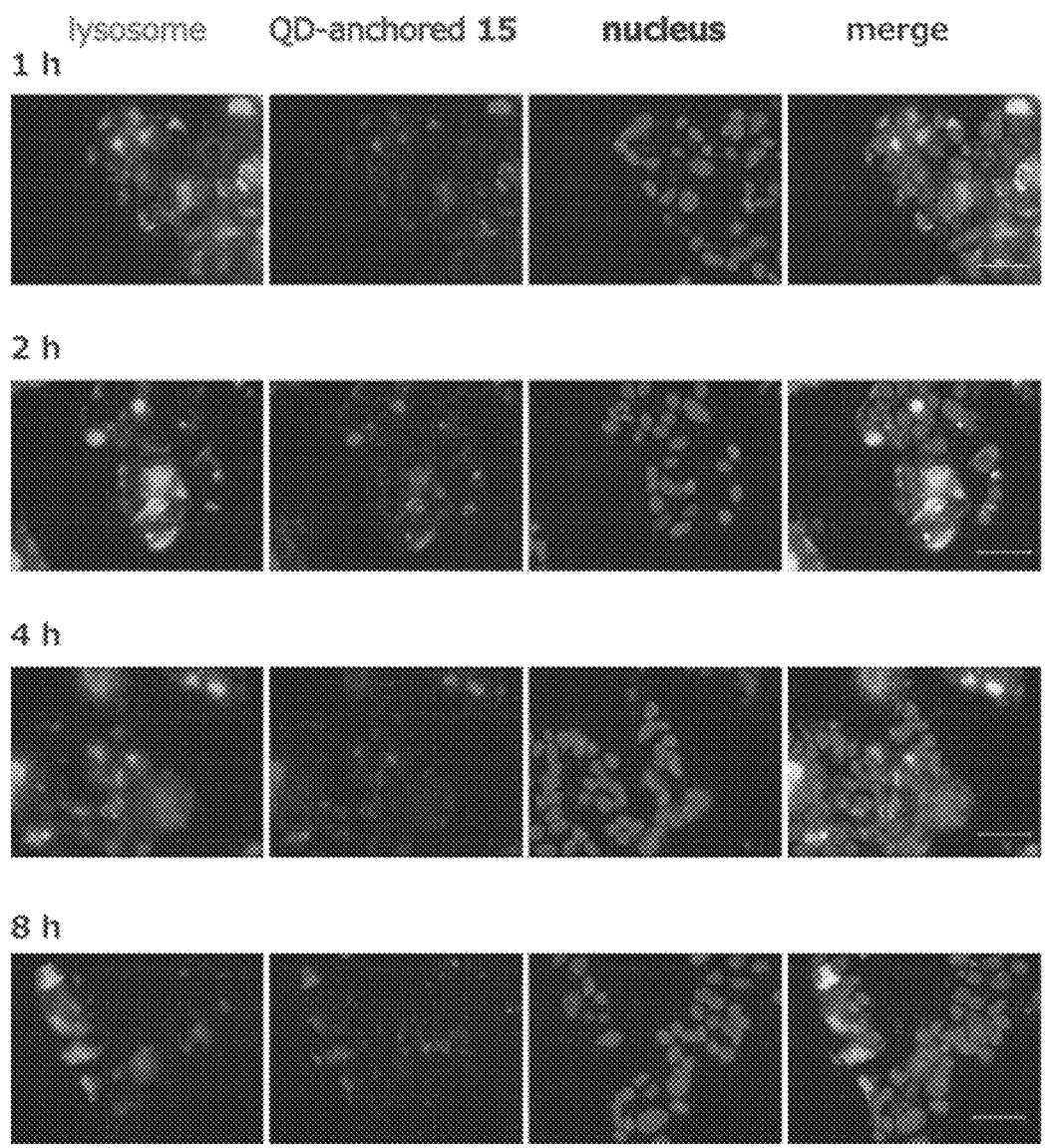
FIG. 5 shows the intracellular behavior a in cancer cells of fluorescent nanoparticles that display compound 15 (10 nM). Intracellular trafficking of fluorescent nanoparticles after the start (1 to 8 hours) of breast cancer cell (MCF-7) culture (scale bar size=50 μm).

Intracellular imaging: human breast cancer cells (MCF-7, P17, acquired from ATCC) were seeded at 5000 cell/200 µL/well and were incubated for 48 hours on D-MEM high glucose and 10% fetal bovine serum (FBS) in an atmosphere of 37° C. and 5% CO$_2$. The fluorescent nanoparticles displaying compound 15 [10 nM compound 15-bearing AO/PC SAM-QDs (AO/PC=1/2)] were then added and the cell growth process was monitored for 8 hours after this. Observation with a fluorescence microscope was performed after the cells had been stained by the following procedure. After removal of the medium, the cells were washed 3 times with Opti-MEM; LysoTracker R Green DND-26 (200 µL, 5 nM/Opti-MEM) was subsequently added; and lysosome staining was performed by incubation for 30 minutes under conditions of 37° C. and 5% CO$_2$. Nuclear staining was then performed by the addition of Hoechest (2 µL, 0.1 ng/µL/Opti-MEM) and additional incubation for 15 minutes in an atmosphere of 37° C. and 5% CO$_2$, followed by washing 3 times with Opti-MEM and imaging (FIG. 5). FIG. 5 shows the intracellular behavior in cancer cells of fluorescent nanoparticles that display compound 15 (10 nM): intracellular trafficking of fluorescent nanoparticles after the start (1 to 8 hours) of breast cancer cell (MCF-7) culture (scale bar size=50 µm). Uptake into the cells of the fluorescent nanoparticles displaying compound 15 is demonstrated by FIG. 5.

(4) Antitumor Effect (2) of the Fluorescent Nanoparticles Displaying Compound 15 (Breast Cancer Cell Killing Action)

Quantitation of dead cells by the MTT assay: MCF-7 cells ($5\times10^4$/100 mL/well) were incubated for 24 hours in a 37° C. and 5% CO$_2$ atmosphere, and QD-anchored inhibitor 15 (1 µM, 10 µL/MilliQ) was then respectively added per 90 mL of the medium and the final concentration was adjusted to 100 nM (but 100 µM for the cisplatin). At 96 hours after the start of culture, washing was performed 3 times with the medium component; 10 µL of Cell Counting Kit-8 (Dojindo, Kumamoto, Japan) was added to the cell culture medium; incubation was carried out for 1.5 hours in a 37° C. and 5% CO$_2$ atmosphere; and the viable cell percentage was quantitated by measurement of the absorbance at 450 nm.

Figure 6:
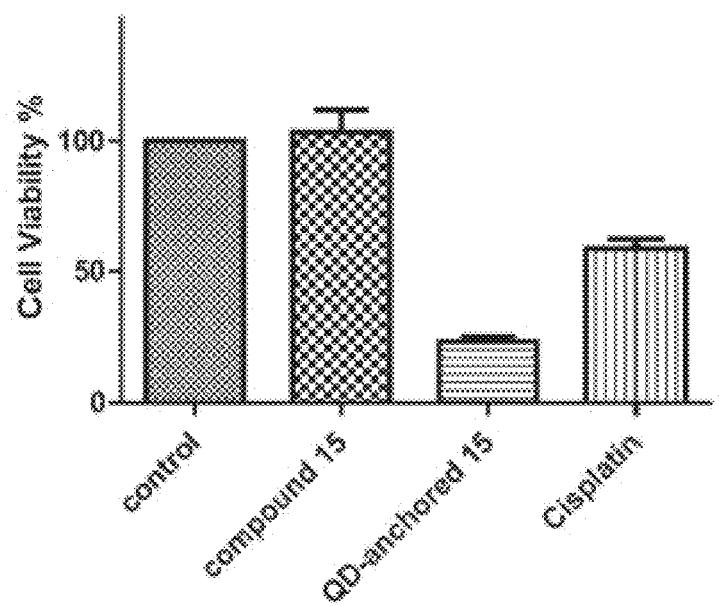
FIG. 6 shows the results for the breast cancer cell killing action of fluorescent nanoparticles that display compound 15 (100 nM QD-anchored 15). (a) The viability of MCF-7 cells was quantitated by MTT assay after coculture for 96 hours with the fluorescent nanoparticles displaying compound 15 or the individual test agents used for comparison. (b) Status of breast cancer cells after culture for 96 hours with the particular test agent (scale bar size=50 μm). Lysosomes are stained green; nuclei are stained blue; and QDs display a red fluorescence.
Figure 6:
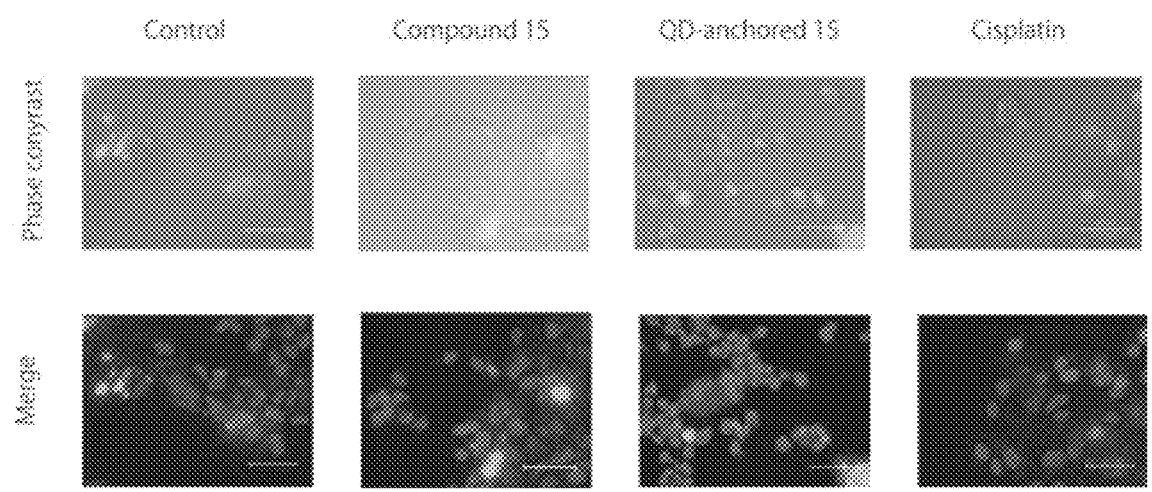

FIG. 6 gives the results for the breast cancer cell killing action of the fluorescent nanoparticles displaying compound 15 (100 nM QD-anchored 15). (a) The percentage viability for the MCF-7 cells was quantitated by the MTT assay after coculture for 96 hours in the presence of the fluorescent nanoparticles displaying compound 15 or in the presence of the individual test agents used for comparison. (b) Status of the breast cancer cells after culture for 96 hours with each test agent (scale bar size=50 µm). The lysosomes are stained green and the nuclei are stained blue and the QDs exhibit a red fluorescence.

The fluorescent nanoparticles displaying compound 15 (100 nM QD-anchored 15) significantly stopped the growth of MCF-7 breast cancer cells and, at a viability of approximately 20% after culture for 96 hours, exhibited a strong anticancer action far beyond that of 100 mM cisplatin (1000-times the dose of the 100 nM QD-anchored 15) (FIG.

6a). In addition, floating dead cells with altered shapes were observed only in the experimental systems seeded with 100 nM QD-anchored 15 or 100 μM cisplatin (FIG. 6b).
Reference Documents
1. M. Kurogochi, et al., *J. Biol. Chem.* 2004, 279, 44704-44712
2. T. Ohyanagi, et al., *J. Am. Chem. Soc.* 2011, 133, 12057-12517
3. R. S. Tan, et al., *ACS Chem. Biol.* 2015, 10, 2073-2086
Example 3: Sialidase Inhibitor-Bearing Nanoparticles
(1) Synthesis of Compound 20
Reaction Scheme 5
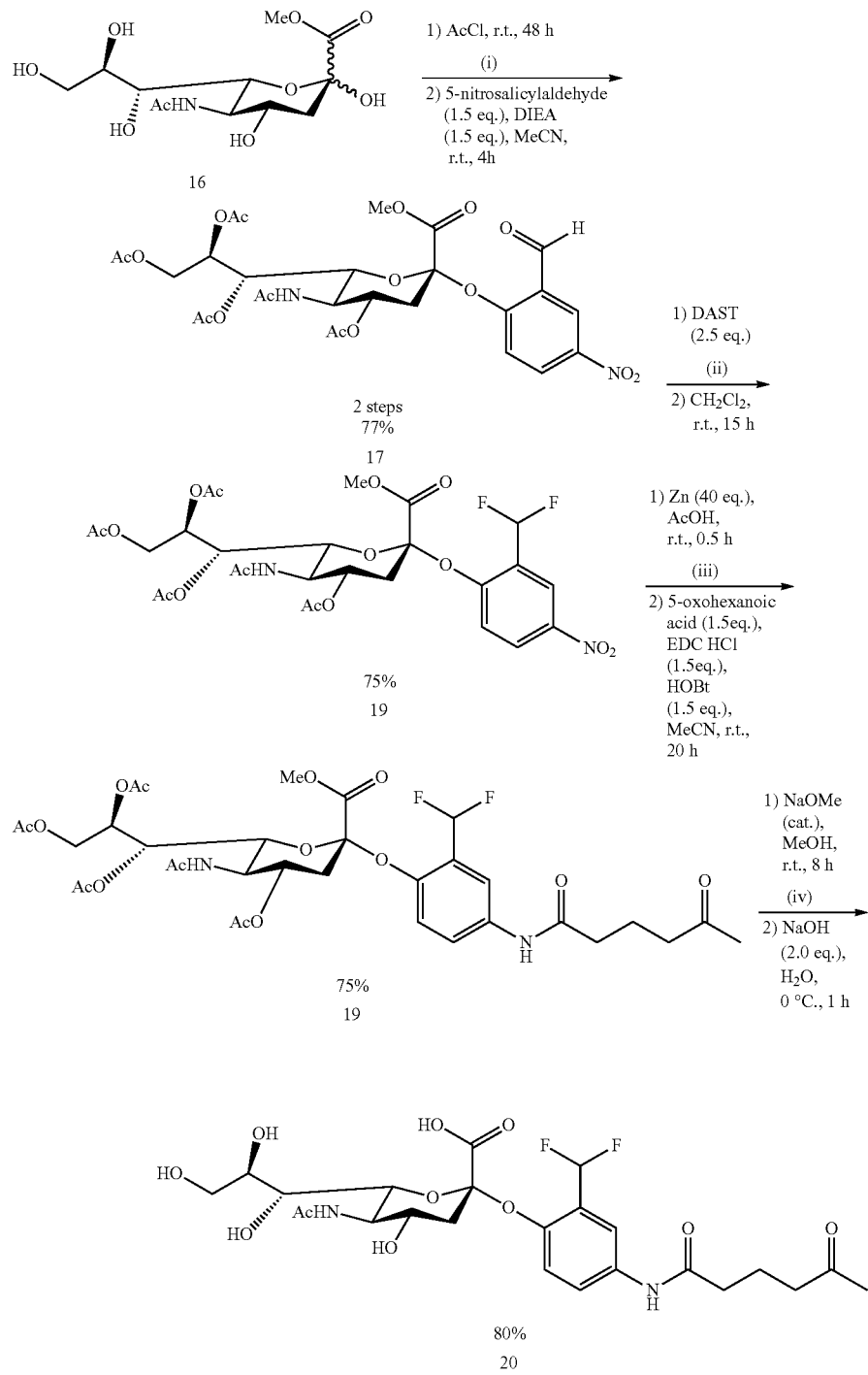

Synthesis route to compound 20: (i) 1) AcCl, r.t., 48 h, 2) 5-nitrosalicylaldehyde (1.5 eq.), DIEA (1.5 eq.), MeCN, r.t., two step yield 77%, (ii) DAST (2.5 eq.), $CH_2Cl_2$, r.t., 15 h, 77%, (iii) 1) Zn (40 eq.), AcOH, r.t., 0.5 h, 2) 5-oxohexanoic acid (1.5 eq.), EDC (1.5 eq.), HOBt (1.5 eq.), MeCN, r.t., 20 h, 75%, (iv) 1) NaOMe (cat.), MeOH, r.t., 8 h, 2) NaOH (2.0 eq.), $H_2O$, 0° C., 1 h Compound 20 was synthesized using sialic acid as the starting material. Compound 17 was selectively obtained by the glycosylation reaction of 5-nitrosalicylaldehyde using the compound 16 as the sugar reaction donor via halogenation, and this was followed by conversion to compound 18 by conversion of the aldehyde group in 17 to the difluoromethyl group using diethylamino sulfur trifluoride (DAST). The nitro group in compound 18 was then reduced; compound 19 was derived by the condensation of 5-oxohexanoic acid in the presence of 1-ethyl-3-(3-dimethylaminopropyl)carbodiimide hydrochloride (EDC); and the target compound 20 indicated below was efficiently prepared by the deacetylation reaction and demethylation reaction.

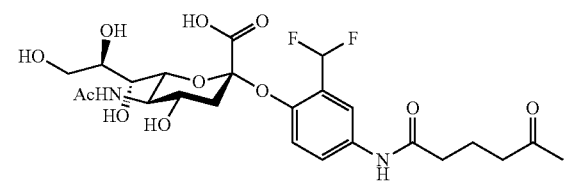

Structural information for compound 20: $^1$H NMR (500 Hz, $D_2O$) δ ppm 7.56 (d, 1H), 7.33 (dd, 1H), 7.25 (d, 1H), 6.98 (t, 1H), 3.82-3.71 (m, 4H), 3.65 (ddd, 1H), 3.53-3.48 (m, 2H), 3.09 (q, 6H), 2.79 (dd, 1H), 2.53 (t, 2H), 2.29 (t, 2H), 2.08 (s, 3H), 1.92 (s, 3H), 1.86-1.77 (m, 3H), 1.17 (t, 8H); ESI-MS 561.1901 $[M+H]^+$ (2) Construction of Fluorescent Nanoparticles Displaying Compound 20

The procedure for constructing fluorescent nanoparticles (quantum dots) displaying compound 20 is given in the following reaction scheme 6.

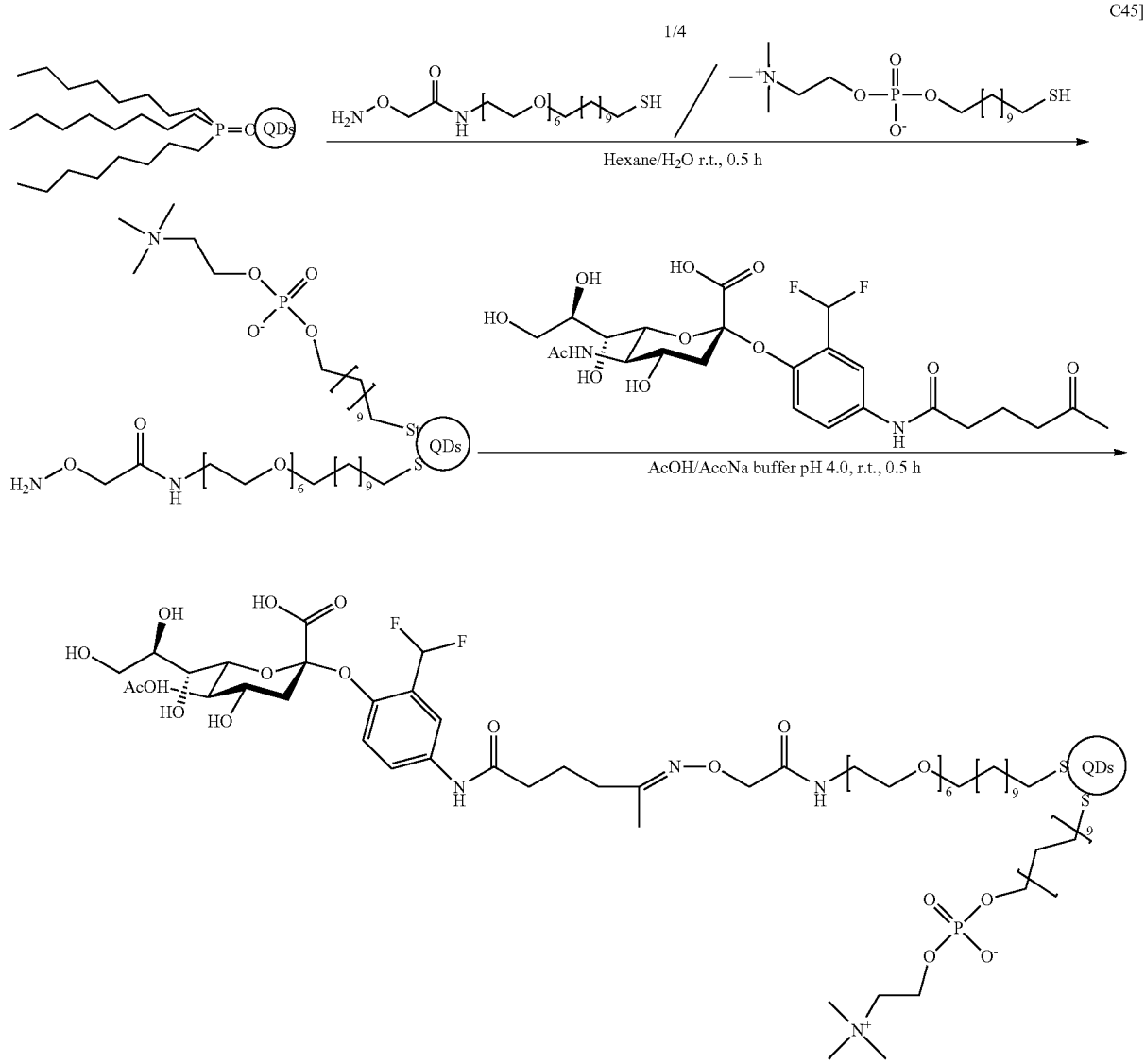

Compound 20 was displayed on fluorescent nanoparticles (quantum dots, Invitrogen Qdot (registered trademark) 655) according to the methods described in Reference Documents 1 and 2. Preparation of the reactive nanoparticle precursor AO/PC SAM-QDs (AO/PC=1/4): MeOH (50 µL) and i-PrOH (100 µL) were added to TOPO-QDs (1 µM, 50 µL/octane) and the nanoparticles were pelleted by centrifugation followed by removal of the solvent and redispersion by the addition of hexane (50 µL). The aminooxy linker (10 mM, 10 µL/MeOH), which had been preliminarily activated by deprotection, the phosphorylcholine linker (100 mM, 4 µL/MeOH), NaBH$_4$ (1 µL, 12 wt % in 14 N NaOH), and MilliQ (50 µL) were then added and stirring was carried out for 30 minutes to conduct ligand exchange and produce the reactive nanoparticle precursor AO/PC SAM-QDs (AO/PC=1/4). This was purified by ultrafiltration (YM 50) and submitted to reaction with compound 20.

Figure 7:
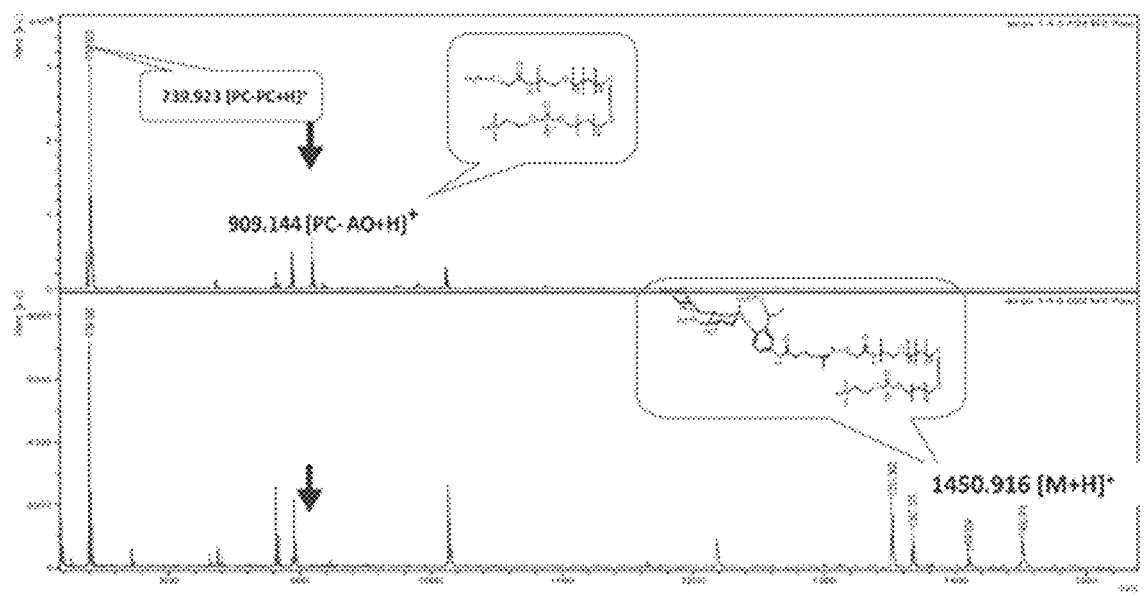
FIG. 7 confirms by MALDI-TOFMS the display of a compound in Example 3 on the nanoparticle surface.

Display of compound 20 on the nanoparticle: The AO/PC SAM-QDs (AO/PC=1/4) and compound 20 (30 mM, 10 µL/MilliQ) were dispersed in AcOH/AcONa buffer (pH 4, 100 µL); stirring was carried out for 30 minutes at room temperature; and purification by ultrafiltration (YM 50) was performed to obtain the target substance. It was confirmed by MALDI-TOFMS that compound 20 was displayed on the nanoparticle surface (FIG. 7).

(3) Antitumor Effect (1) of the Fluorescent Nanoparticles Displaying Compound 20 (Inhibitory Effect on Breast Cancer Cell Proliferation)

Intracellular imaging: Human breast cancer cells (MCF-7, P16, acquired from ATCC) were seeded at 5000 cell/200 µL/well and were incubated for 48 hours on D-MEM high glucose and 10% fetal bovine serum (FBS) in an atmosphere of 37° C. and 5% CO$_2$. The fluorescent nanoparticles displaying compound 20 [10 nM compound 20-bearing AO/PC SAM-QDs (AO/PC=1/2)] were then added and the cell growth process was monitored for 8 hours after this. Observation with a fluorescence microscope was performed after the cells had been stained by the following procedure. After removal of the medium, the cells were washed 3 times with Opti-MEM; LysoTracker R Green DND-26 (200 µL, 5 nM/Opti-MEM) was subsequently added; and lysosome staining was performed by incubation for 30 minutes under conditions of 37° C. and 5% CO$_2$. Nuclear staining was then performed by the addition of Hoechst (2 µL, 0.1 ng/µL/Opti-MEM) and additional incubation for 15 minutes in an atmosphere of 37° C. and 5% CO$_2$, followed by washing 3 times with Opti-MEM and imaging (FIG. 8). FIG. 8 shows the intracellular behavior in cancer cells of fluorescent nanoparticles that display compound 20 (10 nM): intracellular trafficking of fluorescent nanoparticles after the start (1 to 8 hours) of breast cancer cell (MCF-7) culture (scale bar size=50 µm). Uptake into the cells of the fluorescent nanoparticles displaying compound 20 is demonstrated by FIG. 8.

(4) Antitumor Effect (2) of the Fluorescent Nanoparticles Displaying Compound 20 (Breast Cancer Cell Killing Action)

Quantitation of dead cells by the MTT assay: MCF-7 cells (5×10$^4$/100 mL/well) were incubated for 24 hours in a 37° C. and 5% CO$_2$ atmosphere, and QD-anchored inhibitor 15 (1 µM, 10 µL/MilliQ) was then respectively added per 90 mL of the medium and the final concentration was adjusted to 100 nM (but 100 µM for the cisplatin). At 96 hours after the start of culture, washing was performed 3 times with the medium component; 10 µL of Cell Counting Kit-8 (Dojindo, Kumamoto, Japan) was added to the cell culture medium; incubation was carried out for 1.5 hours in a 37° C. and 5% CO$_2$ atmosphere; and the viable cell percentage was quantitated by measurement of the absorbance at 450 nm.

Figure 9:
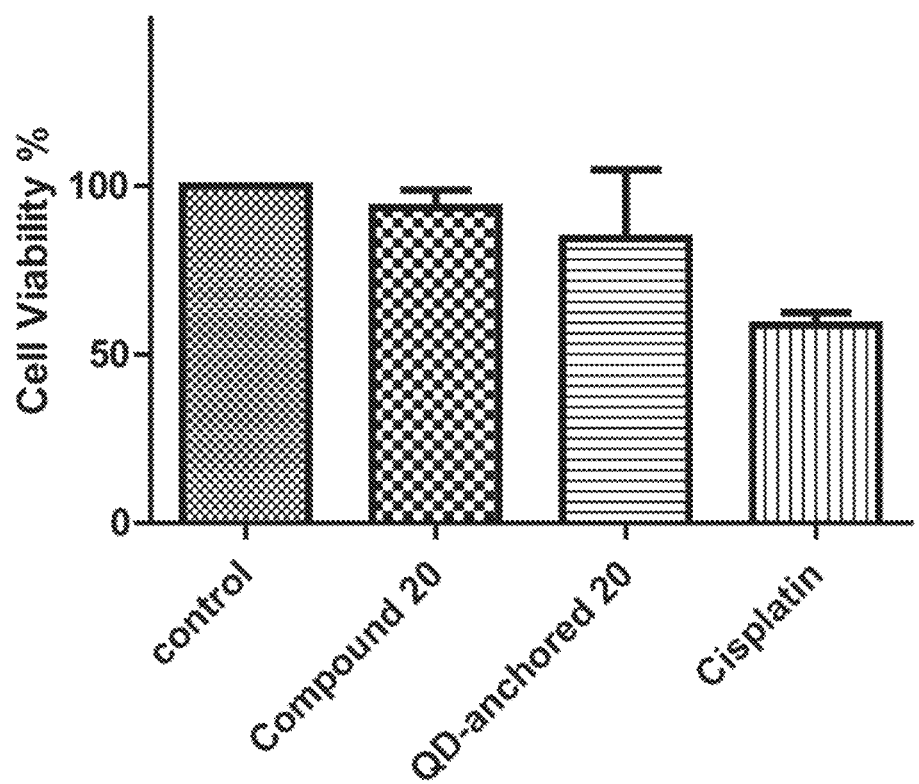
FIG. 9 shows the results for the breast cancer cell killing action of fluorescent nanoparticles that display compound 20 (100 nM QD-anchored 15). The viability of MCF-7 cells was quantitated by MTT assay after coculture for 96 hours with fluorescent nanoparticles displaying compound 20 or the individual test agents used for comparison.

FIG. 9 shows breast cancer cell killing action of the fluorescent nanoparticles displaying compound 20 (100 nM QD-anchored 15): The viability of the MCF-7 cells was quantitated by the MTT assay after coculture for 96 hours in the presence of the fluorescent nanoparticles displaying compound 20 or in the presence of the individual test agents used for comparison. A significant difference could not be observed for the growth inhibition of MCF-7 breast cancer cells by the fluorescent nanoparticles displaying compound 20 (100 nM QD-anchored 20). The system with compound 20 did exhibit a suicide substrate activity, although this was weak.

Reference Documents

1. T. Ohyanagi, et al., *J. Am. Chem. Soc.* 2011, 133, 12057-12517
2. R. S. Tan, et al., *ACS Chem. Biol.* 2015, 10, 2073-2086

Example 4: Effect on Hepatocellular Carcinoma of Lysosomal Enzyme Inhibitor-Bearing Fluorescent Nanoparticles A: Intracellular Imaging of Lysosomal Enzyme Inhibitor-Bearing Fluorescent Nanoparticles Human liver cancer cells (HepG2, P3, acquired from ATCC) were seeded at 5000 cell/200 µL/well and were incubated for 48 hours on D-MEM high glucose and 10% fetal bovine serum (FBS) in an atmosphere of 37° C. and 5% CO$_2$. A compound 7-bearing, phospholipid-coated fluorescent nanoparticle solution, a compound 15-bearing, phospholipid-coated fluorescent nanoparticle solution, and a compound 20-bearing, phospholipid-coated fluorescent nanoparticle solution [10 nM inhibitor-bearing AO/PC SAM-QDs (AO/PC=1/2), prepared according to a previous report (T. Ohyanagi et al., *J. Am. Chem. Soc.* 2011, 133, 12507-12517)] were then added, respectively, and the cancer cell growth process was monitored for 8 hours after the start of coculture. Imaging with a fluorescence microscope was performed after the cells had been stained by the following procedure. This protocol is summarized as follows. After removal of the medium, the cells were washed 3 times with Opti-MEM; LysoTracker R Green DND-26 (200 µL, 5 nM/Opti-MEM) was subsequently added; and lysosome staining was performed by incubation for 30 minutes under conditions of 37° C. and 5% CO$_2$. Nuclear staining was then performed by the addition of Hoechst (2 µL, 0.1 ng/µL/Opti-MEM) and additional incubation for 15 minutes in an atmosphere of 37° C. and 5% CO$_2$, followed by washing 3 times with Opti-MEM and observation.imaging in each case with a fluorescence microscope (FIG. 10).

Figure 10A:
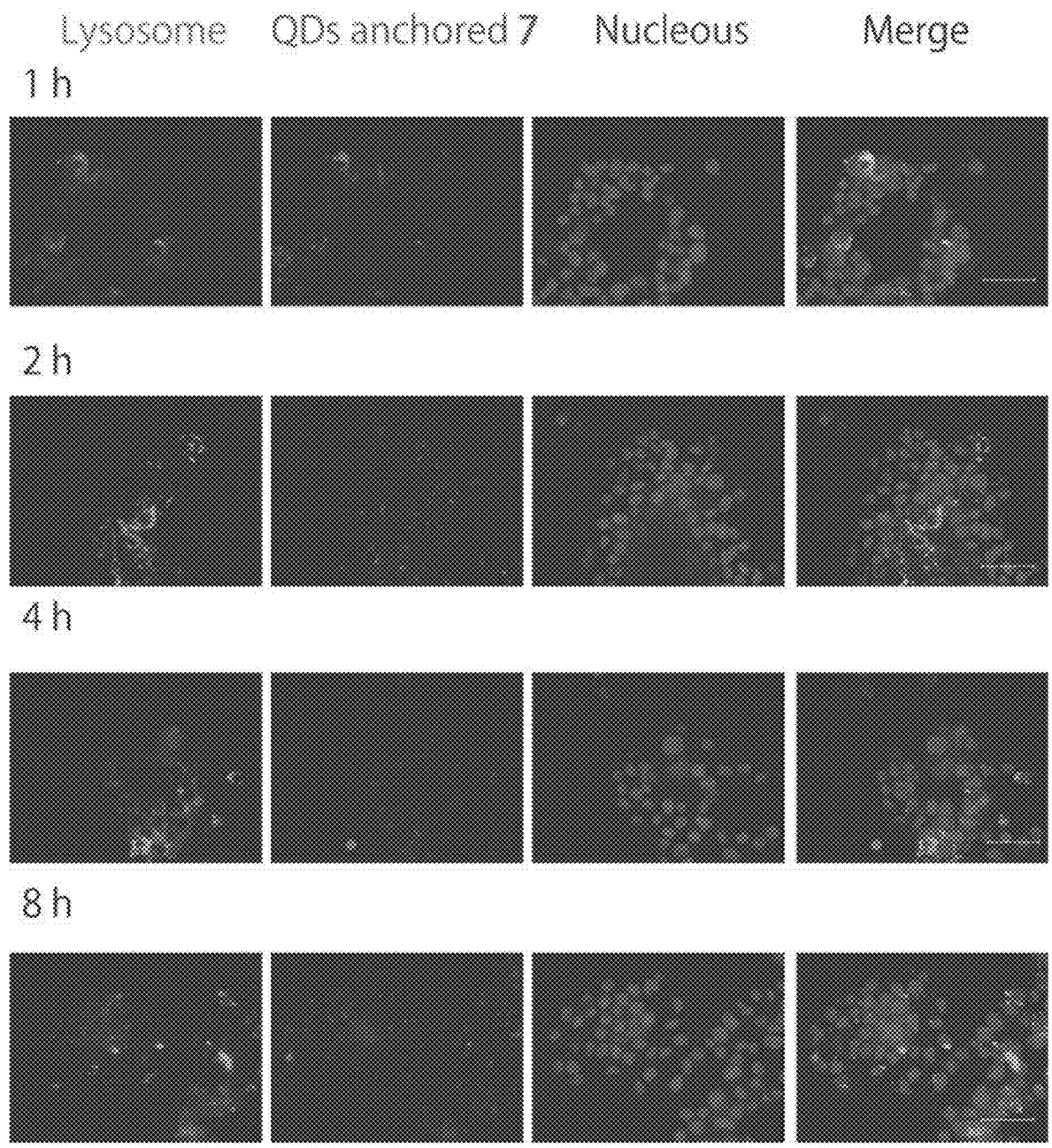
FIG. 10A shows the intracellular behavior in cancer cells (HepG2 cells) of compound 7-bearing fluorescent nanoparticles (10 nM): intracellular behavior after the start of coculture (1 to 8 hours) of liver cancer cells (HepG2) with the inhibitor-bearing, phospholipid-coated fluorescent nanoparticles (scale bar size=50 μm).
Figure 10B:
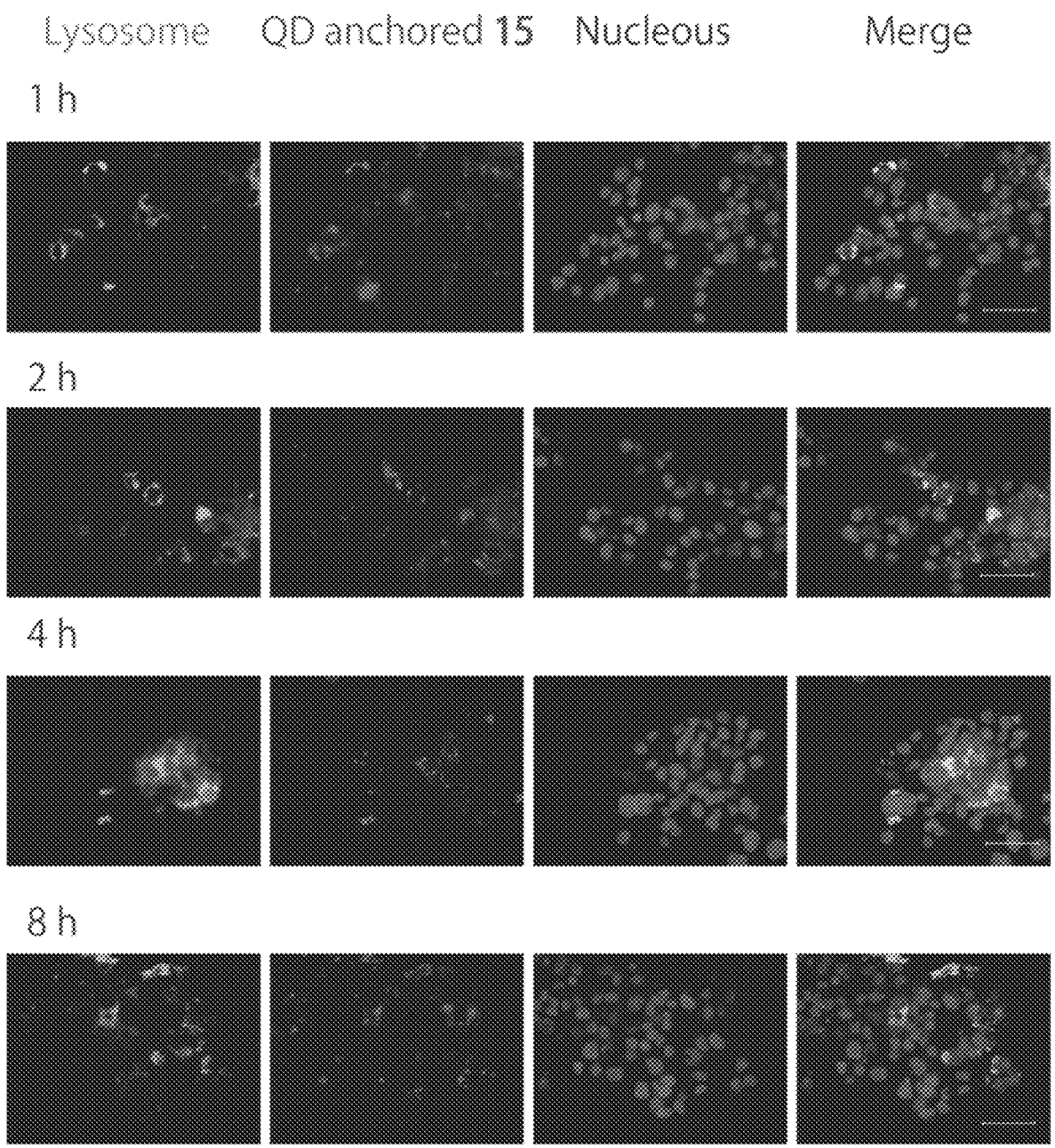
FIG. 10B shows the intracellular behavior in cancer cells (HepG2 cells) of compound 15-bearing fluorescent nanoparticles (10 nM): intracellular behavior after the start of coculture (1 to 8 hours) of liver cancer cells (HepG2) and the inhibitor-bearing, phospholipid-coated fluorescent nanoparticles (scale bar size=50 μm).
Figure 10C:
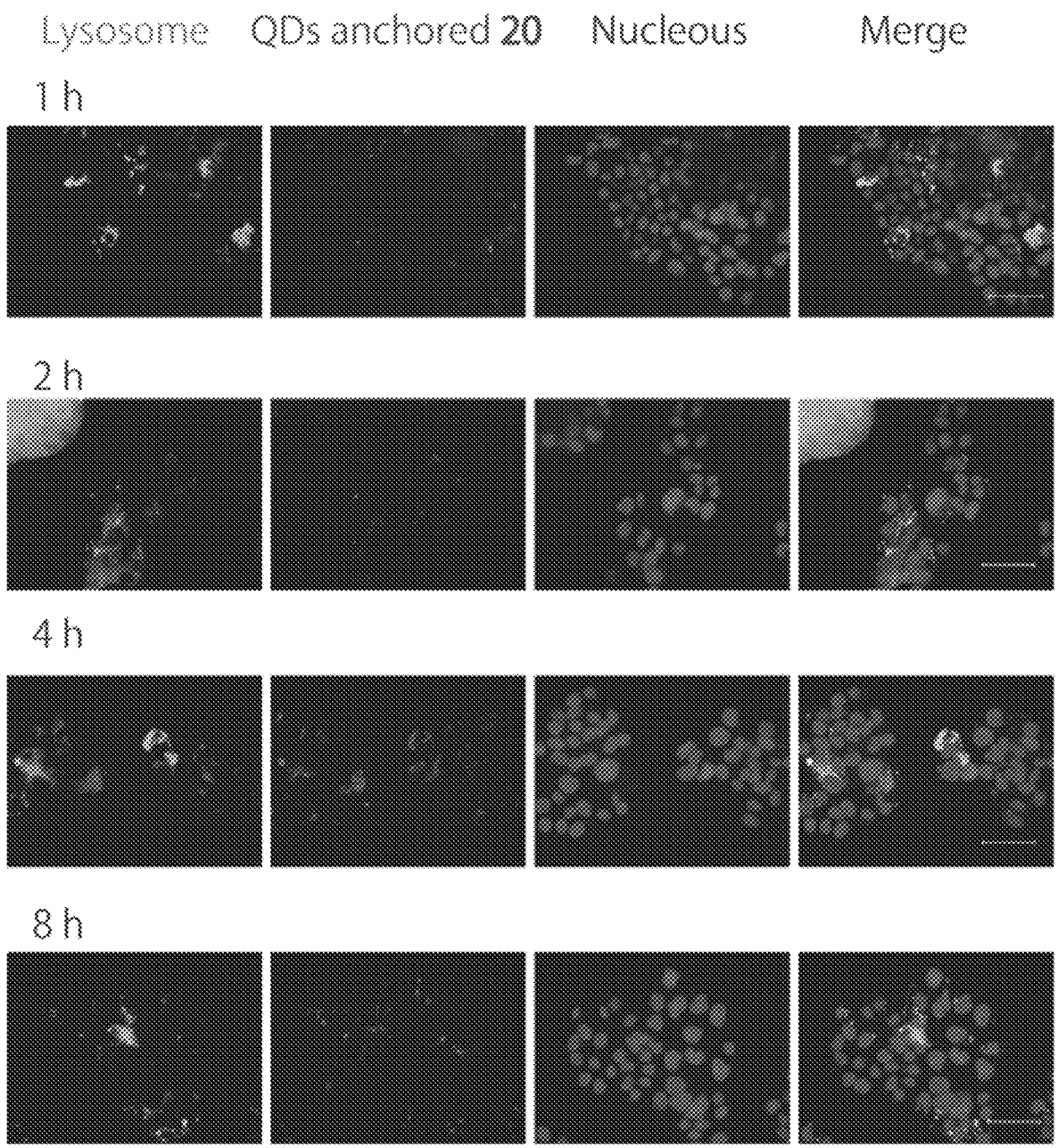
FIG. 10C shows the intracellular behavior in cancer cells (HepG2 cells) of compound 20-bearing fluorescent nanoparticles (10 nM): intracellular behavior after the start of coculture (1 to 8 hours) of liver cancer cells (HepG2) with the inhibitor-bearing, phospholipid-coated fluorescent nanoparticles (scale bar size=50 μm).

As shown in FIGS. 10A to 10C, in all cases a portion of the phospholipid-coated fluorescent nanoparticles (red color) had already escaped from the lysosomes at 1 hour after the start of coculture with the cancer cells. After 8 hours, more-or-less most was not localized in the lysosome and seemed to move freely within the cytoplasm. It has already been reported that, regardless of the type of cancer cell, phospholipid-coated nanoparticles not carrying an inhibitor do not move within the cytoplasm and continue to be localized within the lysosome (R. S. Tan et al., *ACS Chem. Biol.* 2015, 10, 2073-2086). Compounds 7, 15, and 20 are irreversible inhibitors of, respectively, hexosaminidase, galactosidase, and sialidase and are expected during the inhibition reaction to induce a conformational change around the active center of the target enzyme. On the other hand, these sugar-degrading enzymes distributed in the lysosome are thought to all strongly contribute to stabilization of the lysosome membrane, and it is believed that the nanoparticles escape into the cytoplasm as a result of the production of significant changes (damage to the membrane) in the structure and properties of the lysosome membrane due to the inhibition reactions with these enzymes.

B: Antitumor Effect of Fluorescent Nanoparticles Carrying a Lysosomal Enzyme Inhibitor (Hecatocellular Carcinoma Killing Effect)

Figure 11:
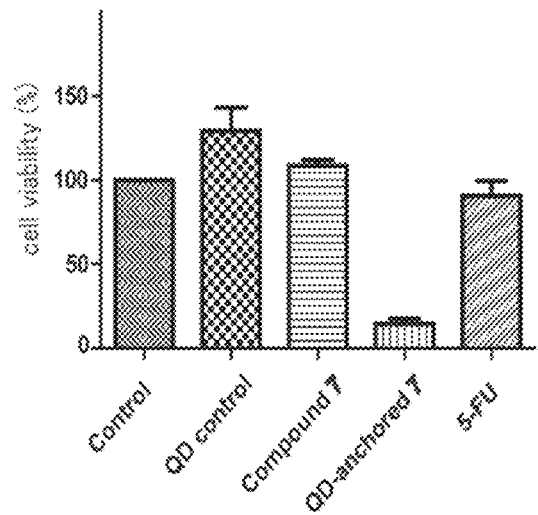
FIG. 11 shows liver cancer cell killing action of fluorescent nanoparticles carrying inhibitor 7 (A), 15 (B), or 20 (C) (100 nM): the viability of the HepG2 cells was quantitated by a cell viability assay (MTT method) after coculture for 96 hours in the presence of each of these inhibitor-bearing, phospholipid-coated fluorescent nanoparticles or the particular agent used for comparison.
Figure 11:
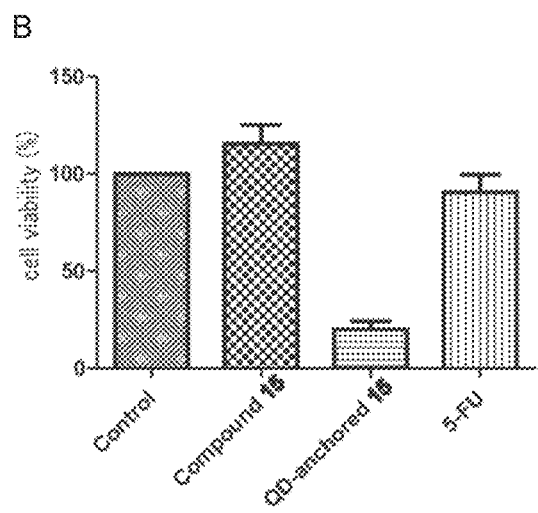
Figure 11:
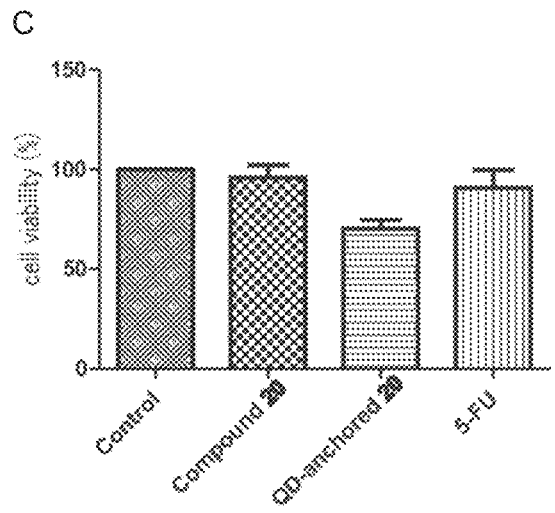
Figure 12:
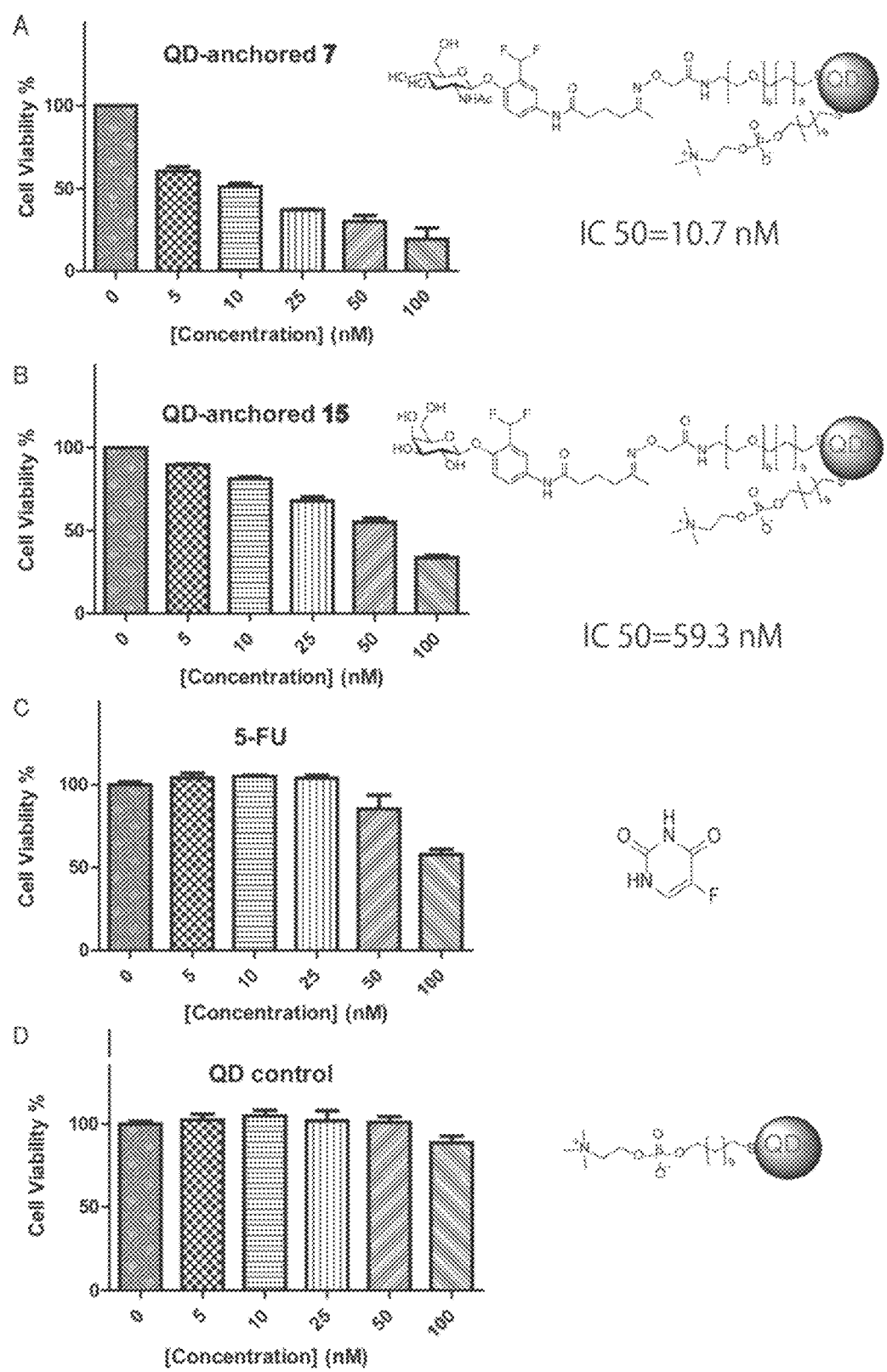
FIG. 12 shows hepatocellular carcinoma killing action of compound 7-bearing fluorescent nanoparticles (1 to 100 nM QD-anchored 7): the viability of HepG2 cells was quantified by a cell viability assay after coculture for 96 hours in the presence of compound 7-bearing fluorescent nanoparticles or the individual test agents used for comparison.

HepG2 cells ($5\times10^4$/100 mL/well) were incubated for 24 hours in a 37° C. and 5% $CO_2$ atmosphere, and compounds 7, 15, and 20 (10 µL of a solution brought to 1 µM by dissolution in MilliQ) were then respectively added per 90 µL of the medium and the final concentration was adjusted to 100 nM. At 96 hours after the start of coculture, washing was performed 3 times with the medium component and 10 µL of Cell Counting Kit-8 (Dojindo, Kumamoto, Japan) was added to the cell culture medium; incubation was carried out for 1.5 hours in a 37° C. and 5% $CO_2$ atmosphere; and the viable cell percentage was quantitated by measurement of the absorbance at 450 nm. A 100 nM 5-fluorouracil solution (5-FU) was used as a control agent (FIG. 11).

As shown in FIGS. 11A to 11C, the compound 7-bearing fluorescent nanoparticles and the compound 15-bearing fluorescent nanoparticles (100 nM) significantly inhibited the growth of the HepG2 liver cancer cells, with live cells after coculture for 96 hours being approximately 15% and 30%, respectively. In each of these experiments, a significant antitumor activity was not observed for the 5-FU (100 nM) used as a control agent, and the determination could thus be made that the compound 7-bearing fluorescent nanoparticles and compound 15-bearing fluorescent nanoparticles (100 nM) expressed a strong anticancer action far beyond that of 5-FU (100 nM) (FIGS. 11A and 11B).

On the other hand, under the same conditions the compound 20-bearing fluorescent nanoparticles (100 nM) expressed nothing more than a fairly weak antitumor effect in comparison to the aforementioned two drugs. This is thought to be due to the following: 1) the amount of sialidase expression within the lysosome is considerably lower than for galactosidase and hexosaminidase; 2) the α-sialosidic bond is more unstable under acidic conditions than other glycosidic bonds, and as a result there is a strong possibility that a certain degree of hydrolysis occurs in the lysosome; and 3) because sialic acid (Neu5Ac) is originally synthesized by an aldol reaction (via) through a ManNAc intermediate that is derived from the GlcNAc that is a key in the hexosamine synthesis pathway, the regeneration of sialic acid by sialidase does not necessarily make a large contribution as a CMP-Neu5Ac supply pathway.

C: Antitumor Effect of Fluorescent Nanoparticles Carrying the Lysosomal Enzyme Inhibitor 7 and Fluorescent Nanoparticles Carrying the Lysosomal Enzyme Inhibitor 15 (Determination of $IC_{50}$)

With reference to the preceding experimental results (FIG. 11), an evaluation of the dose dependence and a determination of the $IC_{50}$ value were performed for the antitumor effect of the inhibitor 7-bearing, phospholipid-coated fluorescent nanoparticles and the inhibitor 15-bearing, phospholipid-coated fluorescent nanoparticles, which had been confirmed to have a significant inhibitory activity on cancer cell growth versus the 5-FU comparative control agent. HepG2 cells ($5\times10^4$/100 mL/well) were incubated for 24 hours in a 37° C. and 5% $CO_2$ atmosphere, and QD-anchored 7 (1 to 0.05 µM, 10 µL/MilliQ), QD-anchored 15 (1 to 0.05 µM, 10 µL/MilliQ), QD control (1 to 0.05 µM, 10 µL/MilliQ), and 5-FU (1 to 0.01 µM, 10 µL/MilliQ) were then respectively added per 90 µL of the medium and the final concentration was adjusted to 100, 50, 25, 10, and 5 nM. At 96 hours after the start of coculture, washing was performed 3 times with the medium component and 10 µL of Cell Counting Kit-8 (Dojindo, Kumamoto, Japan) was added to the cell culture medium; incubation was carried out for 1.5 hours in a 37° C. and 5% $CO_2$ atmosphere; and the viability of the cancer cells was then quantitated by measurement of the absorbance (450 nm) on the supernatant.

As shown in FIGS. 12A to 12D, the compound 7-bearing fluorescent nanoparticles and the compound 15-bearing fluorescent nanoparticles (QD-anchored 7 and QD-anchored 15) both inhibited the growth of HepG2 liver cancer cells in a concentration dependent manner, and a strong antitumor action far beyond that of the 5-FU ($IC_{50}$>100 nM) comparative control agent was expressed after 96 hours of coculture (QD-anchored 7: $IC_{50}$=10.7 nM, QD-anchored 15: $IC_{50}$=59.3 nM). In view of the fact that the native $IC_{50}$ of compounds 7, 15, and 20 for various glycosidases in vitro is on the order of mM in all cases (Reference Documents 1 to 3), the results given in FIG. 12 confirm that "the specific (local) concentration effect into the lysosome interior of small-molecule irreversible inhibitors due to being carried on a nanoparticle" is very effective.

Reference Documents

Documents related to compound synthesis procedures (inhibitors of sugar-degrading enzymes by irreversible reaction mechanisms)
1. M. Ichikawa, et al. *Bioorg. Med. Chem. Lett.* 2001, 11, 1769-1773.
2. M. Kurogochi, et al., *J. Biol. Chem.* 2004, 279, 44704-44712.
3. H. Hinou, et al. *Biochemistry* 2005, 44, 11669-11675.

Documents related to properties and fabrication methods for phospholipid monomolecular film-coated quantum dots (biomembrane mimetic fluorescent nanoparticles)
4. T. Ohyanagi, et al., *J. Am. Chem. Soc.* 2011, 133, 12057-12517.
5. R. S. Tan, et al., *ACS Chem. Biol.* 2015, 10, 2073-2086.

Example 5: Phospholipid Monomolecular Film-Coated Fluorescent Nanoparticles Carrying a Kinase Inhibitor (Novel Sorafenib Derivative): Synthesis and Antitumor Effect on HepG2 Hepatocellular Carcinoma A: Synthesis of a Novel Sorafenib Derivative (32)

Sorafenib is a therapeutic agent for hepatocellular carcinoma and renal cell cancers, and it has been shown that, due to its hydrophobic structure, almost all of the sorafenib in the blood of the patient is nonspecifically adsorbed to the serum albumin and al-acidic proteins and the uptake efficiency into cancer tissue (cancer cells) is very low as a consequence. Due to this, it has been recently pointed out that there is a strong possibility that the significant antitumor activity at the $IC_{50}$=4.5 µM level, as seen in experiments with cultured cancer cells that express the target kinase group, cannot actually be thoroughly expressed in the patient or in vivo experimental systems such as animal disease models (Smith, M. A. and Hougton, *P. Clin. Cancer Res.* 2013, 19, 2828-2833).

If anchoring to a phospholipid-coated nanoparticle were possible without losing the basic performance in vitro as an excellent kinase inhibitor (for example, Ki (IC$_{50}$)=6.0, 22.0, and 90 nM versus recombinant Raf-1, BRAF, and VEGFR2, Wilhelm, S. M. et al., *Cancer Res.* 2004, 64, 2099-7109) that is due to the active structure of sorafenib (BAY 43-9006), then the sparing solubility of this drug could be substantially improved and there is great potential for the realization of an effective uptake into the cytoplasm due to the vigorous endocytosis of cancer cells. According to the three-dimensional structural information of a co-crystal of sorafenib and a kinase (VEGFR2) (Kania, R. S., et al. *Proc. Natl. Acad. Sci. USA* 2012, 109, 18281-18289), it has been shown that the 2-methylcarbamoyl group of the pyridine ring of sorafenib is partially exposed from the active site central region of VEGFR2 and is bound in a state having a relatively large degree of freedom. As a result, it was concluded that chemical modifications in the picolinic acid region would not affect the native kinase inhibitory activity, and the synthesis of compound 32 by the chemical modification of sorafenib at this position with a reactive linker was planned (refer to the synthesis scheme given below). Compound 32 is a novel sorafenib derivative that can be anchored to a phospholipid monolayer film-coated nanoparticle.

[C46]

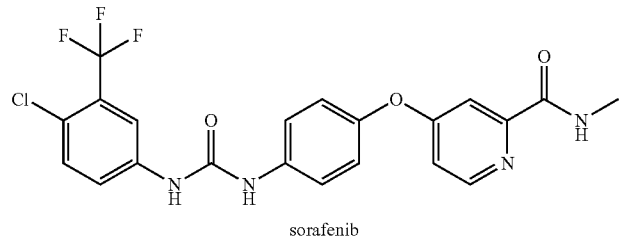

sorafenib

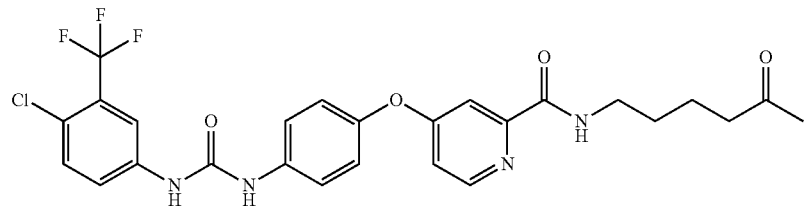

32

[C47]

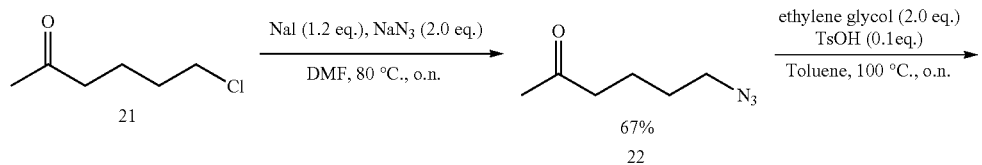

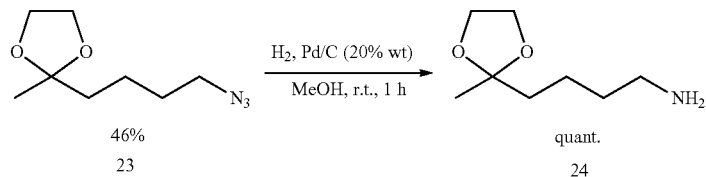

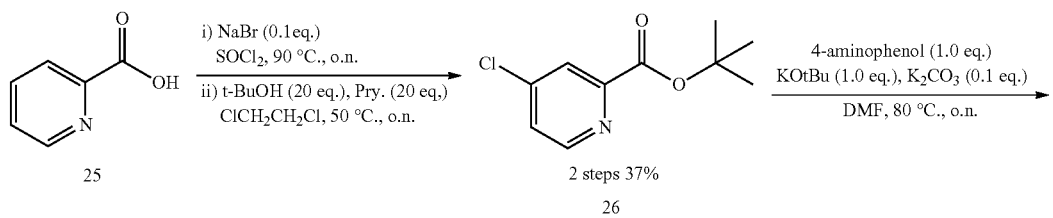

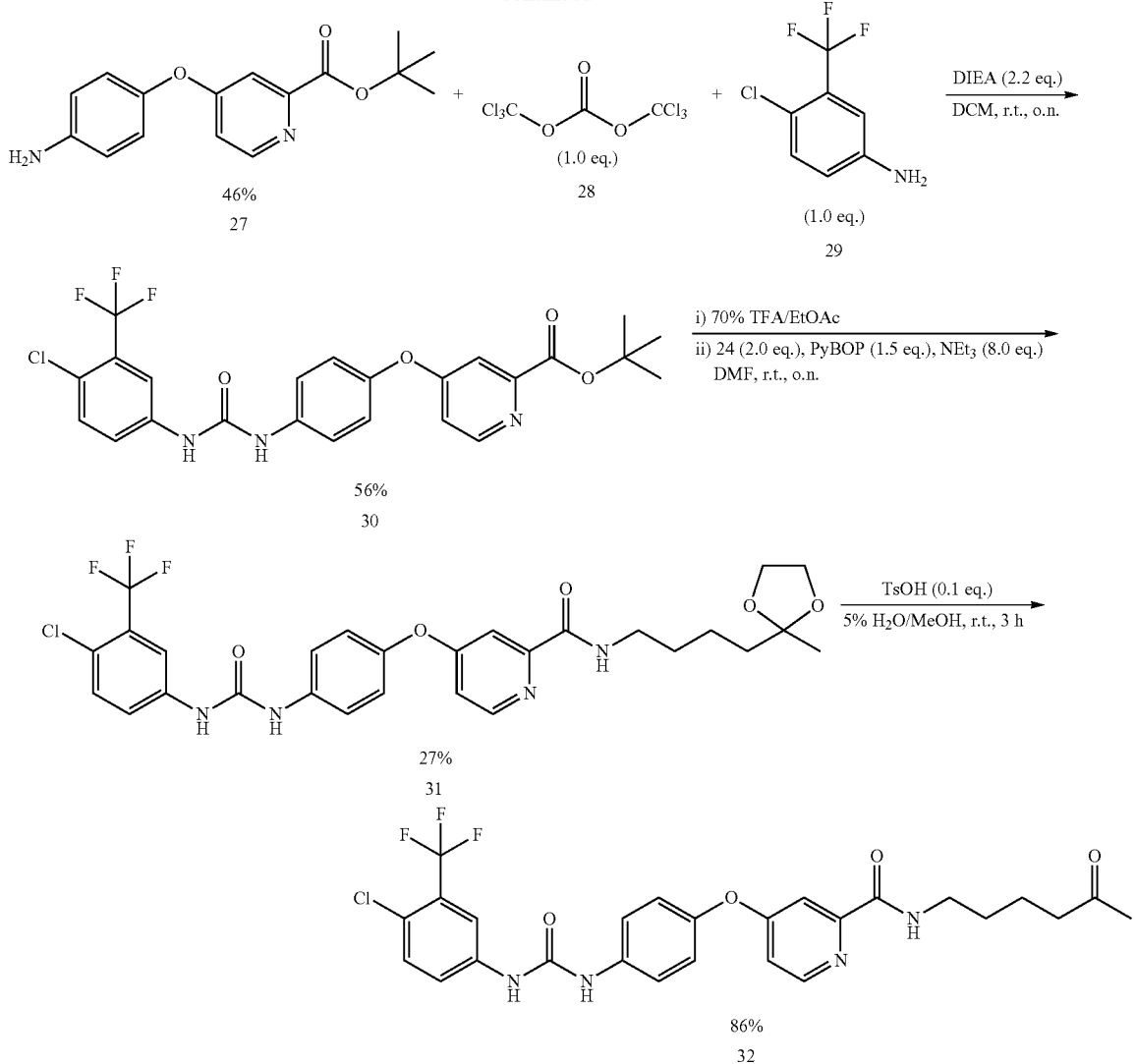

Synthesis Scheme for Novel Sorafenib Derivative 32

The sorafenib base structure 30 of compound 32 was prepared, with reference to a previous report (Hammock, B. D. et al., Bioorganic & Med. Chem. Lett. 2013, 23, 3732-3737), by the chlorination of the meta position of picolinic acid 25 followed by protection of the carboxylic acid to yield compound 26, which was condensed with 4-aminophenol to yield compound 27, which was itself then condensed with compound 29 in the presence of bis(trichloromethyl) carbonate 28. On the other hand, with the goal of modifying the picolinic acid region of sorafenib, the functional linker precursor 24 was synthesized by derivation from the starting material 21, which can be purchased. Compound 31 was derived by the condensation of the sorafenib derivative 30 and compound 24 in the presence of 1H-benzotriazole-1-yloxytris(pyrrolidine-1-yl)phosphonium.hexafluorophosphate (PyBOP), and finally the target compound 32 was then efficiently synthesized by deprotection by removal of the isopropylidene ketal group.

Structural information for compound 32: $^1$H NMR (500 Hz, DMSO) δ ppm 9.22 (s, 1H), 9.00 (s, 1H), 8.78 (t, 1H), 8.51 (d, 1H), 8.11 (s, 1H), 7.65 (d, 2H), 7.59 (m, 2H), 7.16 (d, 2H), 3.24 (t, 2H), 2.43 (t, 2H), 2.05 (s, 3H), 1.45 (m, 4H); ESI-MS 571.0406 [M+Na]$^+$ B: Synthesis of Phospholipid-Coated Fluorescent Nanoparticles Carrying the Novel Sorafenib Derivative (32)

Figure 13:
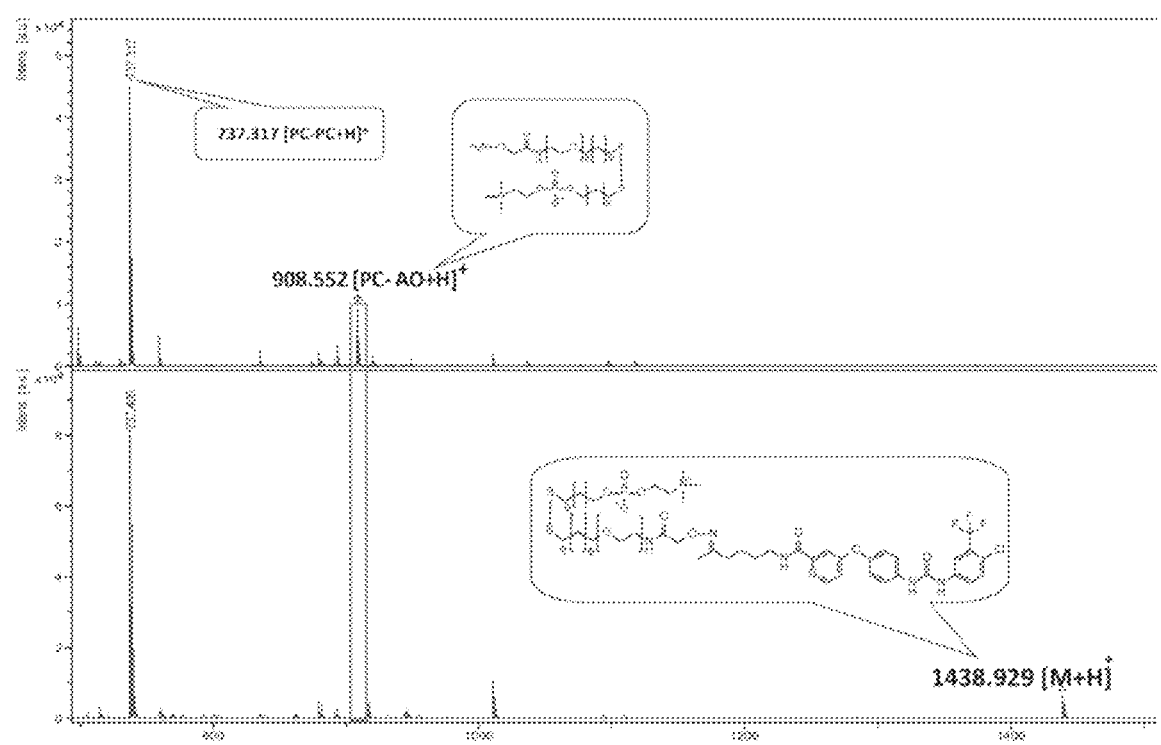
FIG. 13 shows MALDI-TOFMS of compound 32-bearing, phospholipid-coated fluorescent nanoparticles.

Operating according to a previous report (T. Ohyanagi et al., J. Am. Chem. Soc. 2011, 133, 12507-12517), MeOH (50 μL) and i-PrOH (100 μL) were added to TOPO-QDs (1 μM, 50 μL/octane) and the nanoparticles were pelleted by centrifugation followed by removal of the solvent and redispersion by the addition of hexane (50 μL). The aminooxy linker (10 mM, 5 μL/MeOH), which had been preliminarily activated by deprotection, the phosphorylcholine linker (100 mM, 8 μL/MeOH), NaBH$_4$ (1 μL, 12 wt % in 14 N NaOH), and MilliQ (50 μL) were then added and stirring was carried out for 30 minutes to conduct ligand exchange and produce the reactive nanoparticle precursor AO/PC SAM-QDs (AO/PC=1/16). This was purified by ultrafiltration (YM 50) and submitted to coupling with compound 32 (refer to the scheme given below). As shown by MALDI-TOFMS in FIG. 13, the reaction proceeded smoothly and the substitution reaction of all the aminooxy group with compound 32 could be confirmed.

Method for the preparation of compound 32-bearing, phospholipid-coated fluorescent nanoparticles

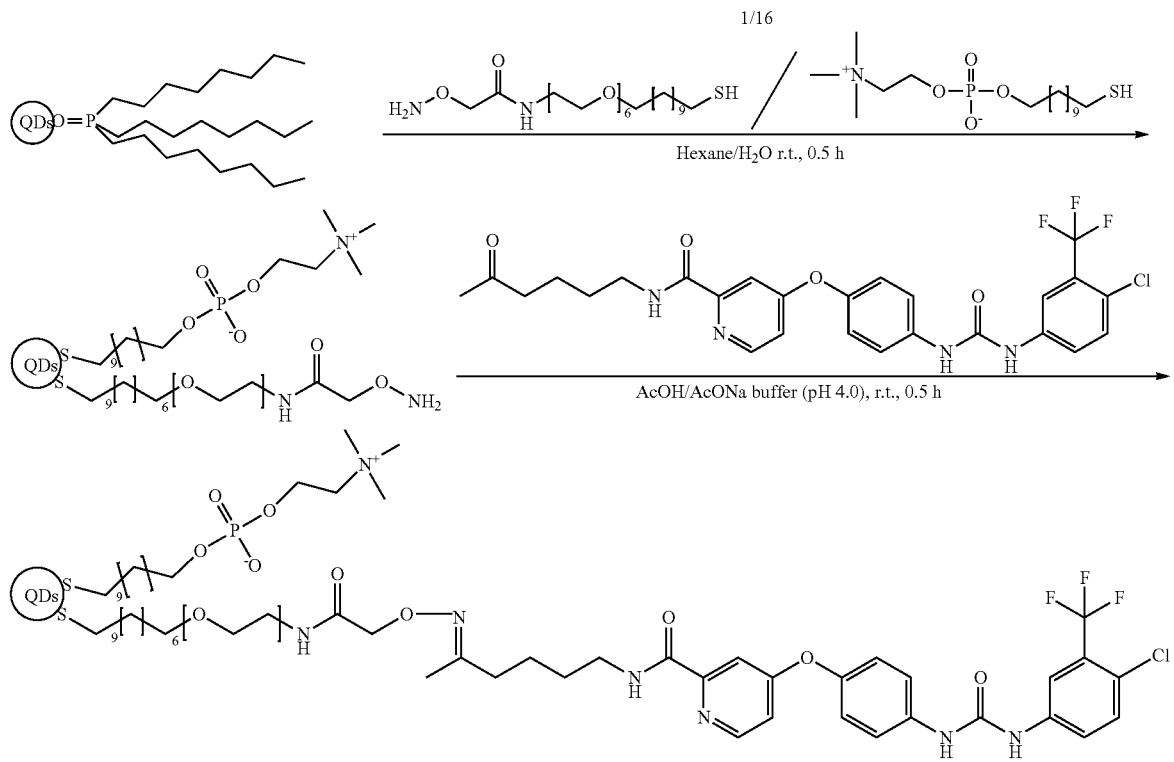

C: Imaging within Cancer Cells of the Fluorescent Nanoparticles Carrying the Sorafenib Derivative 32

Human liver cancer cells (HepG2, P8, acquired from ATCC) were seeded at 5000 cell/200 µL/well and were incubated for 48 hours on D-MEM high glucose and 10% fetal bovine serum (FBS) in an atmosphere of 37° C. and 5% $CO_2$. The 10 nM fluorescent nanoparticles [compound 32-bearing AO/PC SAM-QDs (AO/PC=1/16)] were then added, and the cancer cell growth process was monitored for 24 hours after the start of coculture. Imaging with a fluorescence microscope was performed after the cells had been stained by the following procedure. After removal of the medium, the cells were washed 3 times with Opti-MEM; LysoTracker R Green DND-26 (200 µL, 5 nM/Opti-MEM) was subsequently added; and lysosome staining was performed by incubation for 30 minutes under conditions of 37° C. and 5% $CO_2$. Nuclear staining was then performed by the addition of Hoechst (2 µL, 0.1 ng/µL/Opti-MEM) and additional incubation for 15 minutes in an atmosphere of 37° C. and 5% $CO_2$, followed by washing 3 times with Opti-MEM and imaging (FIG. 14).

Figure 14A:
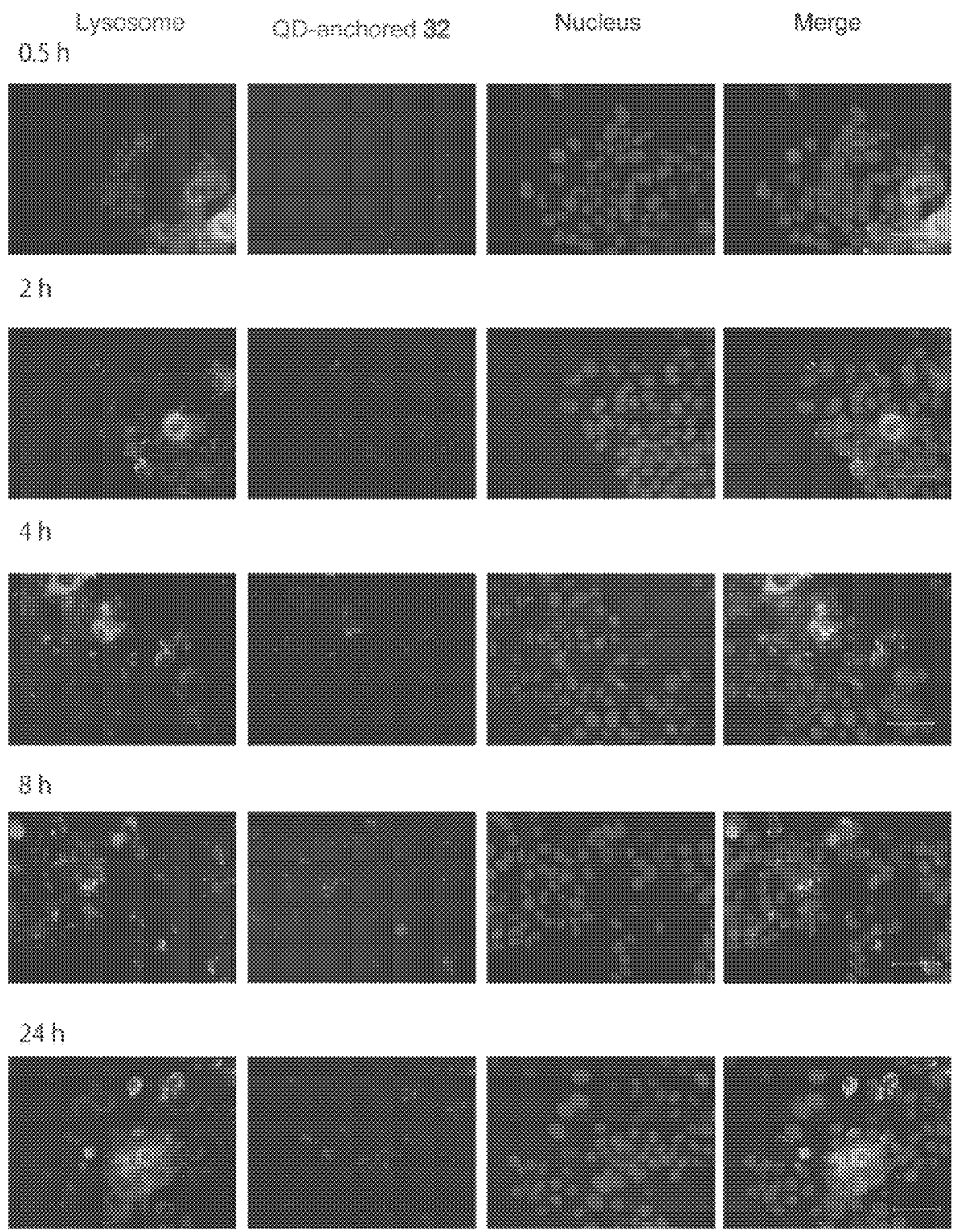
FIG. 14A shows the intracellular behavior in cancer cells of compound 32-bearing, phospholipid-coated fluorescent nanoparticles (10 nM): intracellular behavior at 0.5 to 24 hours after the start of coculture of the fluorescent nanoparticles with liver cancer cells (HepG2).
Figure 14B:
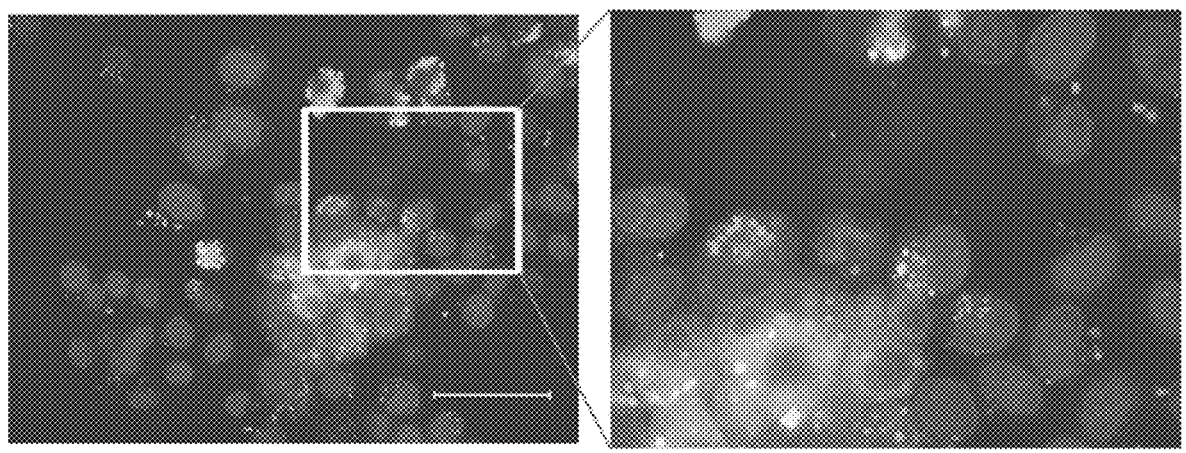
FIG. 14B is an enlargement of a part of FIG. 14A (scale bar size=50 μm).

As is clear from FIGS. 14A and 14B (enlarged view), the sorafenib derivative 32-bearing, phospholipid-coated fluorescent nanoparticles (red color) were shown to remain within the lysosome even after 24 hours from the start of coculture with the HepG2 cells. This result indicates that the kinase group targeted by sorafenib is not distributed within lysosomes but rather is delocalized into the cancer cell cytoplasm, and as a consequence this suggests that an improvement in the effect of sorafenib as an anticancer agent cannot be expected if the active entity (sorafenib derivative) from the endolysosome remains in a condition anchored by the linker to the nanoparticle. However, in the acidic environment in the lysosome (pH 4 and 5), it would also be expected that the oxime bond located in the linker moiety that connects the nanoparticle to the sorafenib would undergo hydrolysis relatively easily. As a consequence, the growth-inhibiting effect (antitumor activity) on HepG2 cells of the present drug was evaluated in comparison to the small-molecule sorafenib derivative 32.

2-D: Antitumor Effect (Hepatocellular Carcinoma Killing Action) of the Sorafenib Derivative 32-Bearing Fluorescent Nanoparticles Quantitation of dead cells by cell viability assay: HepG2 cells ($5\times10^4$/100 mL/well) were incubated for 24 hours in a 37° C. and 5% $CO_2$ atmosphere, and QD (1000 to 10 nM, 10 µL/MilliQ), QD-anchored 32 (1000 to 10 nM, 10 µL/MilliQ), and sorafenib derivative 32 ($10\times10^7$ to 10 nM, 10 µL/DMSO) were then respectively added per 90 µL of the medium and the final concentration was adjusted to 100 to 1 nM (but for compound 32, $1\times10^6$ to 1 nM because the $IC_{50}$ value was expected to be at the µM level). At 48 hours after the start of coculture, washing was performed 3 times with the medium component and 10 µL of Cell Counting Kit-8 (Dojindo, Kumamoto, Japan) was added to the cell culture medium; incubation was carried out for 1.5 hours in a 37° C. and 5% $CO_2$ atmosphere; and the cancer cell viability was quantitated by measurement of the absorbance at 450 nm (FIG. 15).

Figure 15:
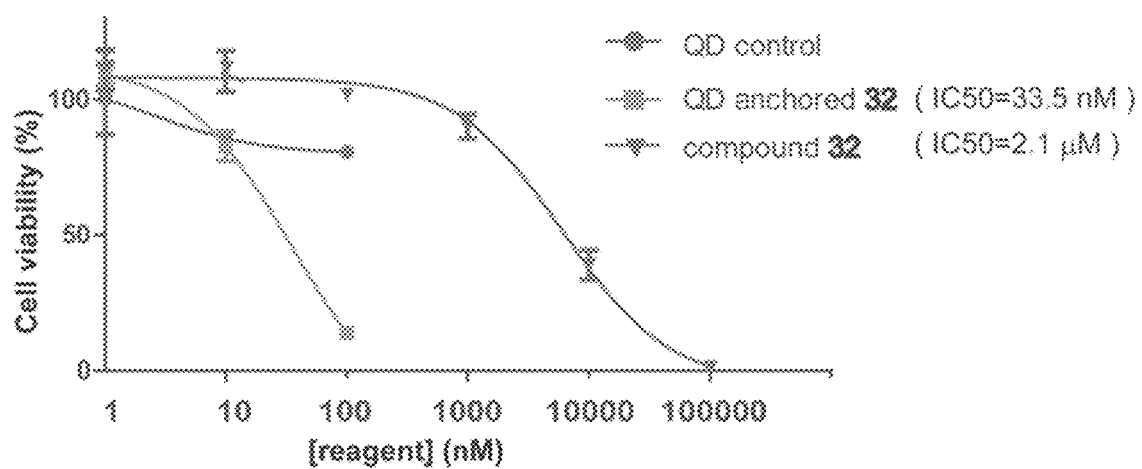
FIG. 15 shows the liver cancer cell killing action of sorafenib derivative 32-bearing, phospholipid-coated fluorescent nanoparticles (1 to 100 nM QD-anchored 32) and compound 32 (1 to $10^6$ nM): the viability of the cancer cells was quantitated by the MTT method after HepG2 cells had been cultured for 48 hours with the compound 32-bearing fluorescent nanoparticles, or with compound 32 by itself, or with only the nanoparticles.

Surprisingly, as shown in FIG. 15, the sorafenib derivative 32-bearing, phospholipid-coated nanoparticles (QD-anchored 32) were shown to strongly inhibit the growth of HepG2 liver cancer cells ($IC_{50}$=33.5 nM). On the other hand, the antitumor activity ($IC_{50}$=2.1 µM) when only the small-molecule compound 32 not carried on nanoparticles was cocultured with the cancer cells was about the same as the antitumor effect of sorafenib on HepG2 cells (IC$_{50}$=4.5 µM, Lin, L. et al., Cancer Res. 2006, 66, 11851-11858). These experimental results proved that, by anchoring on a phospholipid-coated nanoparticle, the antitumor activity of sorafenib can be enhanced at least 100-fold (or, the patient dosage can be kept at approximately 1/100).

INDUSTRIAL APPLICABILITY

The present invention is useful in fields involved with anticancer agents.

The invention claimed is:

1. A conjugate, comprising: a nanoparticle which comprises a surface; a lysosomal enzyme inhibitor or a kinase inhibitor of general formula (A); and a phospholipid mimetic substance of general formula (B), wherein the lysosomal enzyme inhibitor or the kinase inhibitor and the phospholipid mimetic substance are carried on the surface of the nanoparticle:

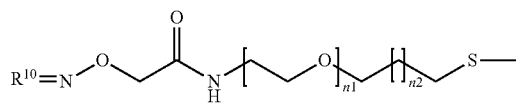
(A)

wherein in general formula (A), n1 is an integer from 2 to 30, n2 is an integer from 2 to 30, -S- is an S-terminal, the -S- terminal is a nanoparticle-anchor moiety, and $R^{10}$ is a suicide substrate moiety comprising at least one sugar residue, at least one group reactive with a lysosomal enzyme and a linker KL or a kinase inhibition moiety comprising a group having reactivity with a tyrosine kinase and a linker LK or comprising a kinase inhibitor,

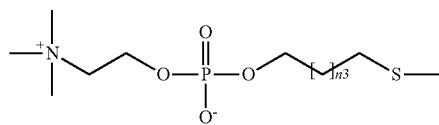
(B)

and wherein in general formula (B), n3 is an integer from 2 to 30, -S is an S-terminal, and the -S- terminal is a nanoparticle-anchor moiety;

wherein the linker is represented by the formula (L):

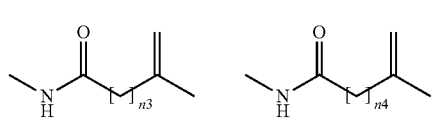
(L)

wherein n4 is an integer from 1 to 10, —NH— terminal binds to a remaining portion of $R^{10}$ and a double bond of —C(=)— terminal binds to =N—O— in general formula (A).

2. The conjugate of claim 1, further comprising a substance of general formula (A') that is carried on the nanoparticle surface:

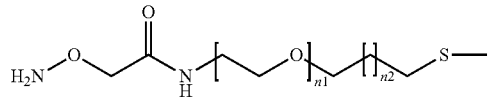
(A')

wherein in general formula (A'), n1 is an integer from 2 to 30, n2 is an integer from 2 to 30, -S- is an S-terminal, and the -S- terminal is a nanoparticle-anchor moiety.

3. The conjugate of claim 2, wherein, in general formula (B), n3 is 5 to 30 and in general formulas (A), (B), and (A'), a sum of n1 and n2 is equal to or greater than n3.

4. The conjugate of claim 1, wherein the reactive group of the suicide substrate moiety is reactive with an active center of a lysosomal enzyme.

5. The conjugate of claim 4, wherein the suicide substrate moiety comprises (i) at least one sugar residue selected from the group consisting of an N-acetyl-D-glucosamine residue, an N-acetyl-D-galactosamine residue, a galactose residue, a glucose residue, a fucose residue, a mannose residue, and a sialic acid residue; and (ii) at least one group reactive with a lysosomal enzyme selected from the group consisting of a difluoromethylaryl group and a trifluoromethylaryl group.

6. The conjugate of claim 1, wherein the suicide substrate moiety comprising at least one sugar residue, at least one reactive group and a linker KL is a functional group of formula (E'):

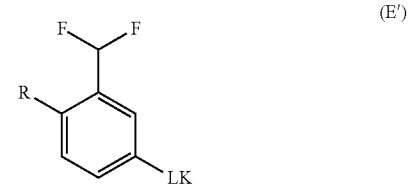
(E')

wherein in the formula (E'), R is at least one sugar residue selected from the group consisting of an N-acetyl-D-glucosamine residue, an N-acetyl-D-galactosamine residue, a galactose residue, a glucose residue, a fucose residue, a mannose residue, and a sialic acid residue; and LK is a linker represented by the formula (L).

7. The conjugate of claim 1, wherein the suicide substrate moiety comprising at least one sugar residue, at least one reactive group and a linker KL is at least one functional group of formula (7'), (15'), or (20'):

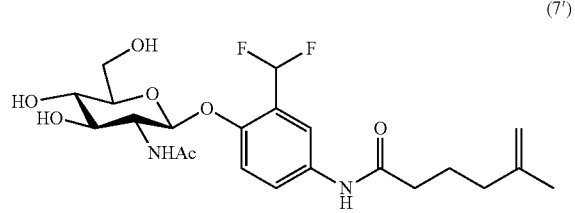
(7')

-continued

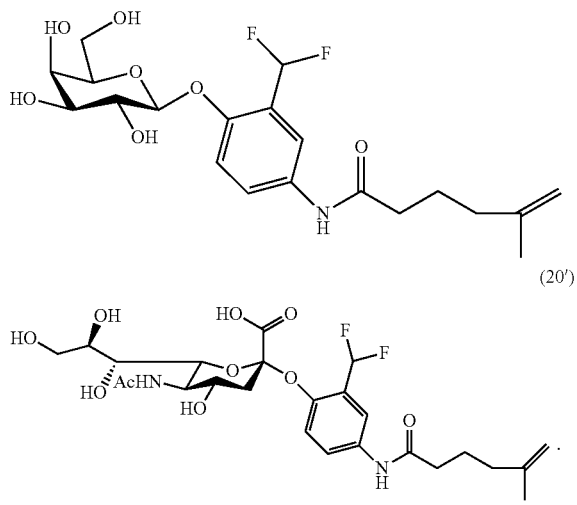

8. The conjugate of claim 1, wherein the kinase inhibition moiety comprising a group having reactivity with a kinase and a linker LK is a functional group of general formula [C]:

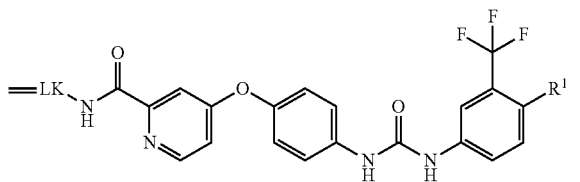

wherein LK is a linker represented by the formula (L) and $R^1$ is an electron-withdrawing group.

9. The conjugate of claim 1, wherein the kinase inhibition moiety comprising a group having reactivity with a kinase and a linker LK is a functional group of formula (32'):

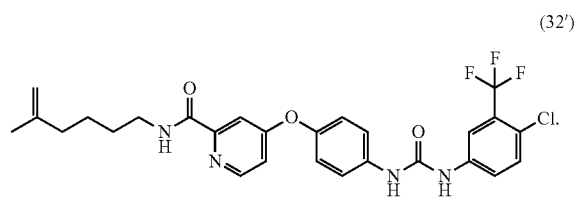 [SMILES: C=C(C)CCCCNC(=O)c1cc(Oc2ccc(NC(=O)Nc3ccc(Cl)c(C(F)(F)F)c3)cc2)ccn1]

10. The conjugate of claim 1, wherein the lysosomal enzyme inhibitor or kinase inhibitor of general formula (A) and the phospholipid mimetic substance of general formula (B) are present at a molar ratio of from 1:100 to 10:1.

11. The conjugate of claim 2, wherein the lysosomal enzyme inhibitor or kinase inhibitor of general formula (A) and the substance of general formula (A') are present at a molar ratio of from 1:100 to 100:0.

12. The conjugate according of claim 1, wherein the nanoparticle comprises a metal nanoparticle or a semiconductor nanoparticle.

13. The conjugate of claim 12, wherein the metal nanoparticle comprises at least one particle selected from the group consisting of a gold nanoparticle, a platinum nanoparticle, a silver nanoparticle, and a magnetic iron nanoparticle.

14. The conjugate of claim 12, wherein the semiconductor nanoparticle comprises a quantum dot.

15. The conjugate according of claim 1, wherein the nanoparticle has a particle diameter of from 0.1 to 100 nm.

16. The conjugate of claim 1, wherein the group having reactivity with a kinase is an electron-withdrawing group.

17. The conjugate of claim 16, wherein the electron-withdrawing group is a halogen atom(s), a nitro group, a cyano group, a tosyl group or an acyl group.

18. The conjugate of claim 1, wherein the kinase inhibitor is selected from sorafenib, gefitinib, erlotinib, cetuximab and panitumumab.

19. An anticancer agent comprising, as an active ingredient, the conjugate of claim 1.

20. The anticancer agent of claim 19, wherein the anticancer agent is effective against breast cancer, prostate cancer, hepatocellular cancer, pancreatic cancer, colon cancer, ovarian cancer, renal cancer, lung cancer, or brain tumor.

21. A method for producing the conjugate of claim 1, comprising:
(1) mixing a colloidal nanoparticle which comprises a surface with an inhibitor crosslinking precursor X of general formula (C) and a phospholipid mimetic substance precursor of general formula (D), to obtain a surface-modified nanoparticle carrying the inhibitor crosslinking precursor X and the phospholipid mimetic substance on the surface of the nanoparticle; and
(2) mixing the surface-modified nanoparticle obtained in (1) with a lysosomal enzyme inhibitor precursor Y or a kinase inhibitor precursor Z and bringing about ligation of said lysosomal enzyme inhibitor precursor Y or said kinase inhibitor precursor Z with the inhibitor crosslinking precursor X that is carried by the surface-modified nanoparticle, thereby to form a lysosomal enzyme inhibitor or kinase inhibitor of general formula (A), wherein the lysosomal enzyme inhibitor precursor Y comprises a suicide substrate moiety that comprises a reactive group that is reactive with an active center of a lysosomal enzyme, and wherein the kinase inhibitor precursor Z comprises a kinase inhibition moiety that contains a group having reactivity with a kinase:

[C8]

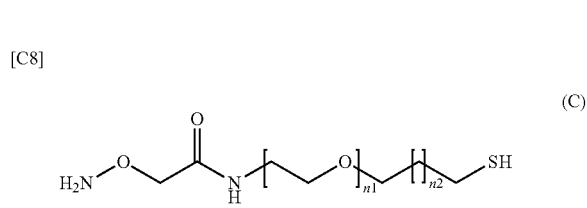

wherein in general formula (C), n1 is an integer from 2 to 30 and n2 is an integer from 2 to 30,

[C9]

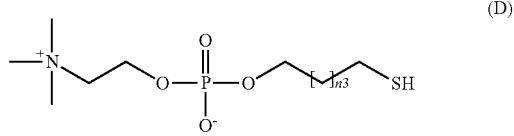

wherein in general formula (D), n3 is an integer from 2 to 30,

[C10]

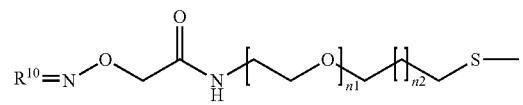

(A)

wherein in general formula (A), n1 is an integer from 2 to 30, n2 is an integer from 2 to 30, -S- is an S-terminal and the -S- terminal is a nanoparticle-anchor moiety, and $R^{10}$ is the suicide substrate moiety or the kinase inhibition moiety.

22. The method of claim 21, wherein the lysosomal enzyme inhibitor precursor Y comprises at least one compound of general formula (7), (15), or (20):

[C11]

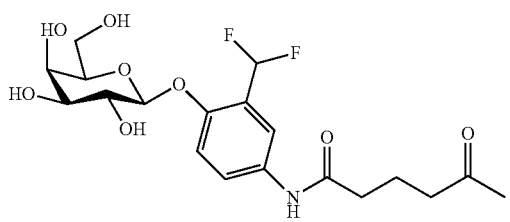

(7)

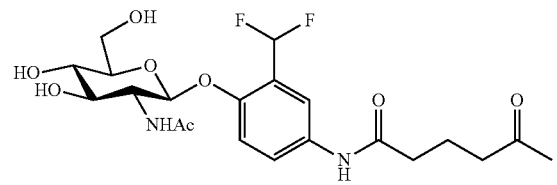

(15)

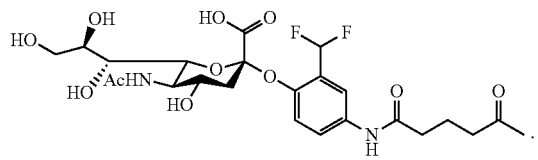

(20)

23. The method of claim 21, wherein the kinase inhibitor precursor Z comprises a compound of formula (32):

[C12]

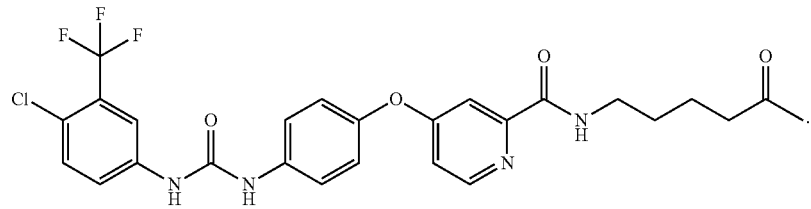

32

* * * * *